US010717772B2

(12) United States Patent
Metz et al.

(10) Patent No.: US 10,717,772 B2
(45) Date of Patent: Jul. 21, 2020

(54) RECOMBINANT BINDING PROTEINS TARGETING HER2 AND SERUM ALBUMIN, AND THEIR USES

(71) Applicant: Molecular Partners AG, Zurich-Schlieren (CH)

(72) Inventors: Clara Metz, Schlieren (CH); Ulrike Fiedler, Lörrach (DE); Ignacio Dolado, Rheinfelden (CH); Heike Maria Strobel, Basel (CH)

(73) Assignee: Molecular Partners AG, Zurich-Schlieren (CH)

( * ) Notice: Subject to any disclaimer, the term of this patent is extended or adjusted under 35 U.S.C. 154(b) by 0 days.

(21) Appl. No.: 15/710,001

(22) Filed: Sep. 20, 2017

(65) Prior Publication Data
US 2018/0155402 A1 Jun. 7, 2018

(30) Foreign Application Priority Data

Sep. 22, 2016 (EP) .................................... 16190221

(51) Int. Cl.
*C07K 14/47* (2006.01)
*A61P 35/00* (2006.01)
*A61K 38/00* (2006.01)

(52) U.S. Cl.
CPC .............. *C07K 14/47* (2013.01); *A61P 35/00* (2018.01); *A61K 38/00* (2013.01)

(58) Field of Classification Search
None
See application file for complete search history.

(56) References Cited

U.S. PATENT DOCUMENTS

| | | |
|---|---|---|
| 7,417,130 B2 | 8/2008 | Stumpp et al. |
| 8,110,653 B2 | 2/2012 | Stumpp et al. |
| 8,710,187 B2 | 4/2014 | Binz et al. |
| 8,722,618 B2 | 5/2014 | Jacobs et al. |
| 8,846,577 B2 | 9/2014 | Steiner et al. |
| 8,901,076 B2 | 12/2014 | Binz et al. |
| 9,006,389 B2 | 4/2015 | Stumpp et al. |
| 9,163,070 B2 | 10/2015 | Baumann |
| 9,206,244 B2 | 12/2015 | Baumann et al. |
| 9,221,892 B2 | 12/2015 | Binz |
| 9,284,361 B2 | 3/2016 | Steiner et al. |
| 9,289,466 B2 | 3/2016 | Binz et al. |
| 9,458,211 B1 | 4/2016 | Bakker et al. |
| 9,365,629 B2 | 6/2016 | Parmeggiani et al. |
| 9,447,142 B2 | 9/2016 | Steiner et al. |
| 2008/0206201 A1 | 8/2008 | Beier et al. |
| 2011/0033460 A1 | 2/2011 | Fendly et al. |
| 2015/0299265 A1 | 10/2015 | Fiedler et al. |
| 2016/0251404 A1 | 9/2016 | Tresch et al. |
| 2016/0362453 A1 | 12/2016 | Bakker et al. |

FOREIGN PATENT DOCUMENTS

| | | |
|---|---|---|
| WO | WO-1991/001743 | 2/1991 |
| WO | WO-2009/068625 | 6/2009 |
| WO | WO-2014/060365 | 4/2014 |

OTHER PUBLICATIONS

Https://www.uniprot.org/uniprot/P04626 accessed Oct. 11, 2018.*
Binz, "Designing Repeat Proteins: Well-expressed, Soluble and Stable Proteins from Combinatorial Libraries of Consensus Ankyrin Repeat Proteins" J Mol Biol (2003) 332(2), 489-503.
Forrer et al., "A novel strategy to design binding molecules harnessing the modular nature of repeat proteins," FEBS Letters (2003) 539 (1-3), 2-6.
Stumpp et al., "Designing Repeat Proteins: Modular Leucine-rich Repeat Protein Libraries Based on the Mammalian Ribonuclease Inhibitor Family", J Mol Biol (2003) 332(2), 471-487.
Kohl et al., "Designed to be stable: Crystal structure of a consensus ankyrin repeat protein", PNAS (2003) 100(4), 1700-1705.
Binz et al., High-affinity binders selected from designed ankyrin repeat protein libraries:, Nature Biotechnology (2004) 22(5), 575-582.
Amstutz et al., "Intracellular Kinase Inhibitors Selected from Combinatorial Libraries of Designed Ankyrin Repeat Proteins", JBC (2005), 280(26), 24715-24722.
He et al., "Ribosome display: cell-free protein display technology," Brief Funct Genomica Proteomic (2002) 1(2), 204-212.
Hanes et al., "In Vitro selection and evolution of functional proteins by using ribosome display," Proc Natl Acad Sci USA (1997) 94(10), 4937-4942.
Stumpp et al., "DARPins: A true alternative to antibodies," Curr Opin Drug Discov Devel. (2007) 10(2), 153-159.
Interlandi et al., "Characterization and Further Stabilization of Designed Ankyrin Repeat Proteins by Combining Molecular Dynamic Simulations and Experiments," J Mol Biol (2008) 375(3), 837-854.
Zahnd et al., "A designed ankyrin repeat protein evolved to picomolar affinity to Her2," J Mol Biol (2007) 369(4), 1015-1028.
Forrer et al., "Consensus Design of Repeat Proteins," ChemBioChem (2004) 5(2), 183-189.
Binz et al., "Designed Repeat Proteins—Molecules with Antibody-like Binding Properties," BIOforum Europe (2005) 9(4), 34-36, GIT Verlag GmbH & Co. KG, Darmstadt.
Binz et al., "Engineered proteins as specific binding reagents," Current Opinion in Biotechnology (2005) 16(4), 459-469.
Binz et al., "Engineering novel binding proteins from nonimmunoglobulin domains," Nature Biotechnology (2005) 23(10), 1257-1268.
Amstutz et al., "Rapid selection of specific MAP kinase-binders from designed ankyrin repeat protein libraries," Protein Engineering, Design & Selection (2006) 19(5), 219-229.

(Continued)

*Primary Examiner* — James H Alstrum-Acevedo
*Assistant Examiner* — Tara L Martinez
(74) *Attorney, Agent, or Firm* — Finnegan, Henderson, Farabow, Garrett & Dunner, LLP

(57) ABSTRACT

New recombinant binding proteins, comprising designed ankyrin repeat domain(s) with binding specificity for HER2, and comprising designed ankyrin repeat domain(s) with binding specificity for serum albumin, are disclosed, as well as nucleic acids encoding such recombinant binding proteins, pharmaceutical compositions comprising such recombinant binding proteins or nucleic acids and the use of such recombinant binding proteins, nucleic acids or pharmaceutical compositions in the treatment of diseases.

20 Claims, 7 Drawing Sheets
Specification includes a Sequence Listing.

(56) References Cited

OTHER PUBLICATIONS

Binz et al., "Crystal Structure of a Consensus-Designed Ankyrin Repeat Protein: Implications for Stability," Proteins: Structure, Function, and Bioinformatics (2006) 65(2), 280-284.

Kawe et al., "Isolation of Intracellular Proteinase Inhibitors Derived from Designed Ankyrin Repeat Proteins by Genetic Screening," J Biol Chem (2006) 281(52), 40252-40263.

Zahnd et al., "Selection and Characterization of Her2 Binding-designed Ankyrin Repeat Proteins," J Biol Chem (2006) 281(46), 35167-35175.

Boersma et al., "DARPins and other repeat protein scaffolds: advances in engineering and application," Curr Opin Biotechnol (2011) 22(6), 849-857.

Sennhauser et al., "Chaperone-Assisted Crystallography with DARPins", Structure (2008) 16(10), 1443-1453.

Steiner et al., "Efficient Selection of DARPins with Sub-nanomolar Affinities using SRP Phage Display", J Mol Biol (2008) 382(5), 1211-1227 (incl. Supplement).

Stump et al., "DARPins: A new generation of protein therapeutics", Drug Discovery Today (2008) 13(15-16), 695-701.

Veesler et al., "Crystal Structure and Function of a DARPin Neutralizing Inhibitor of Lactococcal Phage TP901-1", J Biol Chem (2009) 284(44), 30718-30726.

Eggel et al., "DARPins as Bispecific Receptor Antagonists Analyzed for immunoglobulin E Receptor Blockage", J Mol Biol (2009) 393(3), 598-607.

Kramer et al., "Structural Determinants for Improved Stability of Designed Ankyrin Repeat Proteins with a Redesigned C-Capping Module", J Mol Biol (2010) 404(3), 381-391.

Theurillat et al., "Designed ankyrin repeat proteins: a novel tool for testing epidermal growth factor receptor 2 expression in breast cancer", Modern Pathology (2010) 23(9), 1289-1297.

Zahnd et al., "Efficient Tumor Targeting with High-Affinity Designed Ankyrin Repeat Proteins: Effects of Affinity and Molecular Size", Cancer Res (2010) 70(4), 1595-1605 (incl. Supplement).

Zahnd et al., "Ribosome display: selecting and evolving proteins in vitro that specifically bind to a target," Nature Methods (2007) 4(3), p. 269-279.

Frejd F.Y., "Half-Life Extension by Binding to Albumin through an Albumin Binding Domain", in Therapeutic Proteins ed. By Kontermann R (2012), 269-283.

Hopp et al., "The effects of affinity and valency of an albumin-binding domain (ABD) on the half-life of a single-chain diabody-ABD fusion protein", Prot Eng (2010), 23(11), 827-834.

Bublil and Yarden, "The EGF receptor family: spearheading a merger of signaling and therapeutics", Curr. Opin. Cell Biol. (2007), 19(2), 124-134.

Capelan et al., "Pertuzumab: new hope for patients with HER2-positive breast cancer", Ann. Oncol. (2013), 24(2), 273-282.

Jost et al., "Structural Basis for Eliciting a Cytotoxic Effect in HER2-Overexpressing Cancer Cells via Binding to the Extracellular Domain of HER2", Structure (2013), 21(11), 1979-1991.

Main et al., "Design of Stable $\alpha$-Helical Arrays from an Idealized TPR Motif", Structure (2003), 11(5), 497-508.

Britton et al., "Quantification of Pancreatic Cancer Proteome and Phosphorylome: Indicates Molecular Events Likely Contributing to Cancer and Activity of Drug Targets", Plos One (2014), 9(3).

Tamaskovic et al., "Intermolecular biparatopic trapping of ErbB2 prevents compensatory activation of PI3K/AKT via RAS-p110 crosstalk", Nature Communications (2016), 7, 11672.

Ruschoff et al., "HER2 testing in gastric cancer: a practical approach", Modern Pathology (2012), 25(5), 637-650.

Wolff et al., "Recommendations for Human Epidermal Growth Factor Receptor 2 Testing in Breast Cancer: American Society of Clinical Oncology/College of American Pathologists Clinical Practice Guideline Update", J. Clin Oncol. (2013), 31(31), 3997-4014.

European Patent Office, Extended European Search Report for EP 16190221.8, dated Mar. 20, 2017 (7 pages).

* cited by examiner

SEQUENCE LISTING

```
<160> NUMBER OF SEQ ID NOS: 33

<210> SEQ ID NO 1
<211> LENGTH: 10
<212> TYPE: PRT
<213> ORGANISM: Artificial Sequence
<220> FEATURE:
<223> OTHER INFORMATION: His-tag

<400> SEQUENCE: 1

Met Arg Gly Ser His His His His His His
1               5                   10

<210> SEQ ID NO 2
<211> LENGTH: 5
<212> TYPE: PRT
<213> ORGANISM: Artificial Sequence
<220> FEATURE:
<223> OTHER INFORMATION: GlySer linker

<400> SEQUENCE: 2

Gly Gly Gly Gly Ser
1               5

<210> SEQ ID NO 3
<211> LENGTH: 7
<212> TYPE: PRT
<213> ORGANISM: Artificial Sequence
<220> FEATURE:
<223> OTHER INFORMATION: GlySer linker

<400> SEQUENCE: 3

Gly Gly Gly Gly Ser Gly Ser
1               5

<210> SEQ ID NO 4
<211> LENGTH: 10
<212> TYPE: PRT
<213> ORGANISM: Artificial Sequence
<220> FEATURE:
<223> OTHER INFORMATION: GlySer linker
```

```
<400> SEQUENCE: 4

Gly Gly Gly Gly Ser Gly Gly Gly Ser
1               5                   10

<210> SEQ ID NO 5
<211> LENGTH: 15
<212> TYPE: PRT
<213> ORGANISM: Artificial Sequence
<220> FEATURE:
<223> OTHER INFORMATION: GlySer linker

<400> SEQUENCE: 5

Gly Gly Gly Gly Ser Gly Gly Gly Gly Ser Gly Gly Gly Gly Ser
1               5                   10                  15

<210> SEQ ID NO 6
<211> LENGTH: 20
<212> TYPE: PRT
<213> ORGANISM: Artificial Sequence
<220> FEATURE:
<223> OTHER INFORMATION: GlySer linker

<400> SEQUENCE: 6

Gly Gly Gly Gly Ser Gly Gly Gly Gly Ser Gly Gly Gly Gly Ser Gly
1               5                   10                  15

Gly Gly Gly Ser
            20

<210> SEQ ID NO 7
<211> LENGTH: 8
<212> TYPE: PRT
<213> ORGANISM: Artificial Sequence
<220> FEATURE:
<223> OTHER INFORMATION: ProThr linker

<400> SEQUENCE: 7

Gly Ser Pro Thr Pro Thr Pro Thr
1               5

<210> SEQ ID NO 8
<211> LENGTH: 15
<212> TYPE: PRT
<213> ORGANISM: Artificial Sequence
<220> FEATURE:
<223> OTHER INFORMATION: ProThr linker

<400> SEQUENCE: 8

Gly Ser Pro Thr Pro Thr Pro Thr Thr Pro Thr Pro Thr Pro Thr
1               5                   10                  15

<210> SEQ ID NO 9
<211> LENGTH: 22
<212> TYPE: PRT
<213> ORGANISM: Artificial Sequence
<220> FEATURE:
<223> OTHER INFORMATION: ProThr linker

<400> SEQUENCE: 9

Gly Ser Pro Thr Pro Thr Pro Thr Thr Pro Thr Pro Thr Pro Thr Thr
1               5                   10                  15

Pro Thr Pro Thr Pro Thr
            20

<210> SEQ ID NO 10
<211> LENGTH: 159
```

<212> TYPE: PRT
<213> ORGANISM: Artificial Sequence
<220> FEATURE:
<223> OTHER INFORMATION: Designed ankyrin repeat domain

<400> SEQUENCE: 10

Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
            20                  25                  30

Thr Asp Asn Asp Gly Tyr Thr Pro Leu His Leu Ala Ala Ser Asn Gly
        35                  40                  45

His Leu Glu Ile Val Glu Val Leu Leu Lys Asn Gly Ala Asp Val Asn
    50                  55                  60

Ala Ser Asp Leu Thr Gly Ile Thr Pro Leu His Leu Ala Ala Ala Thr
65                  70                  75                  80

Gly His Leu Glu Ile Val Glu Val Leu Leu Lys His Gly Ala Asp Val
            85                  90                  95

Asn Ala Tyr Asp Asn Asp Gly His Thr Pro Leu His Leu Ala Ala Lys
            100                 105                 110

Tyr Gly His Leu Glu Ile Val Glu Val Leu Leu Lys His Gly Ala Asp
        115                 120                 125

Val Asn Ala Gln Asp Lys Phe Gly Lys Thr Ala Phe Asp Ile Ser Ile
    130                 135                 140

Asp Asn Gly Asn Glu Asp Leu Ala Glu Ile Leu Gln Lys Ala Ala
145                 150                 155

<210> SEQ ID NO 11
<211> LENGTH: 126
<212> TYPE: PRT
<213> ORGANISM: Artificial Sequence
<220> FEATURE:
<223> OTHER INFORMATION: Designed ankyrin repeat domain

<400> SEQUENCE: 11

Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
            20                  25                  30

Lys Asp Lys Asp Gly Tyr Thr Pro Leu His Leu Ala Ala Arg Glu Gly
        35                  40                  45

His Leu Glu Ile Val Glu Val Leu Leu Lys Ala Gly Ala Asp Val Asn
    50                  55                  60

Ala Lys Asp Lys Asp Gly Tyr Thr Pro Leu His Leu Ala Ala Arg Glu
65                  70                  75                  80

Gly His Leu Glu Ile Val Glu Val Leu Leu Lys Ala Gly Ala Asp Val
            85                  90                  95

Asn Ala Gln Asp Lys Phe Gly Lys Thr Ala Phe Asp Ile Ser Ile Asp
            100                 105                 110

Asn Gly Asn Glu Asp Leu Ala Glu Ile Leu Gln Lys Ala Ala
        115                 120                 125

<210> SEQ ID NO 12
<211> LENGTH: 126
<212> TYPE: PRT
<213> ORGANISM: Artificial Sequence
<220> FEATURE:
<223> OTHER INFORMATION: Designed ankyrin repeat domain

```
<400> SEQUENCE: 12

Gly Ser Asp Leu Gly Lys Lys Leu Leu Glu Ala Ala Arg Ala Gly Gln
1               5                   10                  15

Asp Asp Glu Val Arg Ile Leu Leu Lys Ala Gly Ala Asp Val Asn Ala
                20                  25                  30

Lys Asp Tyr Phe Ser His Thr Pro Leu His Leu Ala Ala Arg Asn Gly
            35                  40                  45

His Leu Lys Ile Val Glu Val Leu Leu Lys Ala Gly Ala Asp Val Asn
        50                  55                  60

Ala Lys Asp Phe Ala Gly Lys Thr Pro Leu His Leu Ala Ala Asn Asp
65                  70                  75                  80

Gly His Leu Glu Ile Val Glu Val Leu Leu Lys Ala Gly Ala Asp Val
                85                  90                  95

Asn Ala Gln Asp Ile Phe Gly Lys Thr Pro Ala Asp Ile Ala Ala Asp
                100                 105                 110

Ala Gly His Glu Asp Ile Ala Glu Val Leu Gln Lys Ala Ala
            115                 120                 125

<210> SEQ ID NO 13
<211> LENGTH: 126
<212> TYPE: PRT
<213> ORGANISM: Artificial Sequence
<220> FEATURE:
<223> OTHER INFORMATION: Designed ankyrin repeat domain

<400> SEQUENCE: 13

Gly Ser Asp Leu Gly Lys Lys Leu Leu Glu Ala Ala Arg Ala Gly Gln
1               5                   10                  15

Asp Asp Glu Val Arg Glu Leu Leu Lys Ala Gly Ala Asp Val Asn Ala
                20                  25                  30

Lys Asp Tyr Phe Ser His Thr Pro Leu His Leu Ala Ala Arg Asn Gly
            35                  40                  45

His Leu Lys Ile Val Glu Val Leu Leu Lys Ala Gly Ala Asp Val Asn
        50                  55                  60

Ala Lys Asp Phe Ala Gly Lys Thr Pro Leu His Leu Ala Ala Asn Asp
65                  70                  75                  80

Gly His Leu Glu Ile Val Glu Val Leu Leu Lys Ala Gly Ala Asp Val
                85                  90                  95

Asn Ala Gln Asp Ile Phe Gly Lys Thr Pro Ala Asp Ile Ala Ala Asp
                100                 105                 110

Ala Gly His Glu Asp Ile Ala Glu Val Leu Gln Lys Ala Ala
            115                 120                 125

<210> SEQ ID NO 14
<211> LENGTH: 126
<212> TYPE: PRT
<213> ORGANISM: Artificial Sequence
<220> FEATURE:
<223> OTHER INFORMATION: Designed ankyrin repeat domain

<400> SEQUENCE: 14

Gly Ser Asp Leu Gly Lys Lys Leu Leu Glu Ala Ala Arg Ala Gly Gln
1               5                   10                  15

Asp Asp Glu Val Arg Glu Leu Leu Lys Ala Gly Ala Asp Val Asn Ala
                20                  25                  30

Lys Asp Tyr Phe Ser His Thr Pro Leu His Leu Ala Ala Arg Asn Gly
            35                  40                  45
```

His Leu Lys Ile Val Glu Val Leu Leu Lys Ala Gly Ala Asp Val Asn
            50                  55                  60

Ala Lys Asp Phe Ala Gly Lys Thr Pro Leu His Leu Ala Ala Asn Glu
65                  70                  75                  80

Gly His Leu Glu Ile Val Glu Val Leu Leu Lys Ala Gly Ala Asp Val
                85                  90                  95

Asn Ala Gln Asp Ile Phe Gly Lys Thr Pro Ala Asp Ile Ala Ala Asp
                100                 105                 110

Ala Gly His Glu Asp Ile Ala Glu Val Leu Gln Lys Ala Ala
            115                 120                 125

<210> SEQ ID NO 15
<211> LENGTH: 126
<212> TYPE: PRT
<213> ORGANISM: Artificial Sequence
<220> FEATURE:
<223> OTHER INFORMATION: Designed ankyrin repeat domain

<400> SEQUENCE: 15

Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
                20                  25                  30

Lys Asp Tyr Phe Ser His Thr Pro Leu His Leu Ala Ala Arg Asn Gly
            35                  40                  45

His Leu Lys Ile Val Glu Val Leu Leu Lys Ala Gly Ala Asp Val Asn
            50                  55                  60

Ala Lys Asp Phe Ala Gly Lys Thr Pro Leu His Leu Ala Ala Asn Asp
65                  70                  75                  80

Gly His Leu Glu Ile Val Glu Val Leu Leu Lys His Gly Ala Asp Val
                85                  90                  95

Asn Ala Gln Asp Ile Phe Gly Lys Thr Pro Ala Asp Ile Ala Ala Asp
                100                 105                 110

Ala Gly His Glu Asp Ile Ala Glu Val Leu Gln Lys Ala Ala
            115                 120                 125

<210> SEQ ID NO 16
<211> LENGTH: 126
<212> TYPE: PRT
<213> ORGANISM: Artificial Sequence
<220> FEATURE:
<223> OTHER INFORMATION: Designed ankyrin repeat domain

<400> SEQUENCE: 16

Gly Ser Asp Leu Gly Ile Lys Leu Leu Phe Ala Ala Lys Gly Gln
1               5                   10                  15

Asp Asp Glu Val Arg Glu Leu Leu Lys Ala Gly Ala Asp Val Asn Ala
                20                  25                  30

Lys Asp Phe Gln Gly Val Thr Pro Leu His Ile Ala Ala Gln Ser Gly
            35                  40                  45

His Leu Glu Ile Val Glu Val Leu Leu Lys Ala Gly Ala Asp Val Asn
            50                  55                  60

Ala Lys Asp Val Thr Gly Asp Thr Pro Leu His Leu Ala Ala Gln His
65                  70                  75                  80

Gly His Leu Glu Ile Val Glu Val Leu Leu Lys Ala Gly Ala Asp Val
                85                  90                  95

Asn Ala Gln Asp Glu Arg Gly Trp Thr Pro Ala Asp Leu Ala Ala Asp
                100                 105                 110

<210> SEQ ID NO 17
<211> LENGTH: 126
<212> TYPE: PRT
<213> ORGANISM: Artificial Sequence
<220> FEATURE:
<223> OTHER INFORMATION: Designed ankyrin repeat domain

<400> SEQUENCE: 17

```
Gly Ser Asp Leu Gly Lys Lys Leu Leu Glu Ala Ala Arg Ala Gly Gln
1               5                   10                  15
Asp Asp Glu Val Arg Glu Leu Leu Lys Ala Gly Ala Asp Val Asn Ala
            20                  25                  30
Lys Asp Glu Tyr Gly Leu Thr Pro Leu Tyr Leu Ala Thr Ala His Gly
        35                  40                  45
His Leu Glu Ile Val Glu Val Leu Leu Lys Ala Gly Ala Asp Val Asn
    50                  55                  60
Ala Val Asp Ala Ile Gly Phe Thr Pro Leu His Leu Ala Ala Phe Ile
65                  70                  75                  80
Gly His Leu Glu Ile Ala Glu Val Leu Leu Lys Ala Gly Ala Asp Val
                85                  90                  95
Asn Ala Gln Asp Lys Phe Gly Lys Thr Pro Ala Asp Ile Ala Ala Gly
            100                 105                 110
Ala Gly Asn Glu Asp Ile Ala Glu Val Leu Gln Lys Ala Ala
        115                 120                 125
```

<210> SEQ ID NO 18
<211> LENGTH: 126
<212> TYPE: PRT
<213> ORGANISM: Artificial Sequence
<220> FEATURE:
<223> OTHER INFORMATION: Designed ankyrin repeat domain

<400> SEQUENCE: 18

```
Gly Ser Asp Leu Gly Val Lys Leu Leu Trp Ala Ala Arg Gly Gly Gln
1               5                   10                  15
Asp Asp Glu Val Arg Glu Leu Leu Lys Ala Gly Ala Asp Val Asn Ala
            20                  25                  30
Lys Asp Phe Gln Gly Ile Thr Pro Leu His Ile Ala Ala Thr Asn Gly
        35                  40                  45
His Leu Glu Ile Val Glu Val Leu Leu Lys Ala Gly Ala Asp Val Asn
    50                  55                  60
Ala Lys Asp Ile Thr Gly Glu Thr Pro Leu His His Ala Ala Asp Ser
65                  70                  75                  80
Gly His Leu Glu Ile Val Glu Val Leu Leu Lys Ala Gly Ala Asp Val
                85                  90                  95
Asn Ala Gln Asp Lys Ala Gly Val Thr Pro Ala Asp Leu Ala Ala Ala
            100                 105                 110
Trp Gly His Glu Asp Ile Ala Glu Val Leu Gln Lys Ala Ala
        115                 120                 125
```

<210> SEQ ID NO 19
<211> LENGTH: 126
<212> TYPE: PRT
<213> ORGANISM: Artificial Sequence
<220> FEATURE:
<223> OTHER INFORMATION: Designed ankyrin repeat domain

<400> SEQUENCE: 19

Gly Ser Asp Leu Gly Val Lys Leu Leu Trp Ala Ala Ala Arg Gly Gln
1               5                   10                  15

Asp Asp Glu Val Arg Ile Leu Ala Ala Gly Ala Asp Val Asn Ala
            20                  25                  30

Lys Asp Phe Gln Gly Ile Thr Pro Leu His Ile Ala Ala Gln Ser Gly
        35                  40                  45

His Leu Glu Ile Val Glu Val Leu Leu Lys Ala Gly Ala Asp Val Asn
    50                  55                  60

Ala Lys Asp Val Thr Gly Asp Thr Pro Leu His Leu Ala Ala Gln His
65                  70                  75                  80

Gly His Leu Val Ile Val Glu Val Leu Leu Lys Ala Gly Ala Asp Val
                85                  90                  95

Asn Ala Gln Asp Glu Arg Gly Trp Thr Pro Ala Asp Leu Ala Ala Asp
            100                 105                 110

Trp Gly His Glu Asp Ile Ala Glu Val Leu Gln Lys Ala Ala
        115                 120                 125

<210> SEQ ID NO 20
<211> LENGTH: 126
<212> TYPE: PRT
<213> ORGANISM: Artificial Sequence
<220> FEATURE:
<223> OTHER INFORMATION: Designed ankyrin repeat domain

<400> SEQUENCE: 20

Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
            20                  25                  30

Lys Asp Glu Tyr Gly Leu Thr Pro Leu Tyr Leu Ala Thr Ala His Gly
        35                  40                  45

His Leu Glu Ile Val Glu Val Leu Leu Lys Asn Gly Ala Asp Val Asn
    50                  55                  60

Ala Val Asp Ala Ile Gly Phe Thr Pro Leu His Leu Ala Ala Phe Ile
65                  70                  75                  80

Gly His Leu Glu Ile Ala Glu Val Leu Leu Lys His Gly Ala Asp Val
                85                  90                  95

Asn Ala Gln Asp Lys Phe Gly Lys Thr Ala Phe Asp Ile Ser Ile Gly
            100                 105                 110

Asn Gly Asn Glu Asp Leu Ala Glu Ile Leu Gln Lys Ala Ala
        115                 120                 125

<210> SEQ ID NO 21
<211> LENGTH: 570
<212> TYPE: PRT
<213> ORGANISM: Artificial Sequence
<220> FEATURE:
<223> OTHER INFORMATION: Protein comprising four designed ankyrin repeat
      domains

<400> SEQUENCE: 21

Gly Ser Asp Leu Gly Lys Lys Leu Leu Glu Ala Ala Arg Ala Gly Gln
1               5                   10                  15

Asp Asp Glu Val Arg Glu Leu Leu Lys Ala Gly Ala Asp Val Asn Ala
            20                  25                  30

Lys Asp Tyr Phe Ser His Thr Pro Leu His Leu Ala Ala Arg Asn Gly

```
                35                  40                  45
His Leu Lys Ile Val Glu Val Leu Lys Ala Gly Ala Asp Val Asn
 50                  55                  60

Ala Lys Asp Phe Ala Gly Lys Thr Pro Leu His Leu Ala Ala Asn Glu
 65                  70                  75                  80

Gly His Leu Glu Ile Val Glu Val Leu Leu Lys Ala Gly Ala Asp Val
                 85                  90                  95

Asn Ala Gln Asp Ile Phe Gly Lys Thr Pro Ala Asp Ile Ala Ala Asp
                100                 105                 110

Ala Gly His Glu Asp Ile Ala Glu Val Leu Gln Lys Ala Ala Gly Ser
                115                 120                 125

Pro Thr Pro Thr Pro Thr Thr Pro Thr Pro Thr Pro Thr Thr Pro Thr
130                 135                 140

Pro Thr Pro Thr Gly Ser Asp Leu Gly Ile Lys Leu Leu Phe Ala Ala
145                 150                 155                 160

Ala Lys Gly Gln Asp Asp Glu Val Arg Glu Leu Leu Lys Ala Gly Ala
                165                 170                 175

Asp Val Asn Ala Lys Asp Phe Gln Gly Val Thr Pro Leu His Ile Ala
                180                 185                 190

Ala Gln Ser Gly His Leu Glu Ile Val Glu Val Leu Leu Lys Ala Gly
                195                 200                 205

Ala Asp Val Asn Ala Lys Asp Val Thr Gly Asp Thr Pro Leu His Leu
210                 215                 220

Ala Ala Gln His Gly His Leu Glu Ile Val Glu Val Leu Leu Lys Ala
225                 230                 235                 240

Gly Ala Asp Val Asn Ala Gln Asp Glu Arg Gly Trp Thr Pro Ala Asp
                245                 250                 255

Leu Ala Ala Asp Trp Gly His Glu Asp Ile Ala Glu Val Leu Gln Lys
                260                 265                 270

Ala Ala Gly Ser Pro Thr Pro Thr Pro Thr Thr Pro Thr Pro Thr Pro
                275                 280                 285

Thr Thr Pro Thr Pro Thr Pro Thr Gly Ser Asp Leu Gly Lys Lys Leu
290                 295                 300

Leu Glu Ala Ala Arg Ala Gly Gln Asp Asp Glu Val Arg Glu Leu Leu
305                 310                 315                 320

Lys Ala Gly Ala Asp Val Asn Ala Lys Asp Glu Tyr Gly Leu Thr Pro
                325                 330                 335

Leu Tyr Leu Ala Thr Ala His Gly His Leu Glu Ile Val Glu Val Leu
                340                 345                 350

Leu Lys Ala Gly Ala Asp Val Asn Ala Val Asp Ala Ile Gly Phe Thr
                355                 360                 365

Pro Leu His Leu Ala Ala Phe Ile Gly His Leu Glu Ile Ala Glu Val
                370                 375                 380

Leu Leu Lys Ala Gly Ala Asp Val Asn Ala Gln Asp Lys Phe Gly Lys
385                 390                 395                 400

Thr Pro Ala Asp Ile Ala Ala Gly Ala Gly Asn Glu Asp Ile Ala Glu
                405                 410                 415

Val Leu Gln Lys Ala Ala Gly Ser Pro Thr Pro Thr Pro Thr Thr Pro
                420                 425                 430

Thr Pro Thr Pro Thr Thr Pro Thr Pro Thr Pro Thr Gly Ser Asp Leu
                435                 440                 445

Gly Lys Lys Leu Leu Glu Ala Ala Arg Ala Gly Gln Asp Asp Glu Val
450                 455                 460
```

Arg Glu Leu Leu Lys Ala Gly Ala Asp Val Asn Ala Lys Asp Tyr Phe
465                 470                 475                 480

Ser His Thr Pro Leu His Leu Ala Ala Arg Asn Gly His Leu Lys Ile
            485                 490                 495

Val Glu Val Leu Leu Lys Ala Gly Ala Asp Val Asn Ala Lys Asp Phe
                500                 505                 510

Ala Gly Lys Thr Pro Leu His Leu Ala Ala Asn Glu Gly His Leu Glu
            515                 520                 525

Ile Val Glu Val Leu Leu Lys Ala Gly Ala Asp Val Asn Ala Gln Asp
        530                 535                 540

Ile Phe Gly Lys Thr Pro Ala Asp Ile Ala Ala Asp Ala Gly His Glu
545                 550                 555                 560

Asp Ile Ala Glu Val Leu Gln Lys Ala Ala
            565                 570

<210> SEQ ID NO 22
<211> LENGTH: 570
<212> TYPE: PRT
<213> ORGANISM: Artificial Sequence
<220> FEATURE:
<223> OTHER INFORMATION: Protein comprising four designed ankyrin repeat
      domains

<400> SEQUENCE: 22

Gly Ser Asp Leu Gly Lys Lys Leu Leu Glu Ala Ala Arg Ala Gly Gln
1               5                   10                  15

Asp Asp Glu Val Arg Glu Leu Leu Lys Ala Gly Ala Asp Val Asn Ala
            20                  25                  30

Lys Asp Tyr Phe Ser His Thr Pro Leu His Leu Ala Ala Arg Asn Gly
        35                  40                  45

His Leu Lys Ile Val Glu Val Leu Leu Lys Ala Gly Ala Asp Val Asn
    50                  55                  60

Ala Lys Asp Phe Ala Gly Lys Thr Pro Leu His Leu Ala Ala Asn Asp
65                  70                  75                  80

Gly His Leu Glu Ile Val Glu Val Leu Leu Lys Ala Gly Ala Asp Val
                85                  90                  95

Asn Ala Gln Asp Ile Phe Gly Lys Thr Pro Ala Asp Ile Ala Ala Asp
            100                 105                 110

Ala Gly His Glu Asp Ile Ala Glu Val Leu Gln Lys Ala Ala Gly Ser
        115                 120                 125

Pro Thr Pro Thr Pro Thr Thr Pro Thr Pro Thr Pro Thr Thr Pro Thr
    130                 135                 140

Pro Thr Pro Thr Gly Ser Asp Leu Gly Ile Lys Leu Leu Phe Ala Ala
145                 150                 155                 160

Ala Lys Gly Gln Asp Asp Glu Val Arg Glu Leu Leu Lys Ala Gly Ala
                165                 170                 175

Asp Val Asn Ala Lys Asp Phe Gln Gly Val Thr Pro Leu His Ile Ala
            180                 185                 190

Ala Gln Ser Gly His Leu Glu Ile Val Glu Val Leu Leu Lys Ala Gly
        195                 200                 205

Ala Asp Val Asn Ala Lys Asp Val Thr Gly Asp Thr Pro Leu His Leu
    210                 215                 220

Ala Ala Gln His Gly His Leu Glu Ile Val Glu Val Leu Leu Lys Ala
225                 230                 235                 240

Gly Ala Asp Val Asn Ala Gln Asp Glu Arg Gly Trp Thr Pro Ala Asp

```
                    245                 250                 255
Leu Ala Ala Asp Trp Gly His Glu Asp Ile Ala Glu Val Leu Gln Lys
            260                 265                 270

Ala Ala Gly Ser Pro Thr Pro Thr Pro Thr Pro Thr Pro Thr Pro
        275                 280                 285

Thr Thr Pro Thr Pro Thr Pro Thr Gly Ser Asp Leu Gly Lys Lys Leu
    290                 295                 300

Leu Glu Ala Ala Arg Ala Gly Gln Asp Glu Val Arg Glu Leu Leu
305                 310                 315                 320

Lys Ala Gly Ala Asp Val Asn Ala Lys Asp Glu Tyr Gly Leu Thr Pro
                325                 330                 335

Leu Tyr Leu Ala Thr Ala His Gly His Leu Glu Ile Val Glu Val Leu
            340                 345                 350

Leu Lys Ala Gly Ala Asp Val Asn Ala Val Asp Ala Ile Gly Phe Thr
        355                 360                 365

Pro Leu His Leu Ala Ala Phe Ile Gly His Leu Glu Ile Ala Glu Val
    370                 375                 380

Leu Leu Lys Ala Gly Ala Asp Val Asn Ala Gln Asp Lys Phe Gly Lys
385                 390                 395                 400

Thr Pro Ala Asp Ile Ala Ala Gly Ala Gly Asn Glu Asp Ile Ala Glu
                405                 410                 415

Val Leu Gln Lys Ala Ala Gly Ser Pro Thr Pro Thr Pro Thr Thr Pro
            420                 425                 430

Thr Pro Thr Pro Thr Thr Pro Thr Pro Thr Pro Thr Gly Ser Asp Leu
        435                 440                 445

Gly Lys Lys Leu Leu Glu Ala Ala Arg Ala Gly Gln Asp Asp Glu Val
    450                 455                 460

Arg Glu Leu Leu Lys Ala Gly Ala Asp Val Asn Ala Lys Asp Tyr Phe
465                 470                 475                 480

Ser His Thr Pro Leu His Leu Ala Ala Arg Asn Gly His Leu Lys Ile
                485                 490                 495

Val Glu Val Leu Leu Lys Ala Gly Ala Asp Val Asn Ala Lys Asp Phe
            500                 505                 510

Ala Gly Lys Thr Pro Leu His Leu Ala Ala Asn Asp Gly His Leu Glu
        515                 520                 525

Ile Val Glu Val Leu Leu Lys Ala Gly Ala Asp Val Asn Ala Gln Asp
    530                 535                 540

Ile Phe Gly Lys Thr Pro Ala Asp Ile Ala Ala Asp Ala Gly His Glu
545                 550                 555                 560

Asp Ile Ala Glu Val Leu Gln Lys Ala Ala
                565                 570

<210> SEQ ID NO 23
<211> LENGTH: 570
<212> TYPE: PRT
<213> ORGANISM: Artificial Sequence
<220> FEATURE:
<223> OTHER INFORMATION: Protein comprising four designed ankyrin repeat
      domains

<400> SEQUENCE: 23

Gly Ser Asp Leu Gly Lys Lys Leu Leu Glu Ala Ala Arg Ala Gly Gln
1               5                   10                  15

Asp Asp Glu Val Arg Glu Leu Leu Lys Ala Gly Ala Asp Val Asn Ala
            20                  25                  30
```

-continued

```
Lys Asp Tyr Phe Ser His Thr Pro Leu His Leu Ala Ala Arg Asn Gly
         35                  40                  45
His Leu Lys Ile Val Glu Val Leu Leu Lys Ala Gly Ala Asp Val Asn
 50                  55                  60
Ala Lys Asp Phe Ala Gly Lys Thr Pro Leu His Leu Ala Ala Asn Glu
 65                  70                  75                  80
Gly His Leu Glu Ile Val Glu Val Leu Leu Lys Ala Gly Ala Asp Val
                 85                  90                  95
Asn Ala Gln Asp Ile Phe Gly Lys Thr Pro Ala Asp Ile Ala Ala Asp
                100                 105                 110
Ala Gly His Glu Asp Ile Ala Glu Val Leu Gln Lys Ala Ala Gly Ser
             115                 120                 125
Pro Thr Pro Thr Pro Thr Thr Pro Thr Pro Thr Thr Pro Thr
         130                 135                 140
Pro Thr Pro Thr Gly Ser Asp Leu Gly Val Lys Leu Leu Trp Ala Ala
145                 150                 155                 160
Ala Arg Gly Gln Asp Asp Glu Val Arg Glu Leu Leu Lys Ala Gly Ala
                165                 170                 175
Asp Val Asn Ala Lys Asp Phe Gln Gly Ile Thr Pro Leu His Ile Ala
                180                 185                 190
Ala Thr Asn Gly His Leu Glu Ile Val Glu Val Leu Leu Lys Ala Gly
             195                 200                 205
Ala Asp Val Asn Ala Lys Asp Ile Thr Gly Glu Thr Pro Leu His His
 210                 215                 220
Ala Ala Asp Ser Gly His Leu Glu Ile Val Glu Val Leu Leu Lys Ala
225                 230                 235                 240
Gly Ala Asp Val Asn Ala Gln Asp Lys Ala Gly Val Thr Pro Ala Asp
                245                 250                 255
Leu Ala Ala Ala Trp Gly His Glu Asp Ile Ala Glu Val Leu Gln Lys
             260                 265                 270
Ala Ala Gly Ser Pro Thr Pro Thr Pro Thr Thr Pro Thr Pro Thr Pro
             275                 280                 285
Thr Thr Pro Thr Pro Thr Pro Thr Gly Ser Asp Leu Gly Lys Lys Leu
         290                 295                 300
Leu Glu Ala Ala Arg Ala Gly Gln Asp Asp Glu Val Arg Glu Leu Leu
305                 310                 315                 320
Lys Ala Gly Ala Asp Val Asn Ala Lys Asp Glu Tyr Gly Leu Thr Pro
                325                 330                 335
Leu Tyr Leu Ala Thr Ala His Gly His Leu Glu Ile Val Glu Val Leu
             340                 345                 350
Leu Lys Ala Gly Ala Asp Val Asn Ala Val Asp Ala Ile Gly Phe Thr
             355                 360                 365
Pro Leu His Leu Ala Ala Phe Ile Gly His Leu Glu Ile Ala Glu Val
         370                 375                 380
Leu Leu Lys Ala Gly Ala Asp Val Asn Ala Gln Asp Lys Phe Gly Lys
385                 390                 395                 400
Thr Pro Ala Asp Ile Ala Ala Gly Ala Gly Asn Glu Asp Ile Ala Glu
                405                 410                 415
Val Leu Gln Lys Ala Ala Gly Ser Pro Thr Pro Thr Pro Thr Thr Pro
             420                 425                 430
Thr Pro Thr Pro Thr Thr Pro Thr Pro Thr Thr Gly Ser Asp Leu
         435                 440                 445
Gly Lys Lys Leu Leu Glu Ala Ala Arg Ala Gly Gln Asp Asp Glu Val
```

```
                 450                 455                 460

Arg Glu Leu Leu Lys Ala Gly Ala Asp Val Asn Ala Lys Asp Tyr Phe
465                 470                 475                 480

Ser His Thr Pro Leu His Leu Ala Ala Arg Asn Gly His Leu Lys Ile
                485                 490                 495

Val Glu Val Leu Leu Lys Ala Gly Ala Asp Val Asn Ala Lys Asp Phe
                500                 505                 510

Ala Gly Lys Thr Pro Leu His Leu Ala Ala Asn Glu Gly His Leu Glu
        515                 520                 525

Ile Val Glu Val Leu Leu Lys Ala Gly Ala Asp Val Asn Ala Gln Asp
        530                 535                 540

Ile Phe Gly Lys Thr Pro Ala Asp Ile Ala Ala Asp Ala Gly His Glu
545                 550                 555                 560

Asp Ile Ala Glu Val Leu Gln Lys Ala Ala
                565                 570

<210> SEQ ID NO 24
<211> LENGTH: 570
<212> TYPE: PRT
<213> ORGANISM: Artificial Sequence
<220> FEATURE:
<223> OTHER INFORMATION: Protein comprising four designed ankyrin repeat
      domains

<400> SEQUENCE: 24

Gly Ser Asp Leu Gly Lys Lys Leu Leu Glu Ala Ala Arg Ala Gly Gln
1               5                   10                  15

Asp Asp Glu Val Arg Glu Leu Leu Lys Ala Gly Ala Asp Val Asn Ala
                20                  25                  30

Lys Asp Tyr Phe Ser His Thr Pro Leu His Leu Ala Ala Arg Asn Gly
            35                  40                  45

His Leu Lys Ile Val Glu Val Leu Leu Lys Ala Gly Ala Asp Val Asn
        50                  55                  60

Ala Lys Asp Phe Ala Gly Lys Thr Pro Leu His Leu Ala Ala Asn Glu
65                  70                  75                  80

Gly His Leu Glu Ile Val Glu Val Leu Leu Lys Ala Gly Ala Asp Val
                85                  90                  95

Asn Ala Gln Asp Ile Phe Gly Lys Thr Pro Ala Asp Ile Ala Ala Asp
                100                 105                 110

Ala Gly His Glu Asp Ile Ala Glu Val Leu Gln Lys Ala Ala Gly Ser
            115                 120                 125

Pro Thr Pro Thr Pro Thr Thr Pro Thr Pro Thr Pro Thr Thr Pro Thr
        130                 135                 140

Pro Thr Pro Thr Gly Ser Asp Leu Gly Lys Lys Leu Leu Glu Ala Ala
145                 150                 155                 160

Arg Ala Gly Gln Asp Asp Glu Val Arg Glu Leu Leu Lys Ala Gly Ala
                165                 170                 175

Asp Val Asn Ala Lys Asp Tyr Phe Ser His Thr Pro Leu His Leu Ala
            180                 185                 190

Ala Arg Asn Gly His Leu Lys Ile Val Glu Val Leu Leu Lys Ala Gly
        195                 200                 205

Ala Asp Val Asn Ala Lys Asp Phe Ala Gly Lys Thr Pro Leu His Leu
        210                 215                 220

Ala Ala Asn Glu Gly His Leu Glu Ile Val Glu Val Leu Leu Lys Ala
225                 230                 235                 240
```

```
Gly Ala Asp Val Asn Ala Gln Asp Ile Phe Gly Lys Thr Pro Ala Asp
                245                 250                 255
Ile Ala Ala Asp Ala Gly His Glu Asp Ile Ala Glu Val Leu Gln Lys
            260                 265                 270
Ala Ala Gly Ser Pro Thr Pro Thr Pro Thr Thr Pro Thr Pro Thr Pro
        275                 280                 285
Thr Thr Pro Thr Pro Thr Pro Thr Gly Ser Asp Leu Gly Ile Lys Leu
    290                 295                 300
Leu Phe Ala Ala Ala Lys Gly Gln Asp Asp Glu Val Arg Glu Leu Leu
305                 310                 315                 320
Lys Ala Gly Ala Asp Val Asn Ala Lys Asp Phe Gln Gly Val Thr Pro
                325                 330                 335
Leu His Ile Ala Ala Gln Ser Gly His Leu Glu Ile Val Glu Val Leu
            340                 345                 350
Leu Lys Ala Gly Ala Asp Val Asn Ala Lys Asp Val Thr Gly Asp Thr
        355                 360                 365
Pro Leu His Leu Ala Ala Gln His Gly His Leu Glu Ile Val Glu Val
    370                 375                 380
Leu Leu Lys Ala Gly Ala Asp Val Asn Ala Gln Asp Glu Arg Gly Trp
385                 390                 395                 400
Thr Pro Ala Asp Leu Ala Ala Asp Trp Gly His Glu Asp Ile Ala Glu
                405                 410                 415
Val Leu Gln Lys Ala Ala Gly Ser Pro Thr Pro Thr Pro Thr Thr Pro
            420                 425                 430
Thr Pro Thr Pro Thr Thr Pro Thr Pro Thr Gly Ser Asp Leu
        435                 440                 445
Gly Lys Lys Leu Leu Glu Ala Ala Arg Ala Gly Gln Asp Asp Glu Val
    450                 455                 460
Arg Glu Leu Leu Lys Ala Gly Ala Asp Val Asn Ala Lys Asp Glu Tyr
465                 470                 475                 480
Gly Leu Thr Pro Leu Tyr Leu Ala Thr Ala His Gly His Leu Glu Ile
                485                 490                 495
Val Glu Val Leu Leu Lys Ala Gly Ala Asp Val Asn Ala Val Asp Ala
            500                 505                 510
Ile Gly Phe Thr Pro Leu His Leu Ala Ala Phe Ile Gly His Leu Glu
        515                 520                 525
Ile Ala Glu Val Leu Leu Lys Ala Gly Ala Asp Val Asn Ala Gln Asp
    530                 535                 540
Lys Phe Gly Lys Thr Pro Ala Asp Ile Ala Ala Gly Ala Gly Asn Glu
545                 550                 555                 560
Asp Ile Ala Glu Val Leu Gln Lys Ala Ala
                565                 570

<210> SEQ ID NO 25
<211> LENGTH: 570
<212> TYPE: PRT
<213> ORGANISM: Artificial Sequence
<220> FEATURE:
<223> OTHER INFORMATION: Protein comprising four designed ankyrin repeat
      domains

<400> SEQUENCE: 25

Gly Ser Asp Leu Gly Lys Lys Leu Leu Glu Ala Ala Arg Ala Gly Gln
1               5                   10                  15
Asp Asp Glu Val Arg Glu Leu Leu Lys Ala Gly Ala Asp Val Asn Ala
            20                  25                  30
```

```
Lys Asp Tyr Phe Ser His Thr Pro Leu His Leu Ala Ala Arg Asn Gly
             35                  40                  45

His Leu Lys Ile Val Glu Val Leu Leu Lys Ala Gly Ala Asp Val Asn
 50                  55                  60

Ala Lys Asp Phe Ala Gly Lys Thr Pro Leu His Leu Ala Ala Asn Glu
 65                  70                  75                  80

Gly His Leu Glu Ile Val Glu Val Leu Leu Lys Ala Gly Ala Asp Val
                 85                  90                  95

Asn Ala Gln Asp Ile Phe Gly Lys Thr Pro Ala Asp Ile Ala Ala Asp
             100                 105                 110

Ala Gly His Glu Asp Ile Ala Glu Val Leu Gln Lys Ala Gly Ser
             115                 120                 125

Pro Thr Pro Thr Pro Thr Thr Pro Thr Pro Thr Pro Thr Thr Pro Thr
130                 135                 140

Pro Thr Pro Thr Gly Ser Asp Leu Gly Lys Lys Leu Leu Glu Ala Ala
145                 150                 155                 160

Arg Ala Gly Gln Asp Asp Glu Val Arg Glu Leu Leu Lys Ala Gly Ala
                 165                 170                 175

Asp Val Asn Ala Lys Asp Tyr Phe Ser His Thr Pro Leu His Leu Ala
             180                 185                 190

Ala Arg Asn Gly His Leu Lys Ile Val Glu Val Leu Leu Lys Ala Gly
             195                 200                 205

Ala Asp Val Asn Ala Lys Asp Phe Ala Gly Lys Thr Pro Leu His Leu
             210                 215                 220

Ala Ala Asn Glu Gly His Leu Glu Ile Val Glu Val Leu Leu Lys Ala
225                 230                 235                 240

Gly Ala Asp Val Asn Ala Gln Asp Ile Phe Gly Lys Thr Pro Ala Asp
                 245                 250                 255

Ile Ala Ala Asp Ala Gly His Glu Asp Ile Ala Glu Val Leu Gln Lys
             260                 265                 270

Ala Ala Gly Ser Pro Thr Pro Thr Pro Thr Thr Pro Thr Pro Thr Pro
             275                 280                 285

Thr Thr Pro Thr Pro Thr Pro Thr Gly Ser Asp Leu Gly Val Lys Leu
290                 295                 300

Leu Trp Ala Ala Ala Arg Gly Gln Asp Asp Glu Val Arg Glu Leu Leu
305                 310                 315                 320

Lys Ala Gly Ala Asp Val Asn Ala Lys Asp Phe Gln Gly Ile Thr Pro
                 325                 330                 335

Leu His Ile Ala Ala Thr Asn Gly His Leu Glu Ile Val Glu Val Leu
             340                 345                 350

Leu Lys Ala Gly Ala Asp Val Asn Ala Lys Asp Ile Thr Gly Glu Thr
             355                 360                 365

Pro Leu His His Ala Ala Asp Ser Gly His Leu Glu Ile Val Glu Val
370                 375                 380

Leu Leu Lys Ala Gly Ala Asp Val Asn Ala Gln Asp Lys Ala Gly Val
385                 390                 395                 400

Thr Pro Ala Asp Leu Ala Ala Ala Trp Gly His Glu Asp Ile Ala Glu
                 405                 410                 415

Val Leu Gln Lys Ala Ala Gly Ser Pro Thr Pro Thr Pro Thr Thr Pro
             420                 425                 430

Thr Pro Thr Pro Thr Thr Pro Thr Pro Thr Pro Thr Gly Ser Asp Leu
             435                 440                 445
```

```
Gly Lys Lys Leu Leu Glu Ala Ala Arg Ala Gly Gln Asp Asp Glu Val
450                 455                 460
Arg Glu Leu Leu Lys Ala Gly Ala Asp Val Asn Ala Lys Asp Glu Tyr
465                 470                 475                 480
Gly Leu Thr Pro Leu Tyr Leu Ala Thr Ala His Gly His Leu Glu Ile
                485                 490                 495
Val Glu Val Leu Leu Lys Ala Gly Ala Asp Val Asn Ala Val Asp Ala
                500                 505                 510
Ile Gly Phe Thr Pro Leu His Leu Ala Ala Phe Ile Gly His Leu Glu
            515                 520                 525
Ile Ala Glu Val Leu Leu Lys Ala Gly Ala Asp Val Asn Ala Gln Asp
530                 535                 540
Lys Phe Gly Lys Thr Pro Ala Asp Ile Ala Ala Gly Ala Gly Asn Glu
545                 550                 555                 560
Asp Ile Ala Glu Val Leu Gln Lys Ala Ala
                565                 570

<210> SEQ ID NO 26
<211> LENGTH: 562
<212> TYPE: PRT
<213> ORGANISM: Artificial Sequence
<220> FEATURE:
<223> OTHER INFORMATION: Protein comprising four designed ankyrin repeat
      domains

<400> SEQUENCE: 26

Gly Ser Asp Leu Gly Lys Lys Leu Leu Glu Ala Ala Arg Ala Gly Gln
1               5                   10                  15
Asp Asp Glu Val Arg Ile Leu Met Ala Asn Gly Ala Asp Val Asn Ala
                20                  25                  30
Lys Asp Tyr Phe Ser His Thr Pro Leu His Leu Ala Ala Arg Asn Gly
            35                  40                  45
His Leu Lys Ile Val Glu Val Leu Leu Lys Ala Gly Ala Asp Val Asn
        50                  55                  60
Ala Lys Asp Phe Ala Gly Lys Thr Pro Leu His Leu Ala Ala Asn Asp
65                  70                  75                  80
Gly His Leu Glu Ile Val Glu Val Leu Leu Lys His Gly Ala Asp Val
                85                  90                  95
Asn Ala Gln Asp Ile Phe Gly Lys Thr Pro Ala Asp Ile Ala Ala Asp
                100                 105                 110
Ala Gly His Glu Asp Ile Ala Glu Val Leu Gln Lys Ala Ala Gly Gly
            115                 120                 125
Gly Gly Ser Gly Gly Gly Ser Gly Gly Gly Ser Gly Gly Gly
        130                 135                 140
Gly Ser Gly Ser Asp Leu Gly Ala Lys Leu Leu Ser Asp Leu Gly Val
145                 150                 155                 160
Lys Leu Leu Trp Ala Ala Ala Arg Gly Gln Asp Asp Glu Val Arg Ile
                165                 170                 175
Leu Leu Ala Ala Gly Ala Asp Val Asn Ala Lys Asp Phe Gln Gly Ile
            180                 185                 190
Thr Pro Leu His Ile Ala Ala Gln Ser Gly His Leu Glu Ile Val Glu
        195                 200                 205
Val Leu Leu Lys Ala Gly Ala Asp Val Asn Ala Lys Asp Val Thr Gly
    210                 215                 220
Asp Thr Pro Leu His Leu Ala Ala Gln His Gly His Leu Val Ile Val
225                 230                 235                 240
```

```
Glu Val Leu Leu Lys Ala Gly Ala Asp Val Asn Ala Gln Asp Glu Arg
                245                 250                 255

Gly Trp Thr Pro Ala Asp Leu Ala Ala Asp Trp Gly His Glu Asp Ile
                260                 265                 270

Ala Glu Val Leu Gln Lys Ala Ala Gly Gly Gly Ser Gly Gly Gly
                275                 280                 285

Gly Ser Gly Ser Asp Leu Gly Lys Lys Leu Leu Glu Ala Ala Arg Ala
            290                 295                 300

Gly Gln Asp Asp Glu Val Arg Ile Leu Met Ala Asn Gly Ala Asp Val
305                 310                 315                 320

Asn Ala Lys Asp Glu Tyr Gly Leu Thr Pro Leu Tyr Leu Ala Thr Ala
                325                 330                 335

His Gly His Leu Glu Ile Val Glu Val Leu Leu Lys Asn Gly Ala Asp
                340                 345                 350

Val Asn Ala Val Asp Ala Ile Gly Phe Thr Pro Leu His Leu Ala Ala
                355                 360                 365

Phe Ile Gly His Leu Glu Ile Ala Glu Val Leu Leu Lys His Gly Ala
            370                 375                 380

Asp Val Asn Ala Gln Asp Lys Phe Gly Lys Thr Ala Phe Asp Ile Ser
385                 390                 395                 400

Ile Gly Asn Gly Asn Glu Asp Leu Ala Glu Ile Leu Gln Lys Ala Ala
                405                 410                 415

Gly Gly Gly Gly Ser Gly Gly Gly Ser Gly Gly Gly Ser Gly
                420                 425                 430

Gly Gly Ser Gly Ser Asp Leu Gly Lys Lys Leu Leu Glu Ala Ala
            435                 440                 445

Arg Ala Gly Gln Asp Asp Glu Val Arg Ile Leu Met Ala Asn Gly Ala
450                 455                 460

Asp Val Asn Ala Lys Asp Tyr Phe Ser His Thr Pro Leu His Leu Ala
465                 470                 475                 480

Ala Arg Asn Gly His Leu Lys Ile Val Glu Val Leu Leu Lys Ala Gly
                485                 490                 495

Ala Asp Val Asn Ala Lys Asp Phe Ala Gly Lys Thr Pro Leu His Leu
                500                 505                 510

Ala Ala Asn Asp Gly His Leu Glu Ile Val Glu Val Leu Leu Lys His
                515                 520                 525

Gly Ala Asp Val Asn Ala Gln Asp Ile Phe Gly Lys Thr Pro Ala Asp
            530                 535                 540

Ile Ala Ala Asp Ala Gly His Glu Asp Ile Ala Glu Val Leu Gln Lys
545                 550                 555                 560

Ala Ala

<210> SEQ ID NO 27
<211> LENGTH: 578
<212> TYPE: PRT
<213> ORGANISM: Artificial Sequence
<220> FEATURE:
<223> OTHER INFORMATION: Protein comprising four designed ankyrin repeat
      domains

<400> SEQUENCE: 27

Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
                20                  25                  30
```

```
Lys Asp Tyr Phe Ser His Thr Pro Leu His Leu Ala Ala Arg Asn Gly
         35                  40                  45

His Leu Lys Ile Val Glu Val Leu Leu Lys Ala Gly Ala Asp Val Asn
 50                  55                  60

Ala Lys Asp Phe Ala Gly Lys Thr Pro Leu His Leu Ala Ala Asn Asp
 65                  70                  75                  80

Gly His Leu Glu Ile Val Glu Val Leu Leu Lys His Gly Ala Asp Val
                 85                  90                  95

Asn Ala Gln Asp Ile Phe Gly Lys Thr Pro Ala Asp Ile Ala Ala Asp
                100                 105                 110

Ala Gly His Glu Asp Ile Ala Glu Val Leu Gln Lys Ala Gly Ser
                115                 120                 125

Pro Thr Pro Thr Pro Thr Thr Pro Thr Pro Thr Pro Thr Thr Pro Thr
        130                 135                 140

Pro Thr Pro Thr Gly Ser Asp Leu Gly Ala Lys Leu Leu Ser Asp Leu
145                 150                 155                 160

Gly Val Lys Leu Leu Trp Ala Ala Ala Arg Gly Gln Asp Asp Glu Val
                165                 170                 175

Arg Ile Leu Leu Ala Ala Gly Ala Asp Val Asn Ala Lys Asp Phe Gln
                180                 185                 190

Gly Ile Thr Pro Leu His Ile Ala Ala Gln Ser Gly His Leu Glu Ile
                195                 200                 205

Val Glu Val Leu Leu Lys Ala Gly Ala Asp Val Asn Ala Lys Asp Val
        210                 215                 220

Thr Gly Asp Thr Pro Leu His Leu Ala Ala Gln His Gly His Leu Val
225                 230                 235                 240

Ile Val Glu Val Leu Leu Lys Ala Gly Ala Asp Val Asn Ala Gln Asp
                245                 250                 255

Glu Arg Gly Trp Thr Pro Ala Asp Leu Ala Ala Asp Trp Gly His Glu
                260                 265                 270

Asp Ile Ala Glu Val Leu Gln Lys Ala Ala Gly Ser Pro Thr Pro Thr
                275                 280                 285

Pro Thr Thr Pro Thr Pro Thr Pro Thr Thr Pro Thr Pro Thr Pro Thr
        290                 295                 300

Gly Ser Asp Leu Gly Lys Lys Leu Leu Glu Ala Ala Arg Ala Gly Gln
305                 310                 315                 320

Asp Asp Glu Val Arg Ile Leu Met Ala Asn Gly Ala Asp Val Asn Ala
                325                 330                 335

Lys Asp Glu Tyr Gly Leu Thr Pro Leu Tyr Leu Ala Thr Ala His Gly
                340                 345                 350

His Leu Glu Ile Val Glu Val Leu Leu Lys Asn Gly Ala Asp Val Asn
                355                 360                 365

Ala Val Asp Ala Ile Gly Phe Thr Pro Leu His Leu Ala Ala Phe Ile
370                 375                 380

Gly His Leu Glu Ile Ala Glu Val Leu Leu Lys His Gly Ala Asp Val
385                 390                 395                 400

Asn Ala Gln Asp Lys Phe Gly Lys Thr Ala Phe Asp Ile Ser Ile Gly
                405                 410                 415

Asn Gly Asn Glu Asp Leu Ala Glu Ile Leu Gln Lys Ala Ala Gly Ser
                420                 425                 430

Pro Thr Pro Thr Pro Thr Thr Pro Thr Pro Thr Pro Thr Thr Pro Thr
        435                 440                 445
```

```
Pro Thr Pro Thr Gly Ser Asp Leu Gly Lys Lys Leu Leu Glu Ala Ala
    450                 455                 460

Arg Ala Gly Gln Asp Asp Glu Val Arg Ile Leu Met Ala Asn Gly Ala
465                 470                 475                 480

Asp Val Asn Ala Lys Asp Tyr Phe Ser His Thr Pro Leu His Leu Ala
                485                 490                 495

Ala Arg Asn Gly His Leu Lys Ile Val Glu Val Leu Leu Lys Ala Gly
            500                 505                 510

Ala Asp Val Asn Ala Lys Asp Phe Ala Gly Lys Thr Pro Leu His Leu
        515                 520                 525

Ala Ala Asn Asp Gly His Leu Glu Ile Val Glu Val Leu Leu Lys His
530                 535                 540

Gly Ala Asp Val Asn Ala Gln Asp Ile Phe Gly Lys Thr Pro Ala Asp
545                 550                 555                 560

Ile Ala Ala Asp Ala Gly His Glu Asp Ile Ala Glu Val Leu Gln Lys
                565                 570                 575

Ala Ala

<210> SEQ ID NO 28
<211> LENGTH: 283
<212> TYPE: PRT
<213> ORGANISM: Artificial Sequence
<220> FEATURE:
<223> OTHER INFORMATION: Protein comprising two designed ankyrin repeat
      domains

<400> SEQUENCE: 28

Gly Ser Asp Leu Gly Ile Lys Leu Leu Phe Ala Ala Lys Gly Gln
1               5                   10                  15

Asp Asp Glu Val Arg Glu Leu Leu Lys Ala Gly Ala Asp Val Asn Ala
            20                  25                  30

Lys Asp Phe Gln Gly Val Thr Pro Leu His Ile Ala Ala Gln Ser Gly
        35                  40                  45

His Leu Glu Ile Val Glu Val Leu Leu Lys Ala Gly Ala Asp Val Asn
    50                  55                  60

Ala Lys Asp Val Thr Gly Asp Thr Pro Leu His Leu Ala Ala Gln His
65                  70                  75                  80

Gly His Leu Glu Ile Val Glu Val Leu Leu Lys Ala Gly Ala Asp Val
                85                  90                  95

Asn Ala Gln Asp Glu Arg Gly Trp Thr Pro Ala Asp Leu Ala Ala Asp
            100                 105                 110

Trp Gly His Glu Asp Ile Ala Glu Val Leu Gln Lys Ala Ala Gly Ser
        115                 120                 125

Pro Thr Pro Thr Pro Thr Thr Pro Thr Pro Thr Pro Thr Thr Pro Thr
    130                 135                 140

Pro Thr Pro Thr Gly Ser Asp Leu Gly Lys Lys Leu Leu Glu Ala Ala
145                 150                 155                 160

Arg Ala Gly Gln Asp Asp Glu Val Arg Glu Leu Leu Lys Ala Gly Ala
                165                 170                 175

Asp Val Asn Ala Lys Asp Glu Tyr Gly Leu Thr Pro Leu Tyr Leu Ala
            180                 185                 190

Thr Ala His Gly His Leu Glu Ile Val Glu Val Leu Leu Lys Ala Gly
        195                 200                 205

Ala Asp Val Asn Ala Val Asp Ala Ile Gly Phe Thr Pro Leu His Leu
    210                 215                 220
```

```
Ala Ala Phe Ile Gly His Leu Glu Ile Ala Glu Val Leu Leu Lys Ala
225                 230                 235                 240

Gly Ala Asp Val Asn Ala Gln Asp Lys Phe Gly Lys Thr Pro Ala Asp
            245                 250                 255

Ile Ala Ala Gly Ala Gly Asn Glu Asp Ile Ala Glu Val Leu Gln Lys
        260                 265                 270

Ala Ala Gly Gly Gly Ser Gly Gly Gly Ser Cys
        275                 280
```

<210> SEQ ID NO 29
<211> LENGTH: 414
<212> TYPE: PRT
<213> ORGANISM: Artificial Sequence
<220> FEATURE:
<223> OTHER INFORMATION: Protein comprising three designed ankyrin
      repeat domains

<400> SEQUENCE: 29

```
Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
            20                  25                  30

Lys Asp Tyr Phe Ser His Thr Pro Leu His Leu Ala Ala Arg Asn Gly
        35                  40                  45

His Leu Lys Ile Val Glu Val Leu Leu Lys Ala Gly Ala Asp Val Asn
50                  55                  60

Ala Lys Asp Phe Ala Gly Lys Thr Pro Leu His Leu Ala Ala Asn Asp
65                  70                  75                  80

Gly His Leu Glu Ile Val Glu Val Leu Leu Lys His Gly Ala Asp Val
                85                  90                  95

Asn Ala Gln Asp Ile Phe Gly Lys Thr Pro Ala Asp Ile Ala Ala Asp
            100                 105                 110

Ala Gly His Glu Asp Ile Ala Glu Val Leu Gln Lys Leu Gly Gly Gly
        115                 120                 125

Gly Ser Gly Gly Gly Ser Gly Gly Gly Ser Gly Gly Gly Gly
        130                 135                 140

Ser Arg Ser Asp Leu Gly Ala Lys Leu Leu Ser Asp Leu Gly Val Lys
145                 150                 155                 160

Leu Leu Trp Ala Ala Arg Gly Gln Asp Asp Glu Val Arg Ile Leu
                165                 170                 175

Leu Ala Ala Gly Ala Asp Val Asn Ala Lys Asp Phe Gln Gly Ile Thr
            180                 185                 190

Pro Leu His Ile Ala Ala Gln Ser Gly His Leu Glu Ile Val Glu Val
        195                 200                 205

Leu Leu Lys Ala Gly Ala Asp Val Asn Ala Lys Asp Val Thr Gly Asp
        210                 215                 220

Thr Pro Leu His Leu Ala Ala Gln His Gly His Leu Val Ile Val Glu
225                 230                 235                 240

Val Leu Leu Lys Ala Gly Ala Asp Val Asn Ala Gln Asp Glu Arg Gly
                245                 250                 255

Trp Thr Pro Ala Asp Leu Ala Ala Asp Trp Gly His Glu Asp Ile Ala
            260                 265                 270

Glu Val Leu Gln Lys Leu Gly Gly Gly Ser Gly Gly Gly Ser
        275                 280                 285

Arg Ser Asp Leu Gly Lys Lys Leu Leu Glu Ala Ala Arg Ala Gly Gln
290                 295                 300
```

```
Asp Asp Glu Val Arg Ile Leu Met Ala Asn Gly Ala Asp Val Asn Ala
305                 310                 315                 320

Lys Asp Glu Tyr Gly Leu Thr Pro Leu Tyr Leu Ala Thr Ala His Gly
            325                 330                 335

His Leu Glu Ile Val Glu Val Leu Leu Lys Asn Gly Ala Asp Val Asn
        340                 345                 350

Ala Val Asp Ala Ile Gly Phe Thr Pro Leu His Leu Ala Ala Phe Ile
    355                 360                 365

Gly His Leu Glu Ile Ala Glu Val Leu Leu Lys His Gly Ala Asp Val
370                 375                 380

Asn Ala Gln Asp Lys Phe Gly Lys Thr Ala Phe Asp Ile Ser Ile Gly
385                 390                 395                 400

Asn Gly Asn Glu Asp Leu Ala Glu Ile Leu Gln Lys Leu Asn
            405                 410
```

<210> SEQ ID NO 30
<211> LENGTH: 562
<212> TYPE: PRT
<213> ORGANISM: Artificial Sequence
<220> FEATURE:
<223> OTHER INFORMATION: Protein comprising four designed ankyrin repeat
      domains

<400> SEQUENCE: 30

```
Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
            20                  25                  30

Lys Asp Tyr Phe Ser His Thr Pro Leu His Leu Ala Ala Arg Asn Gly
        35                  40                  45

His Leu Lys Ile Val Glu Val Leu Leu Lys Ala Gly Ala Asp Val Asn
    50                  55                  60

Ala Lys Asp Phe Ala Gly Lys Thr Pro Leu His Leu Ala Ala Asn Asp
65                  70                  75                  80

Gly His Leu Glu Ile Val Glu Val Leu Leu Lys His Gly Ala Asp Val
                85                  90                  95

Asn Ala Gln Asp Ile Phe Gly Lys Thr Pro Ala Asp Ile Ala Ala Asp
            100                 105                 110

Ala Gly His Glu Asp Ile Ala Glu Val Leu Gln Lys Ala Ala Gly Gly
        115                 120                 125

Gly Gly Ser Gly Gly Gly Ser Gly Gly Gly Ser Gly Gly Gly
    130                 135                 140

Gly Ser Gly Ser Asp Leu Gly Lys Lys Leu Leu Glu Ala Ala Arg Ala
145                 150                 155                 160

Gly Gln Asp Asp Glu Val Arg Ile Leu Met Ala Asn Gly Ala Asp Val
                165                 170                 175

Asn Ala Lys Asp Tyr Phe Ser His Thr Pro Leu His Leu Ala Ala Arg
            180                 185                 190

Asn Gly His Leu Lys Ile Val Glu Val Leu Leu Lys Ala Gly Ala Asp
        195                 200                 205

Val Asn Ala Lys Asp Phe Ala Gly Lys Thr Pro Leu His Leu Ala Ala
    210                 215                 220

Asn Asp Gly His Leu Glu Ile Val Glu Val Leu Leu Lys His Gly Ala
225                 230                 235                 240

Asp Val Asn Ala Gln Asp Ile Phe Gly Lys Thr Pro Ala Asp Ile Ala
```

```
                245                 250                 255
Ala Asp Ala Gly His Glu Asp Ile Ala Glu Val Leu Gln Lys Ala Ala
            260                 265                 270

Gly Gly Gly Gly Ser Gly Gly Gly Gly Ser Gly Gly Gly Gly Ser Gly
        275                 280                 285

Gly Gly Gly Ser Gly Ser Asp Leu Gly Ala Lys Leu Leu Ser Asp Leu
        290                 295                 300

Gly Val Lys Leu Leu Trp Ala Ala Arg Gly Gln Asp Asp Glu Val
305                 310                 315                 320

Arg Ile Leu Leu Ala Ala Gly Ala Asp Val Asn Ala Lys Asp Phe Gln
                325                 330                 335

Gly Ile Thr Pro Leu His Ile Ala Ala Gln Ser Gly His Leu Glu Ile
                340                 345                 350

Val Glu Val Leu Leu Lys Ala Gly Ala Asp Val Asn Ala Lys Asp Val
                355                 360                 365

Thr Gly Asp Thr Pro Leu His Leu Ala Ala Gln His Gly His Leu Val
            370                 375                 380

Ile Val Glu Val Leu Leu Lys Ala Gly Ala Asp Val Asn Ala Gln Asp
385                 390                 395                 400

Glu Arg Gly Trp Thr Pro Ala Asp Leu Ala Ala Asp Trp Gly His Glu
                405                 410                 415

Asp Ile Ala Glu Val Leu Gln Lys Ala Ala Gly Gly Gly Gly Ser Gly
                420                 425                 430

Gly Gly Gly Ser Gly Ser Asp Leu Gly Lys Lys Leu Leu Glu Ala Ala
            435                 440                 445

Arg Ala Gly Gln Asp Asp Glu Val Arg Ile Leu Met Ala Asn Gly Ala
        450                 455                 460

Asp Val Asn Ala Lys Asp Glu Tyr Gly Leu Thr Pro Leu Tyr Leu Ala
465                 470                 475                 480

Thr Ala His Gly His Leu Glu Ile Val Glu Val Leu Leu Lys Asn Gly
            485                 490                 495

Ala Asp Val Asn Ala Val Asp Ala Ile Gly Phe Thr Pro Leu His Leu
                500                 505                 510

Ala Ala Phe Ile Gly His Leu Glu Ile Ala Glu Val Leu Leu Lys His
            515                 520                 525

Gly Ala Asp Val Asn Ala Gln Asp Lys Phe Gly Lys Thr Ala Phe Asp
        530                 535                 540

Ile Ser Ile Gly Asn Gly Asn Glu Asp Leu Ala Glu Ile Leu Gln Lys
545                 550                 555                 560

Ala Ala

<210> SEQ ID NO 31
<211> LENGTH: 580
<212> TYPE: PRT
<213> ORGANISM: Artificial Sequence
<220> FEATURE:
<223> OTHER INFORMATION: Protein comprising four designed ankyrin repeat
      domains

<400> SEQUENCE: 31

Met Arg Gly Ser His His His His His His Gly Ser Asp Leu Gly Lys
1               5                   10                  15

Lys Leu Leu Glu Ala Ala Arg Ala Gly Gln Asp Asp Glu Val Arg Glu
            20                  25                  30

Leu Leu Lys Ala Gly Ala Asp Val Asn Ala Lys Asp Tyr Phe Ser His
```

```
                35                  40                  45
Thr Pro Leu His Leu Ala Ala Arg Asn Gly His Leu Lys Ile Val Glu
 50                  55                  60

Val Leu Leu Lys Ala Gly Ala Asp Val Asn Ala Lys Asp Phe Ala Gly
 65                  70                  75                  80

Lys Thr Pro Leu His Leu Ala Ala Asn Glu Gly His Leu Glu Ile Val
                 85                  90                  95

Glu Val Leu Leu Lys Ala Gly Ala Asp Val Asn Ala Gln Asp Ile Phe
                100                 105                 110

Gly Lys Thr Pro Ala Asp Ile Ala Ala Asp Ala Gly His Glu Asp Ile
                115                 120                 125

Ala Glu Val Leu Gln Lys Ala Ala Gly Ser Pro Thr Pro Thr Pro Thr
            130                 135                 140

Thr Pro Thr Pro Thr Pro Thr Thr Pro Thr Pro Thr Pro Thr Gly Ser
145                 150                 155                 160

Asp Leu Gly Ile Lys Leu Leu Phe Ala Ala Lys Gly Gln Asp Asp
                165                 170                 175

Glu Val Arg Glu Leu Leu Lys Ala Gly Ala Asp Val Asn Ala Lys Asp
                180                 185                 190

Phe Gln Gly Val Thr Pro Leu His Ile Ala Ala Gln Ser Gly His Leu
            195                 200                 205

Glu Ile Val Glu Val Leu Leu Lys Ala Gly Ala Asp Val Asn Ala Lys
210                 215                 220

Asp Val Thr Gly Asp Thr Pro Leu His Leu Ala Ala Gln His Gly His
225                 230                 235                 240

Leu Glu Ile Val Glu Val Leu Leu Lys Ala Gly Ala Asp Val Asn Ala
                245                 250                 255

Gln Asp Glu Arg Gly Trp Thr Pro Ala Asp Leu Ala Ala Asp Trp Gly
            260                 265                 270

His Glu Asp Ile Ala Glu Val Leu Gln Lys Ala Ala Gly Ser Pro Thr
        275                 280                 285

Pro Thr Pro Thr Thr Pro Thr Pro Thr Pro Thr Thr Pro Thr Pro Thr
290                 295                 300

Pro Thr Gly Ser Asp Leu Gly Lys Lys Leu Leu Glu Ala Ala Arg Ala
305                 310                 315                 320

Gly Gln Asp Asp Glu Val Arg Glu Leu Leu Lys Ala Gly Ala Asp Val
                325                 330                 335

Asn Ala Lys Asp Glu Tyr Gly Leu Thr Pro Leu Tyr Leu Ala Thr Ala
            340                 345                 350

His Gly His Leu Glu Ile Val Glu Val Leu Leu Lys Ala Gly Ala Asp
        355                 360                 365

Val Asn Ala Val Asp Ala Ile Gly Phe Thr Pro Leu His Leu Ala Ala
    370                 375                 380

Phe Ile Gly His Leu Glu Ile Ala Glu Val Leu Leu Lys Ala Gly Ala
385                 390                 395                 400

Asp Val Asn Ala Gln Asp Lys Phe Gly Lys Thr Pro Ala Asp Ile Ala
                405                 410                 415

Ala Gly Ala Gly Asn Glu Asp Ile Ala Glu Val Leu Gln Lys Ala Ala
            420                 425                 430

Gly Ser Pro Thr Pro Thr Pro Thr Thr Pro Thr Pro Thr Pro Thr Thr
        435                 440                 445

Pro Thr Pro Thr Pro Thr Gly Ser Asp Leu Gly Lys Lys Leu Leu Glu
450                 455                 460
```

Ala Ala Arg Ala Gly Gln Asp Asp Glu Val Arg Glu Leu Leu Lys Ala
465                 470                 475                 480

Gly Ala Asp Val Asn Ala Lys Asp Tyr Phe Ser His Thr Pro Leu His
            485                 490                 495

Leu Ala Ala Arg Asn Gly His Leu Lys Ile Val Glu Val Leu Leu Lys
            500                 505                 510

Ala Gly Ala Asp Val Asn Ala Lys Asp Phe Ala Gly Lys Thr Pro Leu
            515                 520                 525

His Leu Ala Ala Asn Glu Gly His Leu Glu Ile Val Glu Val Leu Leu
            530                 535                 540

Lys Ala Gly Ala Asp Val Asn Ala Gln Asp Ile Phe Gly Lys Thr Pro
545                 550                 555                 560

Ala Asp Ile Ala Ala Asp Ala Gly His Glu Asp Ile Ala Glu Val Leu
            565                 570                 575

Gln Lys Ala Ala
            580

<210> SEQ ID NO 32
<211> LENGTH: 274
<212> TYPE: PRT
<213> ORGANISM: Artificial Sequence
<220> FEATURE:
<223> OTHER INFORMATION: Protein comprising two designed ankyrin repeat
      domains

<400> SEQUENCE: 32

Gly Ser Asp Leu Gly Ile Lys Leu Leu Phe Ala Ala Lys Gly Gln
1               5                   10                  15

Asp Asp Glu Val Arg Glu Leu Leu Lys Ala Gly Ala Asp Val Asn Ala
            20                  25                  30

Lys Asp Phe Gln Gly Val Thr Pro Leu His Ile Ala Ala Gln Ser Gly
        35                  40                  45

His Leu Glu Ile Val Glu Val Leu Leu Lys Ala Gly Ala Asp Val Asn
    50                  55                  60

Ala Lys Asp Val Thr Gly Asp Thr Pro Leu His Leu Ala Ala Gln His
65                  70                  75                  80

Gly His Leu Glu Ile Val Glu Val Leu Leu Lys Ala Gly Ala Asp Val
            85                  90                  95

Asn Ala Gln Asp Glu Arg Gly Trp Thr Pro Ala Asp Leu Ala Ala Asp
            100                 105                 110

Trp Gly His Glu Asp Ile Ala Glu Val Leu Gln Lys Ala Ala Gly Ser
        115                 120                 125

Pro Thr Pro Thr Pro Thr Thr Pro Thr Pro Thr Pro Thr Thr Pro Thr
    130                 135                 140

Pro Thr Pro Thr Gly Ser Asp Leu Gly Lys Lys Leu Leu Glu Ala Ala
145                 150                 155                 160

Arg Ala Gly Gln Asp Asp Glu Val Arg Glu Leu Leu Lys Ala Gly Ala
            165                 170                 175

Asp Val Asn Ala Lys Asp Glu Tyr Gly Leu Thr Pro Leu Tyr Leu Ala
            180                 185                 190

Thr Ala His Gly His Leu Glu Ile Val Glu Val Leu Leu Lys Ala Gly
        195                 200                 205

Ala Asp Val Asn Ala Val Asp Ala Ile Gly Phe Thr Pro Leu His Leu
    210                 215                 220

Ala Ala Phe Ile Gly His Leu Glu Ile Ala Glu Val Leu Leu Lys Ala

```
225                 230                 235                 240

Gly Ala Asp Val Asn Ala Gln Asp Lys Phe Gly Lys Thr Pro Ala Asp
                245                 250                 255

Ile Ala Ala Gly Ala Gly Asn Glu Asp Ile Ala Glu Val Leu Gln Lys
                260                 265                 270

Ala Ala

<210> SEQ ID NO 33
<211> LENGTH: 422
<212> TYPE: PRT
<213> ORGANISM: Artificial Sequence
<220> FEATURE:
<223> OTHER INFORMATION: Protein comprising three designed ankyrin
      repeat domains

<400> SEQUENCE: 33

Gly Ser Asp Leu Gly Lys Lys Leu Leu Glu Ala Ala Arg Ala Gly Gln
1               5                   10                  15

Asp Asp Glu Val Arg Glu Leu Leu Lys Ala Gly Ala Asp Val Asn Ala
            20                  25                  30

Lys Asp Tyr Phe Ser His Thr Pro Leu His Leu Ala Ala Arg Asn Gly
        35                  40                  45

His Leu Lys Ile Val Glu Val Leu Leu Lys Ala Gly Ala Asp Val Asn
    50                  55                  60

Ala Lys Asp Phe Ala Gly Lys Thr Pro Leu His Leu Ala Ala Asn Glu
65                  70                  75                  80

Gly His Leu Glu Ile Val Glu Val Leu Leu Lys Ala Gly Ala Asp Val
                85                  90                  95

Asn Ala Gln Asp Ile Phe Gly Lys Thr Pro Ala Asp Ile Ala Ala Asp
                100                 105                 110

Ala Gly His Glu Asp Ile Ala Glu Val Leu Gln Lys Ala Ala Gly Ser
            115                 120                 125

Pro Thr Pro Thr Pro Thr Thr Pro Thr Pro Thr Pro Thr Thr Pro Thr
        130                 135                 140

Pro Thr Pro Thr Gly Ser Asp Leu Gly Ile Lys Leu Leu Phe Ala Ala
145                 150                 155                 160

Ala Lys Gly Gln Asp Asp Glu Val Arg Glu Leu Leu Lys Ala Gly Ala
                165                 170                 175

Asp Val Asn Ala Lys Asp Phe Gln Gly Val Thr Pro Leu His Ile Ala
                180                 185                 190

Ala Gln Ser Gly His Leu Glu Ile Val Glu Val Leu Leu Lys Ala Gly
            195                 200                 205

Ala Asp Val Asn Ala Lys Asp Val Thr Gly Asp Thr Pro Leu His Leu
        210                 215                 220

Ala Ala Gln His Gly His Leu Glu Ile Val Glu Val Leu Leu Lys Ala
225                 230                 235                 240

Gly Ala Asp Val Asn Ala Gln Asp Glu Arg Gly Trp Thr Pro Ala Asp
                245                 250                 255

Leu Ala Ala Asp Trp Gly His Glu Asp Ile Ala Glu Val Leu Gln Lys
                260                 265                 270

Ala Ala Gly Ser Pro Thr Pro Thr Pro Thr Thr Pro Thr Pro Thr Pro
            275                 280                 285

Thr Thr Pro Thr Pro Thr Pro Thr Gly Ser Asp Leu Gly Lys Lys Leu
        290                 295                 300

Leu Glu Ala Ala Arg Ala Gly Gln Asp Asp Glu Val Arg Glu Leu Leu
```

-continued

```
            305                 310                 315                 320
Lys Ala Gly Ala Asp Val Asn Ala Lys Asp Glu Tyr Gly Leu Thr Pro
                    325                 330                 335

Leu Tyr Leu Ala Thr Ala His Gly His Leu Glu Ile Val Glu Val Leu
                340                 345                 350

Leu Lys Ala Gly Ala Asp Val Asn Ala Val Asp Ala Ile Gly Phe Thr
            355                 360                 365

Pro Leu His Leu Ala Ala Phe Ile Gly His Leu Glu Ile Ala Glu Val
370         375                 380

Leu Leu Lys Ala Gly Ala Asp Val Asn Ala Gln Asp Lys Phe Gly Lys
385             390                 395                 400

Thr Pro Ala Asp Ile Ala Ala Gly Ala Gly Asn Glu Asp Ile Ala Glu
                405                 410                 415

Val Leu Gln Lys Ala Ala
            420
```

RECOMBINANT BINDING PROTEINS TARGETING HER2 AND SERUM ALBUMIN, AND THEIR USES

CROSS-REFERENCE TO RELATED APPLICATION

The present application claims the benefit of and the priority to European patent application EP 16190221 filed on 22 Sep. 2016 with the European Patent Office. The content of European patent application EP 16190221 is incorporated herein by reference for all purposes in its entirety, including all tables, figures, and claims.

FIELD OF THE DISCLOSURE

Provided are new recombinant binding proteins. The proteins comprise two designed ankyrin repeat domains with binding specificity for HER2, and two designed ankyrin repeat domains with binding specificity for serum albumin, linked by polypeptide linkers. The recombinant binding proteins are useful for the treatment of disease. In particular, the recombinant binding proteins comprise designed ankyrin repeat domains with binding specificity for serum albumin exhibiting high storage stability. Furthermore provided are nucleic acids encoding said recombinant binding proteins, pharmaceutical compositions comprising said recombinant binding proteins or nucleic acids, and the use of said recombinant binding proteins, nucleic acids, or pharmaceutical compositions in the treatment of diseases.

BACKGROUND

Designed ankyrin repeat protein libraries (WO2002/020565; Binz, H. K., Amstutz, P., Kohl, A., Stumpp, M. T., Briand, C., Forrer, P., Grütter, M. G., and Plückthun, A., Nat. Biotechnol. 22, 575-582, 2004; Stumpp, M. T., Binz, H. K and Amstutz, P., Drug Discov. Today 13, 695-701, 2008) can be used for the selection of target specific designed ankyrin repeat domains. Such target specific designed ankyrin repeat domains in turn can be used as valuable components of recombinant binding proteins for the treatment of diseases. The selection of different designed ankyrin repeat domains with binding specificity for human epidermal growth factor receptor 2 (HER2 or ErbB2; UniProt P04626) has been described (WO2014/083208). In the present invention recombinant binding proteins are disclosed comprising designed ankyrin repeat domains with binding specificity for HER2. Unlike e.g. IgG antibodies, which exhibit long systemic half-lives mediated by FcRn recycling, proteins comprising designed ankyrin repeat domains typically exhibit a fast pharmacokinetic clearance and short terminal half-lives, unless the protein comprises elements that improve the pharmacokinetic properties, such as e.g. a designed ankyrin repeat domain with binding specificity to serum albumin described in WO2012/069654. Using serum albumin binding for improving pharmacokinetic properties of proteins is a process well-known in the art (see e.g. WO1991/001743; Frejd F. Y., 2012 (in Kontermann, R (Ed.) "Therapeutic proteins: strategies to modulate their plasma half-lives", Wiley-VCH Verlag GmbH, 2012, ISBN 978-3-527-32849-9); and WO2012/069654). In order to use designed ankyrin repeat domains with binding specificity for serum albumin in clinical drug candidates, it is desirable that the storage stability of known designed ankyrin repeat domains with binding specificity for serum albumin is improved. Disclosed herein are recombinant binding proteins comprising designed ankyrin repeat domains with binding specificity for serum albumin, wherein said designed ankyrin repeat domains with binding specificity for serum albumin exhibit improved storage stability properties. In contrast to earlier reports (Hopp, J., Horning, N., Zettlitz, K. A., Schwarz, A., Fuss, N., Müller, D., Kontermann, R. E. Protein Eng. Des. Sel. 23, 827-834, 2010), we surprisingly observed that by having two designed ankyrin repeat domains with binding specificity for serum albumin instead of one in the recombinant binding protein, the pharmacokinetic properties of the recombinant binding protein can be improved.

HER2 plays an important role in the pathogenesis and progression of certain types of cancer. HER2 is a transmembrane receptor tyrosine kinase (RTK) belonging to the wider family of ErbB receptors (Bublil, E. M. and Yarden, Y. Curr. Opin. Cell Biol. 19(2), 124-34, 2007). The ErbB receptor family is conserved across vertebrates and also includes ErbB1 or epidermal growth factor receptor (EGFR) or HER1 (UniProt P00533) and the receptors HER3 (ErbB3; UniProt P21860) and HER4 (ErbB4; UniProt Q15303). All ErbB receptors share extensive sequence and domain homologies, and form functional homodimers (e.g. ErbB1-ErbB1, HER2-HER2 and HER4-HER4) and heterodimers in all combinations. Receptor homo- and heterodimerization occurs upon ligand binding or receptor overexpression, and in turn activates intracellular receptor kinase domains by autophosphorylation. This then triggers downstream intracellular signaling and biological responses. Well-known antagonists of the ErbB signaling pathways include the monoclonal antibodies Trastuzumab (binding to domain IV of the extracellular domain of HER2 and inhibiting HER2 homodimerization) and Pertuzumab (binding to domain II of the extracellular domain of HER2 and inhibiting HER2/HER3 heterodimerization). Importantly, Trastuzumab has mainly an anti-proliferative effect and tumors may escape form such treatment in advanced disease stages. Pertuzumab, which has an unexpectedly low therapeutic efficacy as a single agent, can complement the activity of Trastuzumab by interfering with the HER2/HER3 heterodimerization. Thus, the combination of Trastuzumab with Pertuzumab is attractive for the treatment of HER2 positive cancer (Capelan M., et al., Ann. Oncol., 24, 273-82, 2013).

The combination of Trastuzumab and Pertuzumab has led to the concept that dual targeting of two domains in HER2 is required for superior anti-tumor efficacy. Antibody mixtures targeting domains II and IV of HER2, or simultaneous targeting of domain I and another domain of HER2 (US 20110033460; e.g. also domain IV), or domain I and domain IV (WO2014/060365; Jost, Ch., et al., Structure 21, 1-13, 2013; Tamaskovic, R., et al., Nat Commun 7, 11672, 2016), or domain II and domain IV (WO2014/083208), or simultaneous targeting of the Trastuzumab epitope on domain IV of HER2 and the Pertuzumab epitope on domain II of HER2 (WO2009/068625) have been reported. Some of the approaches included bi-paratopic binding proteins. Interestingly, some of the bi-paratopic binding proteins tested in WO2009/068625 had antagonistic effect, others agonistic effects. Reports of WO2014/083208 and Jost, Ch., et al (loc. cit.; WO2014/060365) indicate that the generation of antagonistic bi-paratopic binding proteins is not straight forward. Instead, careful selection of the individual domains (epitope, binder properties) as well as the structural arrangement (orientation, distance, linker length, linker composition) have to be optimized for effective antagonism. Additionally, the choice of the pharmacokinetic engineering moiety and its structural arrangement also have to be optimized. Together, this represents a choice from at least 250,000 different variants. Disclosed herein is a recombinant binding protein comprising (i) a bi-paratopic binding protein antagonizing ErbB-signaling consisting of two designed ankyrin repeat domains with binding specificity for HER2 and (ii) two designed ankyrin repeat domains with binding specificity for serum albumin and with improved storage stability. This recombinant binding protein, a DARPin® drug candidate, is shown to be a valuable drug candidate for the treatment of various diseases. DARPin® is a registered trademark of Molecular Partners AG, Switzerland.

SUMMARY

The invention relates to recombinant binding proteins comprising four designed ankyrin repeat domains, wherein two of said four designed ankyrin repeat domains are designed ankyrin repeat domains with binding specificity for HER2, and wherein two of said four designed ankyrin repeat domains are designed ankyrin repeat domains with binding specificity for serum albumin. The invention in particular relates to a recombinant binding protein comprising an amino acid sequence that has at least 90% amino acid sequence identity with SEQ ID NO: 21. The invention also relates to such a recombinant binding protein, wherein each of said two designed ankyrin repeat domains with binding specificity for serum albumin comprises the amino acid sequence of SEQ ID NO: 14. The invention in particular relates to a recombinant binding protein that has at least 95% sequence identity with the recombinant binding protein consisting of SEQ ID NO: 21. In one embodiment, said designed ankyrin repeat domains with binding specificity for serum albumin comprising SEQ ID NO: 14 each exhibit improved storage stability in PBS compared to a designed ankyrin repeat domain with binding specificity for serum albumin comprising the amino acid sequence of SEQ ID NO: 13. In one embodiment, the invention relates to a recombinant binding protein comprising the amino acid sequence of SEQ ID NO: 21. In one embodiment, the invention relates to a recombinant binding protein consisting of the amino acid sequence of SEQ ID NO: 21. In one embodiment, the recombinant binding protein comprising the amino acid sequence of SEQ ID NO: 21 exhibits higher storage stability than the recombinant binding protein comprising the amino acid sequence of SEQ ID NO: 22. In one embodiment, the recombinant binding protein of the invention inhibits BT474 cell proliferation with an inhibition constant below $10^{-7}$M. In one embodiment, the recombinant binding protein of the invention at a concentration of 100 nM exhibits stronger downregulation of AKT-S473 phosphorylation in BT474 cells than Trastuzumab at a concentration of 100 nM. The invention further relates to nucleic acids encoding the recombinant binding protein of the invention. The invention further relates to pharmaceutical compositions comprising the recombinant binding protein and/or nucleic acid of the invention, and a pharmaceutically acceptable carrier and/or diluent. The invention also relates to the pharmaceutical composition of the invention for use in the treatment of a disease, a neoplastic disease, cancer, breast cancer, ovarian cancer, gastric cancer, stomach cancer, uterine cancer, colorectal cancer, bladder cancer, HER2-overexpressing cancer, HER2 expressing cancer, HER2 addicted cancer, partially HER2 addicted cancer, HER2 amplified cancer, Trastuzumab-resistant cancer, Trastuzumab-sensitive cancer, gastro-intestinal cancer, or brain cancer. The invention further relates to a kit comprising the recombinant binding protein of the invention or a nucleic acid of the invention or a pharmaceutical composition of the invention. The invention further relates to a method for producing the recombinant binding protein of the invention, the method comprising the steps of (i) expressing said recombinant binding protein in bacteria, and (ii) purifying said recombinant binding protein using chromatography.

BRIEF DESCRIPTION OF THE FIGURES

FIG. 1A: Illustration of a designed ankyrin repeat domain with binding specificity for serum albumin. Examples of such ankyrin repeat domains are designed ankyrin repeat domains comprising an amino acid sequence selected from the group consisting of SEQ ID NOs: 12 to 15, in particular the designed ankyrin repeat domain comprising amino acid sequence SEQ ID NO: 14. FIG. 1B: Illustration of a designed ankyrin repeat domain with binding specificity for HER2. Examples of such ankyrin repeat domains are designed ankyrin repeat domains comprising an amino acid sequence selected from the group consisting of SEQ ID NOs: 16 to 20, in particular the designed ankyrin repeat domains comprising amino acid sequences SEQ ID NOs: 16 and 17. FIG. 1C: Illustration of a polypeptide linker (for example a polypeptide comprising an amino acid sequence corresponding to any of SEQ ID NOs: 2 to 9, in particular the polypeptide linker comprising the amino acid sequence of SEQ ID NO: 9). FIG. 1D: Illustration of an N-terminal amino acid sequence. Examples for such N-terminal amino acid sequences are for example the sequences MGS or GS (as for example present at the N terminus of any of SEQ ID NOs: 21 to 30 and 32 and 33), or polypeptide tags, as exemplified by the amino acid sequence corresponding to SEQ ID NO: 1. FIG. 1E: Illustration of a recombinant binding protein as provided herein comprising two designed ankyrin repeat domains with binding specificity for serum albumin, and two designed ankyrin repeat domains each with binding specificity for HER2, linked by polypeptide linkers and having an N-terminal amino acid sequence. The two designed ankyrin repeat domains with binding specificity for serum albumin are flanking the two other designed ankyrin repeat domains. The recombinant binding protein comprising the amino acids of SEQ ID NO: 21 corresponds to this illustration.

SDS 15% PAGE analysis of Protein #13-His (#13) (FIG. 2A) and Protein #14-His (#14; see Example 1) (FIG. 2B) stored at 10 mg/ml in PBS for 1 week at 4° C. (1), 25° C. (2), 40° C. (3), and 60° C. (4). Protein #14-His exhibits higher storage stability than Protein #13-His. M: Marker (lower band: 6.5 kDa; band at Protein #14-His level: 14.4 kDa; upper band in case of Protein #14-His PAGE: 21.5 kDa).

Figure 3:
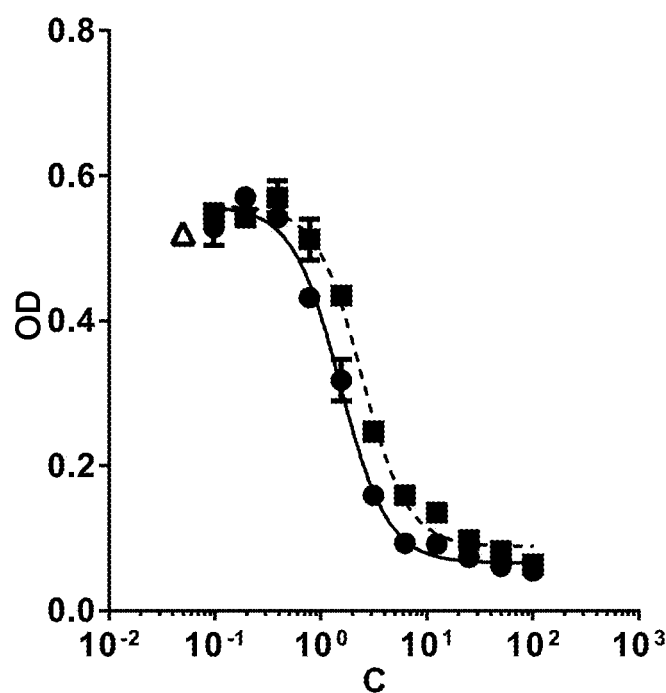

FIG. 3. Inhibition of BT474 cell proliferation by recombinant binding proteins with binding specificity for HER2.

BT474 breast cancer cell proliferation inhibition was performed as described in Example 6. The recombinant binding protein comprising SEQ ID NO: 21 exhibits a lower IC50 than the recombinant binding protein comprising SEQ ID NO: 23, indicating that having SEQ ID NOs: 16 and 17 in a recombinant binding protein is more favorable than having SEQ ID NOs: 18 and 17. Filled circles and solid line:

Protein #21-His; Filled squares and dashed line: Protein #23-His; Triangle: No inhibitor. OD: OD405-OD620; C: concentration in nM.

FIGS. 4A to 4E. Tumor xenograft mouse experiments.

Figure 4A:
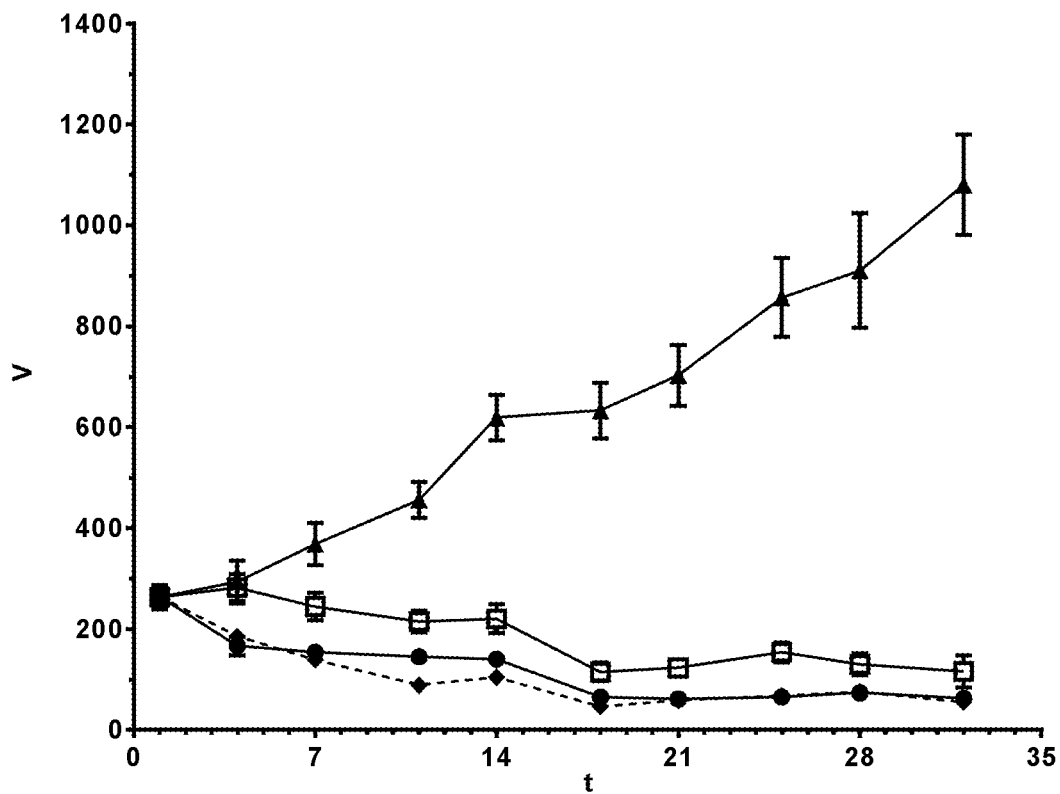
Figure 4B:
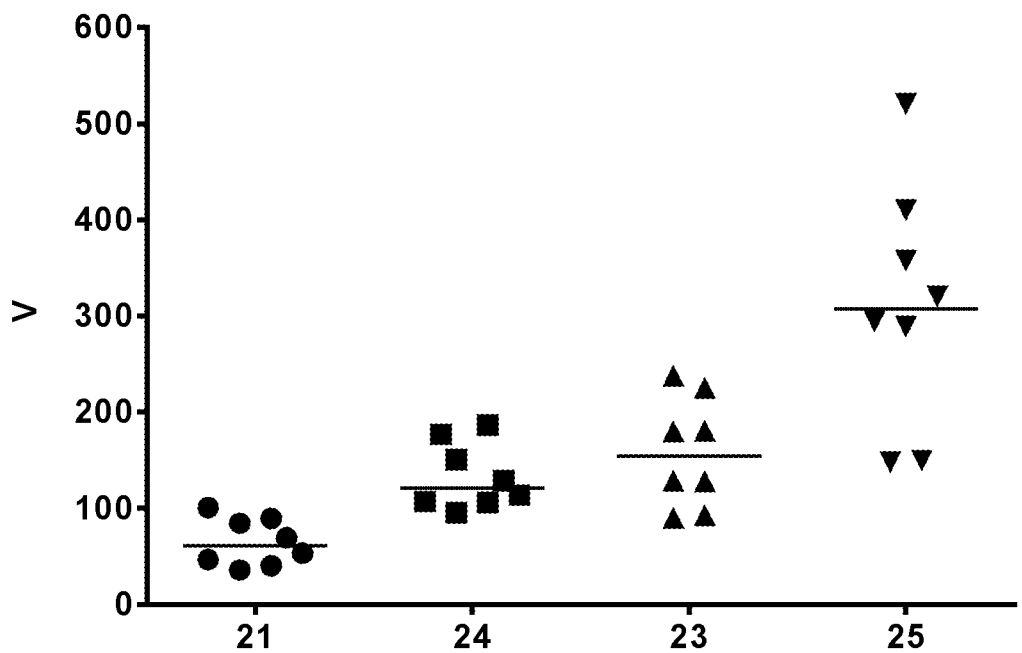
Figure 4C:
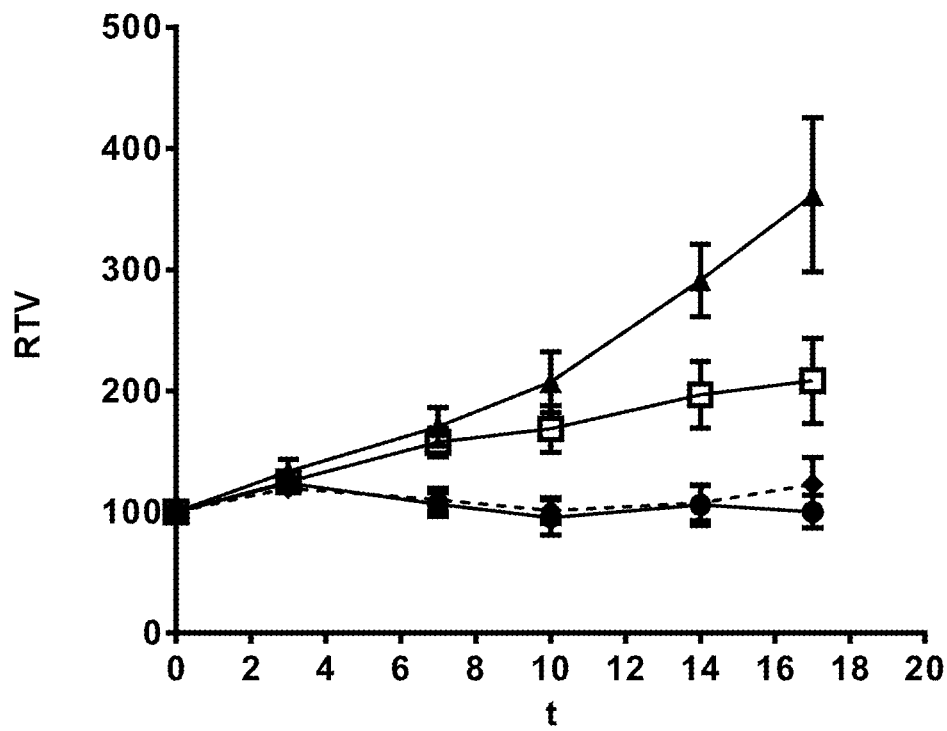
Figure 4D:
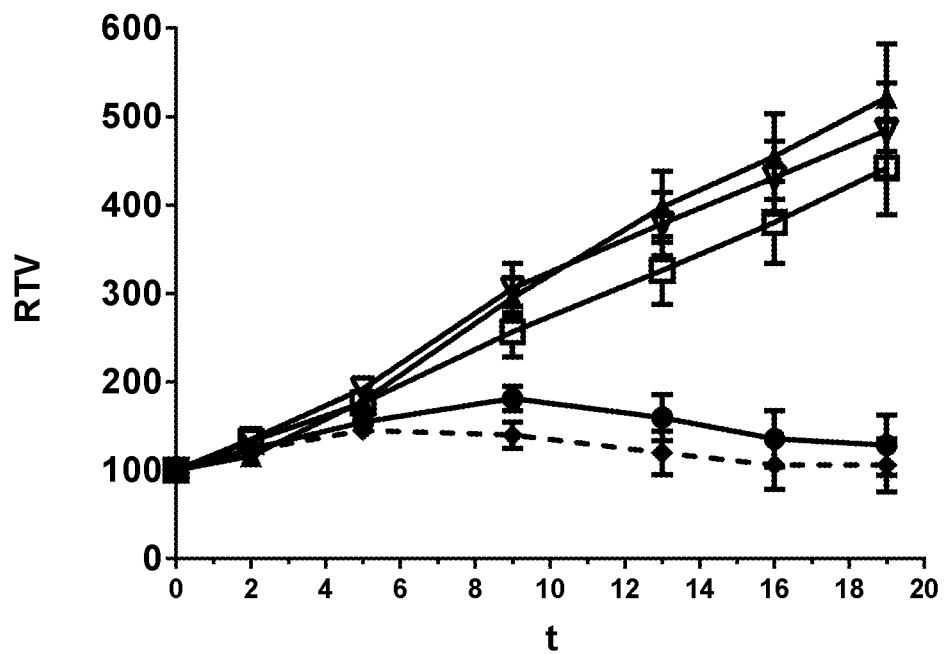
Figure 4E:
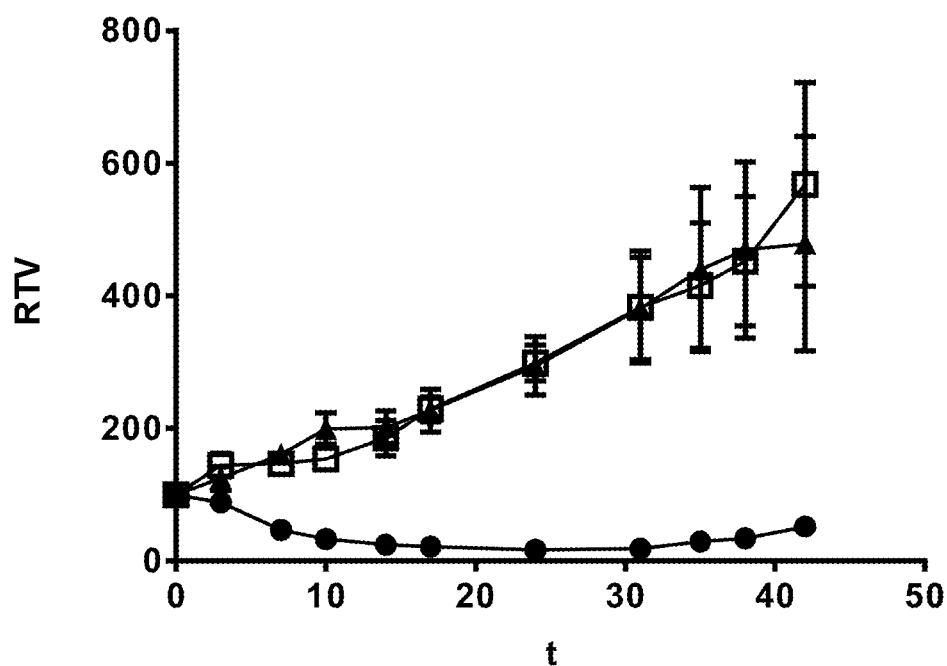

FIG. 4A: BT474 breast cancer tumor xenograft mouse model. The model was performed as described in Example 7. Triangles: PBS; open squares: Trastuzumab; diamonds with dashed line: Trastuzumab & Pertuzumab; Filled circles: recombinant binding protein with binding specificity for HER2 (Protein #21-His); V: tumor volume [mm$^3$]; t: time [d]. FIG. 4B: BT474 breast cancer tumor xenograft mouse model comparing Protein #21-His (21), Protein #23-His (23), Protein #24-His (24), or Protein #25-His (25) at day 18 of treatment. The experiment was performed as described in Example 7. Protein #21-His is significantly more efficacious in inhibiting tumor growth than Protein #24-His (p=0.0003), Protein #23-His, or Protein #25. V: tumor volume [mm$^3$]; t: time [d]. FIG. 4C and FIG. 4D: GXA3039 gastric cancer patient derived tumor xenograft mouse model. The experiment was performed twice as described in Example 7. PBS (triangles), Pertuzumab (open inverse triangles), Trastuzumab (open squares), a mixture of Trastuzumab and Pertuzumab (diamonds with dashed line) as well as Protein #21 were used in these experiments. FIG. 4C: Protein #21 exhibits strong inhibition of tumor growth, similar to the combination of Trastuzumab and Pertuzumab, whereas Trastuzumab alone is less efficacious. FIG. 4D: Protein #21 exhibits strong inhibition of tumor growth, similar to the combination of Trastuzumab and Pertuzumab. Trastuzumab alone and Pertuzumab alone are significantly less efficacious. RTV: relative tumor volume referenced to the tumor volume at treatment start [%]; t: time [d]. FIG. 4E: GXF281 gastric cancer patient derived tumor xenograft mouse model. The experiment was performed as described in Example 7. PBS (triangles), Lapatinib (open squares), as well as Protein #21 (filled circles). Protein #21 shows strong inhibition of tumor growth compared to Lapatinib in this model. RTV: relative tumor volume referenced to the tumor volume at treatment start [%]; t: time [d].

Figure 5A:
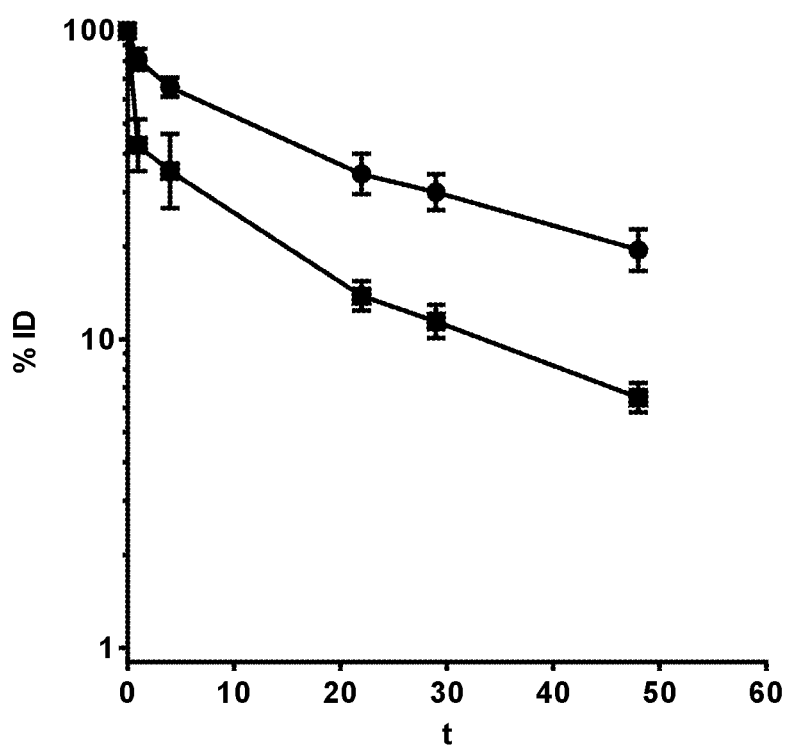
Figure 5B:
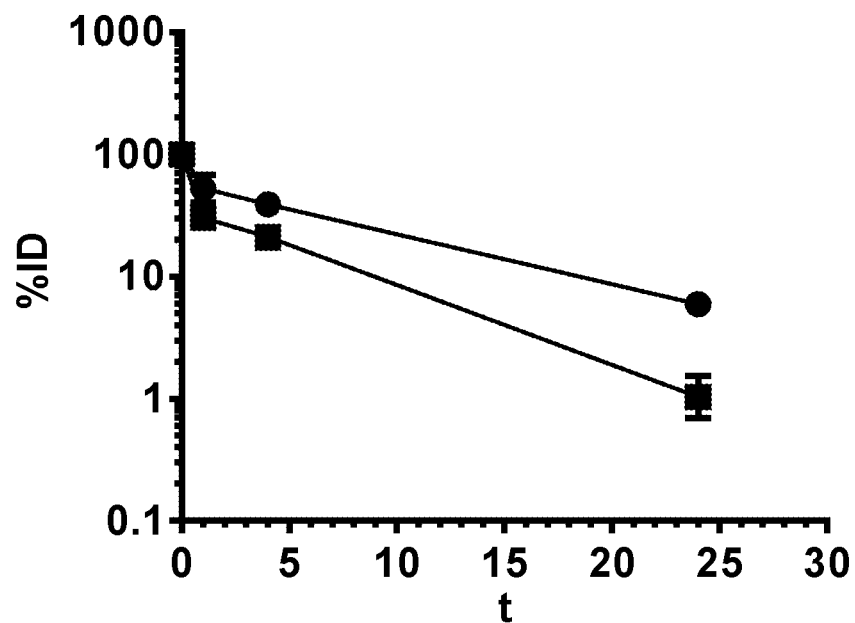
Figure 5C:
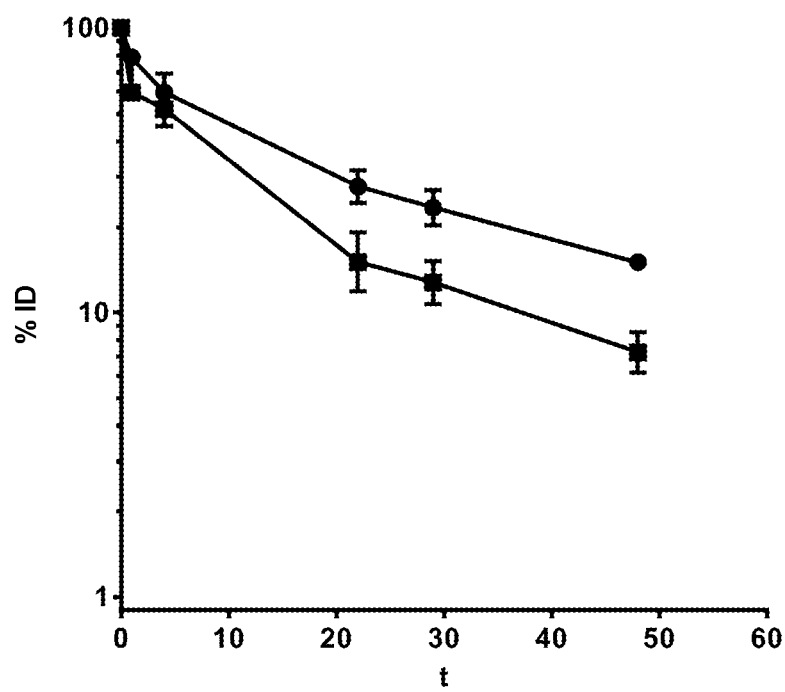

FIGS. 5A to 5C. Pharmacokinetic analyses in mouse.

FIG. 5A: Pharmacokinetic property analysis in mouse, comparing Protein #21-His (filled circles) with Protein #23-His (squares) according to Example 8. This experiment indicates a pharmacokinetic advantage of having SEQ ID NO: 16 present in the recombinant binding protein, rather than SEQ ID NO: 18. FIG. 5B: Pharmacokinetic property analysis in mouse, comparing Protein #30-His (filled circles; comprises two designed ankyrin repeat domains with binding specificity for serum albumin) with Protein #29-His (filled squares; comprises one designed ankyrin repeat domain with binding specificity for serum albumin) according to Examples 8 and 11. Having two designed ankyrin repeat domains with binding specificity for serum albumin improves the pharmacokinetic profile beyond the profile achieved with one designed ankyrin repeat domain with binding specificity for serum albumin. FIG. 5C: Pharmacokinetic comparison of recombinant binding protein comprising GlySer polypeptide linkers (Protein #26-His; Filled squares) vs. a recombinant binding protein comprising Pro-Thr polypeptide linkers (Protein #27-His; Filled circles) as described in Examples 8 and 10. Having ProThr polypeptide linkers has a favorable impact on pharmacokinetic properties in mouse. % ID: percent injected dose normalized to the 1 hour measurement value [%]; t: time [hours].

Figure 6A:
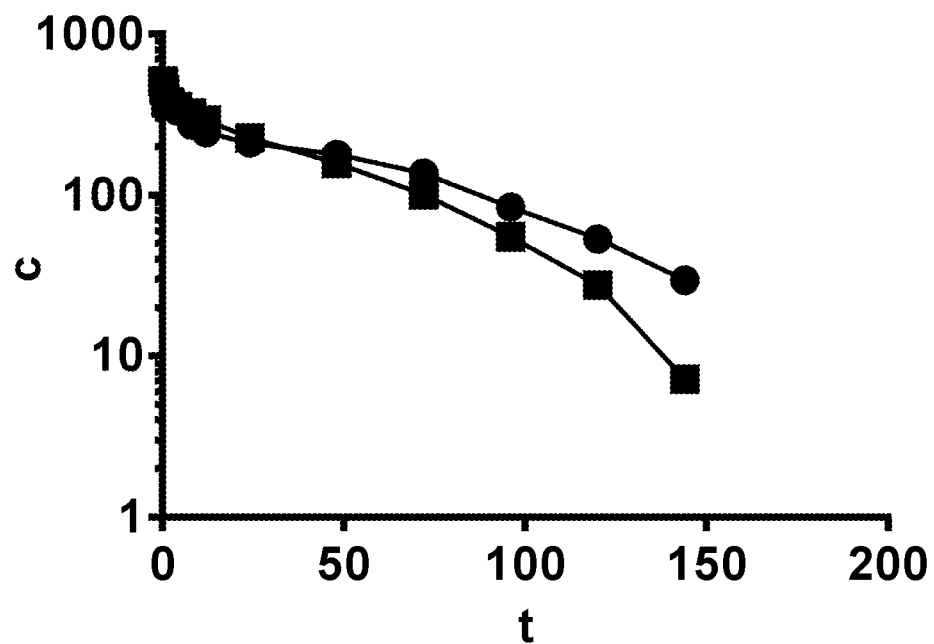
Figure 6B:
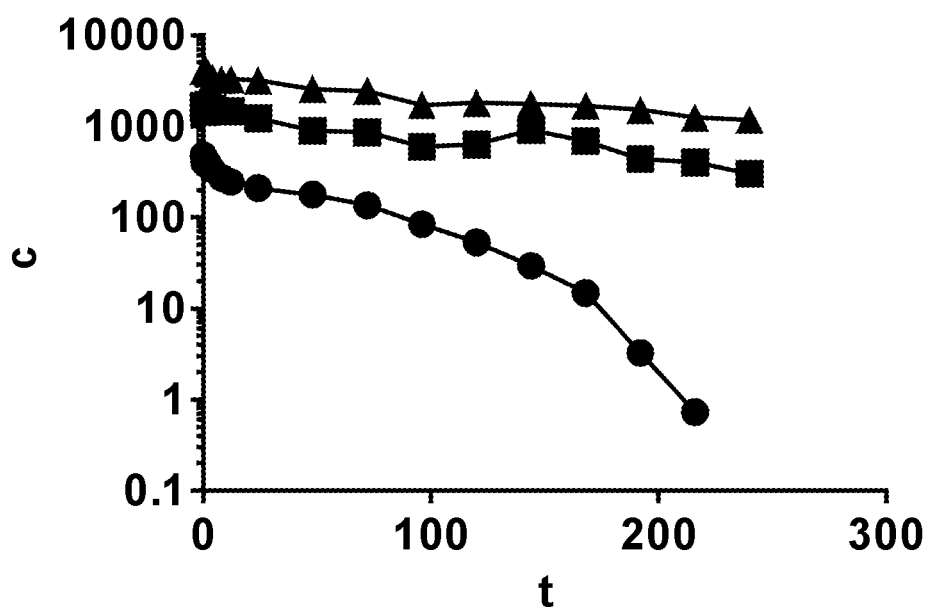

FIGS. 6A and 6B. Pharmacokinetic analyses in cynomolgus monkey.

FIG. 6A: Pharmacokinetic property analysis of Protein #21-His (filled circles) and Protein #23-His (filled squares) at 1 mg/kg in cynomolgus monkey according to Example 9. A longer terminal half-life is observed for Protein #21-His, indicating that having SEQ ID NO: 16 present in the recombinant binding protein is more favorable than having SEQ ID NO: 18 present. FIG. 6B: Pharmacokinetic property analysis of Protein #21-His at 1 mg/kg (filled circles), 5 mg/kg (filled squares), and 10 mg/kg (filled triangles) in cynomolgus monkey according to Example 9. Protein #21-His displays a dose-dependent increase of the terminal half-life from 47 hours at 1 mg/kg to 100 hours at 5 mg/kg to about 180 hours at 10 mg/kg. C: Concentration [nM]; t: time [hours].

Figure 7:
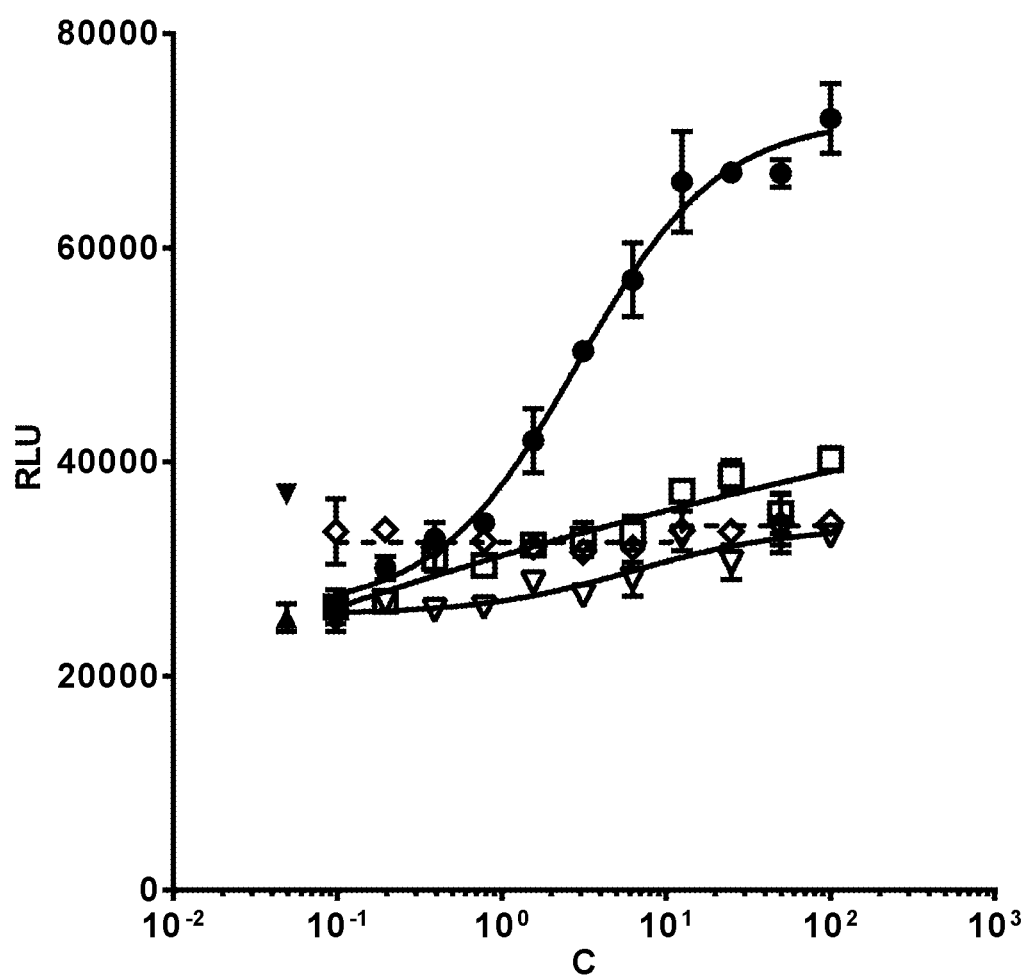

FIG. 7. Apoptosis induction in BT474 cells.

Measurement of apoptosis of BT474 cells induced by varying concentrations of Protein #21 (filled circles), Trastuzumab (open squares), Pertuzumab (open inverse triangles), or a mixture of 100 nM Trastuzumab and varying concentrations of Pertuzumab (open diamonds; dashed line) according to Example 6. The results are plotted including non-linear regression fit curves. The measurements for PBS (filled triangle) and 100 nM Trastuzumab (filled inverse triangle) are shown as references at 50 pM. C: concentration in [nM]; RLU: relative light units.

DETAILED DESCRIPTION

The invention relates to recombinant binding proteins comprising four designed ankyrin repeat domains, wherein two of said four designed ankyrin repeat domains are designed ankyrin repeat domains with binding specificity for HER2, and wherein two of said four designed ankyrin repeat domains are designed ankyrin repeat domains with binding specificity for serum albumin. SEQ ID NO: 21 is an example of such a recombinant binding protein.

In one embodiment, each of said designed ankyrin repeat domains with binding specificity for serum albumin has at least 90%, 91%, 92%, 93%, 94%, 95%, 96%, 97%, 98%, 99%, or 100% amino acid sequence identity with SEQ ID NO: 14. In one embodiment, each of said designed ankyrin repeat domains with binding specificity for serum albumin consists of an amino acid sequence selected from the group consisting of (i) SEQ ID NO: 14, and/or (ii) sequences wherein up to 10, 9, 8, 7, 6, 5, 4, 3, 2, 1 or 0 amino acids of SEQ ID NO: 14 are exchanged by any amino acid. In one embodiment, each of said designed ankyrin repeat domains with binding specificity for serum albumin consists of an amino acid sequence selected from the group consisting of (i) SEQ ID NO: 14, and/or (ii) sequences wherein up to 10, 9, 8, 7, 6, 5, 4, 3, 2, 1 or 0 amino acids of SEQ ID NO: 14 are exchanged by any amino acid, and each of said designed ankyrin repeat domains with binding specificity for serum albumin is not identical to a sequence of a designed ankyrin repeat domain with binding specificity for serum albumin selected from the group consisting of SEQ ID NOs: 12, 13, or 15 of this application, as well as SEQ ID NOs: 17 to 25 and 43 to 48 of WO2012/069654.

In one embodiment the penultimate amino acid of any of SEQ ID NOs: 10 to 20 is Ala or Leu, preferably Ala. In one embodiment the C-terminal amino acid of any of SEQ ID NOs: 10 to 20 is Ala or Asn, preferably Ala, or is optionally missing. For example, SEQ ID NO: 29 comprises e.g. SEQ ID NO: 15 in which the penultimate amino acid is Leu and the C-terminal amino acid is missing. Preferably, the penultimate amino acid and the C-terminal amino acid of any designed ankyrin repeat domain (i.e. any of SEQ ID NOs: 10 to 20) present in a recombinant binding protein of the present invention are both Ala.

In one embodiment the amino acids Gly Ser at the N terminus of any of SEQ ID NOs: 10 to 30 and 32 to 33 are optionally missing.

In one embodiment, said two designed ankyrin repeat domains with binding specificity for serum albumin are at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical in amino acid sequence. In one embodiment, said two designed ankyrin repeat domains with binding specificity for serum albumin of said recombinant binding protein are identical in amino acid sequence.

In one embodiment, said two designed ankyrin repeat domains with binding specificity for serum albumin of the recombinant binding protein of the invention each comprise the amino acid sequence of SEQ ID NO: 14. In one embodiment, said two designed ankyrin repeat domains with binding specificity for serum albumin of the recombinant binding protein of the invention each consist of SEQ ID NO: 14.

In one embodiment, the two designed ankyrin repeat domains with binding specificity for serum albumin of said recombinant binding protein are able to simultaneously bind one serum albumin molecule each.

In one embodiment, the invention relates to recombinant binding proteins comprising four designed ankyrin repeat domains, wherein two of said four designed ankyrin repeat domains are designed ankyrin repeat domains with binding specificity for HER2, and wherein two of said four designed ankyrin repeat domains are designed ankyrin repeat domains with binding specificity for serum albumin, and wherein each of said two designed ankyrin repeat domains with binding specificity for serum albumin consist of SEQ ID NO: 14.

In one embodiment, said designed ankyrin repeat domain comprising SEQ ID NO: 14 exhibits improved storage stability in PBS compared to the designed ankyrin repeat domain comprising SEQ ID NO: 13. In one embodiment, said designed ankyrin repeat domain comprising SEQ ID NO: 14 exhibits improved storage stability in PBS compared to the designed ankyrin repeat domain comprising SEQ ID NO: 15. In one embodiment, said designed ankyrin repeat domain consisting of SEQ ID NO: 14 exhibits improved storage stability in PBS compared to the designed ankyrin repeat domain consisting of SEQ ID NO: 13. In one embodiment, said designed ankyrin repeat domain consisting of SEQ ID NO: 14 exhibits improved storage stability in PBS compared to the designed ankyrin repeat domain consisting of SEQ ID NO: 15. Designed ankyrin repeat domains consisting of SEQ ID NOs: 12 to 15 are examples of designed ankyrin repeat domains with binding specificity for serum albumin.

In one embodiment, said recombinant binding protein comprises two designed ankyrin repeat domains with binding specificity for serum albumin, wherein each of said two designed ankyrin repeat domains with binding specificity for serum albumin comprises amino acid sequence SEQ ID NO: 14, and wherein each of said designed ankyrin repeat domains with binding specificity for serum albumin exhibits improved storage stability in PBS, preferably reduced amounts of degradation products after storage at 40° C. for 1 month at 10 mg/ml in PBS, compared to a designed ankyrin repeat domain comprising amino acid sequence SEQ ID NO: 13.

In one embodiment, said recombinant binding protein comprising two designed ankyrin repeat domains with binding specificity for serum albumin, wherein each of said two designed ankyrin repeat domains with binding specificity for serum albumin comprises the amino acid sequence of SEQ ID NO: 14, exhibits improved storage stability, preferably reduced amounts of degradation products after storage at 40° C. for 1 month at 10 mg/ml in PBS, compared to a corresponding recombinant binding protein, wherein each of said two designed ankyrin repeat domains with binding specificity for serum albumin comprises the amino acid sequence of SEQ ID NO: 13. SEQ ID NOs: 21 and 22 are examples of such recombinant binding proteins comprising SEQ ID NO: 14 and 13, respectively.

In one embodiment, said recombinant binding protein, comprising two designed ankyrin repeat domains with binding specificity for serum albumin, exhibits improved pharmacokinetic properties compared to a corresponding recombinant binding protein comprising only one designed ankyrin repeat domain with binding specificity for serum albumin. In one embodiment, said recombinant binding protein, comprising two designed ankyrin repeat domains with binding specificity for serum albumin, exhibits a longer terminal half-life in cynomolgus monkey compared to a corresponding recombinant binding protein comprising only one designed ankyrin repeat domain with binding specificity for serum albumin. Example 11 (see FIG. 5B) discloses recombinant binding proteins with improved pharmacokinetic properties.

In one embodiment, said two designed ankyrin repeat domains with binding specificity for serum albumin are one N-terminal and one C-terminal of said two designed ankyrin repeat domains with binding specificity for HER2.

In one embodiment, one of said designed ankyrin repeat domains with binding specificity for HER2 has at least 90%, 91%, 92%, 93%, 94%, 95%, 96%, 97%, 98%, 99%, or 100% amino acid sequence identity with SEQ ID NO: 16. In one embodiment, one of said designed ankyrin repeat domains with binding specificity for HER2 comprises an amino acid sequence selected from the group consisting of (i) SEQ ID NO: 16, and/or (ii) sequences wherein up to 10, 9, 8, 7, 6, 5, 4, 3, 2, 1 or 0 amino acids of SEQ ID NO: 16 are exchanged by any amino acid. In one embodiment, one of said designed ankyrin repeat domains with binding specificity for HER2 comprises SEQ ID NO: 16. In one embodiment, one of said designed ankyrin repeat domains with binding specificity for HER2 consists of SEQ ID NO: 16.

In one embodiment, one of said designed ankyrin repeat domains with binding specificity for HER2 has at least 90%, 91%, 92%, 93%, 94%, 95%, 96%, 97%, 98%, 99% or 100% amino acid sequence identity with SEQ ID NO: 17. In one embodiment, one of said designed ankyrin repeat domains with binding specificity for HER2 comprises an amino acid sequence selected from the group consisting of (i) SEQ ID NO: 17, and/or (ii) sequences wherein up to 10, 9, 8, 7, 6, 5, 4, 3, 2, 1 or 0 amino acids of SEQ ID NO: 17 are exchanged by any amino acid. In one embodiment, one of said designed ankyrin repeat domains with binding specificity for HER2 comprises SEQ ID NO: 17. In one embodiment, one of said designed ankyrin repeat domains with binding specificity for HER2 consists of SEQ ID NO: 17.

In one embodiment, one of said designed ankyrin repeat domains with binding specificity for HER2 has at least 90%, 91%, 92%, 93%, 94%, 95%, 96%, 97%, 98%, 99%, or 100% amino acid sequence identity with SEQ ID NO: 16, and one of said designed ankyrin repeat domains with binding specificity for HER2 has at least 90%, 91%, 92%, 93%, 94%, 95%, 96%, 97%, 98%, 99%, or 100% amino acid sequence identity with SEQ ID NO: 17. In one embodiment, one of said designed ankyrin repeat domains with binding specificity for HER2 comprises an amino acid sequence selected from the group consisting of (i) SEQ ID NO: 16, and/or (ii) sequences wherein up to 10, 9, 8, 7, 6, 5, 4, 3, 2, 1 or 0 amino acids of SEQ ID NO: 16 are exchanged by any amino acid, and one of said designed ankyrin repeat domains with binding specificity for HER2 comprises an amino acid sequence selected from the group consisting of (i) SEQ ID NO: 17, and/or (ii) sequences wherein up to 10, 9, 8, 7, 6, 5, 4, 3, 2, 1 or 0 amino acids of SEQ ID NO: 17 are exchanged by any amino acid. In one embodiment, one of said designed ankyrin repeat domains with binding specificity for HER2 comprises SEQ ID NO: 16 and one of said designed ankyrin repeat domains with binding specificity for HER2 comprises SEQ ID NO: 17. In one embodiment, one of said designed ankyrin repeat domains with binding specificity for HER2 consists of SEQ ID NO: 16 and one of said designed ankyrin repeat domains with binding specificity for HER2 consists of SEQ ID NO: 17. In one embodiment, said recombinant binding protein comprises SEQ ID NO: 16 N-terminal of SEQ ID NO: 17.

In one embodiment, said recombinant binding protein comprises an amino acid sequence that has 90%, 91%, 92%, 93%, 94%, 95%, 96%, 97%, 98%, 99%, or 100% amino acid sequence identity with SEQ ID NO: 32. In one embodiment, said recombinant binding protein comprises an amino acid sequence selected from the group consisting of (i) SEQ ID NO: 32 and/or (ii) sequences wherein up to 20, 19, 18, 17, 16, 15, 14, 13, 12, 11, 10, 9, 8, 7, 6, 5, 4, 3, 2, 1 or 0 amino acids of SEQ ID NO: 32 are exchanged by any amino acid.

In one embodiment, the invention relates to a recombinant binding protein comprising four designed ankyrin repeat domains, wherein two of said four designed ankyrin repeat domains are designed ankyrin repeat domains with binding specificity for HER2 consisting of SEQ ID NOs: 16 and 17, and wherein two of said four designed ankyrin repeat domains are designed ankyrin repeat domains with binding specificity for serum albumin, and wherein each of said two designed ankyrin repeat domains with binding specificity for serum albumin consist of SEQ ID NO: 14.

In one embodiment, the invention relates to a recombinant binding protein comprising SEQ ID NO: 32 and twice SEQ ID NO: 14. In one embodiment, the invention relates to a recombinant binding protein comprising SEQ ID NO: 32 and twice SEQ ID NO: 14, wherein SEQ ID NO: 32 is flanked by one SEQ ID NO: 14 at the N terminus and one SEQ ID NO: 14 at the C terminus.

In one embodiment, the polypeptide linkers linking the designed ankyrin repeat domains present in the recombinant binding protein of the present invention comprise amino acid sequences selected from the group consisting of amino acid sequences SEQ ID NOs: 2 to 9, more preferably SEQ ID NOs: 3 to 9, more preferably SEQ ID NOs: 4 to 9, more preferably SEQ ID NOs: 6 or 9, more preferably SEQ ID NO: 9, in which up to 4, 3, 2, 1, 0 amino acids of said SEQ ID NOs: 2 to 9, more preferably SEQ ID NOs: 3 to 9, more preferably SEQ ID NOs: 4 to 9, more preferably SEQ ID NOs: 6 or 9, more preferably SEQ ID NO: 9 are exchanged by any amino acid. In one embodiment, the flanking N-terminal Gly Ser of any of SEQ ID NOs: 7 to 9 and/or the flanking C-terminal Gly Ser of any of SEQ ID NOs: 2 to 6 are optionally missing. In one embodiment, any of SEQ ID NOs: 2 to 9 optionally additionally comprises Arg Ser C-terminally (as e.g. present in SEQ ID NO: 29). In one embodiment, said polypeptide linkers comprise an amino acid sequence chosen from any of amino acid sequences SEQ ID NOs: 2 to 9, more preferably SEQ ID NOs: 3 to 9, more preferably SEQ ID NOs: 4 to 9, more preferably SEQ ID NOs: 6 or 9, more preferably SEQ ID NO: 9. In one embodiment, the polypeptide linkers linking the designed ankyrin repeat domains present in a recombinant binding protein of the present invention consist of an amino acid sequence selected from of any of amino acid sequences SEQ ID NOs: 2 to 9, more preferably SEQ ID NOs: 3 to 9, more preferably SEQ ID NOs: 4 to 9, more preferably SEQ ID NOs: 6 or 9, more preferably SEQ ID NO: 9. In one embodiment, the polypeptide linkers linking the designed ankyrin repeat domains present in a recombinant binding protein of the present invention each consist of SEQ ID NO: 9. In one embodiment, said polypeptide linkers present in a recombinant binding protein of the present invention are 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical, preferably identical. In one embodiment, each of said two designed ankyrin repeat domains with binding specificity for serum albumin consists of the amino acid sequence of SEQ ID NO: 14, and said four designed ankyrin repeat domains are linked by polypeptide linkers each consisting of the amino acid sequence of SEQ ID NO: 9.

In one embodiment, the invention relates to a recombinant binding protein comprising, from N to C terminus: SEQ ID NO: 14-SEQ ID NO: 16-SEQ ID NO: 17-SEQ ID NO: 14, linked by polypeptide linkers. In one embodiment, the invention relates to a recombinant binding protein comprising from N to C terminus: SEQ ID NO: 14-SEQ ID NO: 9-SEQ ID NO: 16-SEQ ID NO: 9-SEQ ID NO: 17-SEQ ID NO: 9-SEQ ID NO: 14.

In one embodiment, the invention relates to a recombinant binding protein comprising an amino acid sequence that has at least 88%, 89%, 90%, 91%, 92%, 93%, 94%, 95%, 96%, 97%, 98%, 99%, or 100% amino acid sequence identity with the recombinant binding protein consisting of SEQ ID NO: 21. In one embodiment, the invention relates to a recombinant binding protein comprising an amino acid sequence selected from the group consisting of (i) SEQ ID NO: 21 and/or (ii) amino acid sequences in which up to 72, 71, 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1, or 0 amino acids of SEQ ID NO: 21 are exchanged by other amino acids. In one embodiment, the invention relates to a recombinant binding protein consisting of an amino acid sequence that has at least 88%, 89%, 90%, 91%, 92%, 93%, 94%, 95%, 96%, 97%, 98%, 99%, or 100% amino acid sequence identity with the recombinant binding protein consisting of SEQ ID NO: 21. In one embodiment, the invention relates to a recombinant binding protein consisting of the amino acid sequence selected from the group consisting of (i) SEQ ID NO: 21 and (ii) amino acid sequences in which up to 72, 71, 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1, or 0 amino acids of SEQ ID NO: 21 are exchanged by other amino acids. Preferably, said amino acid exchanges in SEQ ID NO: 21 are located in positions 127 to 444 of SEQ ID NO: 21.

In one embodiment, the invention relates to a recombinant binding protein comprising an amino acid sequence that has at least 88%, 89%, 90%, 91%, 92%, 93%, 94%, 95%, 96%, 97%, 98%, 99%, or 100% amino acid sequence identity with the recombinant binding protein consisting of SEQ ID NO: 21, wherein said recombinant binding protein comprises two designed ankyrin repeat domains with binding specificity for serum albumin, and wherein each of said two designed ankyrin repeat domains with binding specificity for serum albumin comprises amino acid sequence SEQ ID NO: 14. In one embodiment, the invention relates to a recombinant binding protein comprising an amino acid sequence that has at least 88%, 89%, 90%, 91%, 92%, 93%, 94%, 95%, 96%, 97%, 98%, 99%, or 100% amino acid sequence identity with the recombinant binding protein consisting of SEQ ID NO: 21, wherein said recombinant binding protein comprises two designed ankyrin repeat domains with binding specificity for serum albumin, and wherein each of said two designed ankyrin repeat domains with binding specificity for serum albumin consists of amino acid sequence SEQ ID NO: 14. In one embodiment, the invention relates to a recombinant binding protein comprising an amino acid sequence selected from the group consisting of (i) SEQ ID NO: 21 and/or (ii) amino acid sequences in which up to 72, 71, 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1, or 0 amino acids of SEQ ID NO: 21 are exchanged by other amino acids, wherein said recombinant binding protein comprises two designed ankyrin repeat domains with binding specificity for serum albumin, and wherein each of said two designed ankyrin repeat domains with binding specificity for serum albumin comprises amino acid sequence SEQ ID NO: 14. In one embodiment, the invention relates to a recombinant binding protein comprising an amino acid sequence selected from the group consisting of (i) SEQ ID NO: 21 and/or (ii) amino acid sequences in which up to 72, 71, 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1, or 0 amino acids of SEQ ID NO: 21 are exchanged by other amino acids, wherein said recombinant binding protein comprises two designed ankyrin repeat domains with binding specificity for serum albumin, and wherein each of said two designed ankyrin repeat domains with binding specificity for serum albumin consists of amino acid sequence SEQ ID NO: 14.

In one embodiment, the invention relates to a recombinant binding protein comprising the amino acid sequence consisting of SEQ ID NO: 21. In one embodiment, the invention relates to a recombinant binding protein comprising the amino acid sequence of SEQ ID NO: 21. Preferred is a recombinant binding protein comprising the amino acid sequence of SEQ ID NO: 21. Preferred is SEQ ID NO: 21. Preferred is a recombinant binding protein, wherein the amino acid sequence is SEQ ID NO: 21. Preferred is a protein, wherein the amino acid sequence is SEQ ID NO: 21. Preferred is a recombinant binding protein consisting of SEQ ID NO: 21. Preferred is a recombinant binding protein consisting of the amino acid sequence of SEQ ID NO: 21.

Figure 1A:
FIGS. 1A to 1E. Illustration of recombinant binding proteins with binding specificity for HER2 comprising designed ankyrin repeat domains with binding specificity for serum albumin.
Figure 1B:
Figure 1C:
Figure 1D:
Figure 1E:
Figure 2A:
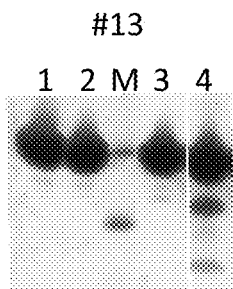
FIGS. 2A and 2B. Improved storage stability of a protein comprising SEQ ID NO: 14.
Figure 2B:
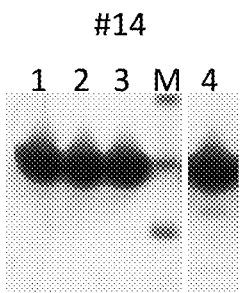

Multiple features make the protein encoded by SEQ ID NO: 21 the preferred recombinant binding protein of the invention. It comprises two designed ankyrin repeat domains with binding specificity for HER2 and two designed ankyrin repeat domains with binding specificity for serum albumin, wherein each of said two designed ankyrin repeat domains with binding specificity for serum albumin consists of SEQ ID NO: 14. The two designed ankyrin repeat domains with binding specificity for HER2 bind HER2 at two different epitopes. It is the first recombinant binding protein combining serum albumin-binding and bi-paratopic HER2-binding. The designed ankyrin repeat domain of SEQ ID NO: 14 shows improved storage stability properties (see Example 2 and 3; FIGS. 2A and 2B) compared to known designed ankyrin repeat domains with binding specificity for serum albumin. Said two designed ankyrin repeat domains with binding specificity for serum albumin surprisingly lead to improved pharmacokinetic properties of the recombinant binding protein compared to a corresponding recombinant binding protein having only one designed ankyrin repeat domain with binding specificity for serum albumin (Example 11, FIGS. 5A to 5C). When the two designed ankyrin repeat domains with binding specificity for serum albumin are flanking the other designed ankyrin repeat domains with binding specificity for HER2, the best pharmacokinetic properties are observed (Example 11). The choice of the designed ankyrin repeat domains with binding specificity for HER2 as well as their structural arrangement lead to maximal activity of the compound (Examples 5, 6, and 7). The designed ankyrin repeat domains are connected using a PT-rich linker, surprisingly leading to improved pharmacokinetic properties (Examples 10 and 11). The molecules unites the functionality of at least two drugs (e.g. Trastuzumab and Pertuzumab) in one molecule, and additionally can induce apoptosis in HER2 expressing cells (Example 6, FIG. 7).

In one embodiment, said recombinant binding protein consisting of SEQ ID NO: 21 exhibits improved storage stability compared to a corresponding recombinant binding protein consisting of SEQ ID NO: 22. In one embodiment, said recombinant binding protein consisting of SEQ ID NO: 21 exhibits reduced amounts of degradation products after storage at 40° C. for 1 month at 10 mg/ml in PBS compared to a corresponding recombinant binding protein consisting of SEQ ID NO: 22.

In one embodiment, said recombinant binding protein consisting of SEQ ID NO: 21 exhibits improved pharmacokinetic properties compared to the recombinant binding protein consisting of SEQ ID NO: 21, wherein the C-terminal designed ankyrin repeat domain with binding specificity for serum albumin has been removed. In one embodiment, said recombinant binding protein consisting of SEQ ID NO: 21 exhibits improved pharmacokinetic properties compared to the recombinant binding protein consisting of amino acids 1 to 422 of SEQ ID NO: 21. In one embodiment, said recombinant binding protein consisting of SEQ ID NO: 21 exhibits improved pharmacokinetic properties compared to the recombinant binding protein consisting of SEQ ID NO: 33.

In one embodiment, each of said designed ankyrin repeat domains with binding specificity for serum albumin binds serum albumin of mouse, rat, dog, cynomolgus monkey, or human origin, more preferably serum albumin of mouse, cynomolgus monkey or human origin, more preferably serum albumin of cynomolgus monkey or human origin, more preferably serum albumin of human origin, in PBS with a dissociation constant (Kd) below $10^{-5}$M; preferably below $10^{-6}$M; or more preferably below $10^{-7}$M. In one embodiment, each of said designed ankyrin repeat domains with binding specificity for serum albumin consists of SEQ ID NO: 14 and binds human serum albumin in PBS with a dissociation constant (Kd) below $10^{-5}$M; preferably below $10^{-6}$M; or more preferably below $10^{-7}$M. Examples of dissociation constant determination using surface plasmon resonance are given in Example 5 and in WO2014/083208.

In one embodiment, each of said designed ankyrin repeat domains with binding specificity for HER2 binds HER2 of human origin in PBS with a dissociation constant (Kd) below $10^{-6}$M; preferably below $10^{-7}$M; more preferably below $10^{-8}$M, or more preferably below $10^{-9}$M. In one embodiment, said designed ankyrin repeat domain with binding specificity for HER2 consisting of SEQ ID NO: 16 binds human HER2 in PBS with a dissociation constant (Kd) below $10^{-6}$M; preferably below $10^{-7}$M; more preferably below $10^{-8}$M, more preferably below $10^{-9}$M, more preferably below $10^{-10}$M, or more preferably below $10^{-11}$M. In one embodiment, said designed ankyrin repeat domain with binding specificity for HER2 consisting of SEQ ID NO: 17 binds human HER2 in PBS with a dissociation constant (Kd) below $10^{-6}$M; preferably below $10^{-7}$M; more preferably below $10^{-8}$M, or more preferably below $10^{-9}$M.

In one embodiment, said recombinant binding protein binds HER2 of human origin in PBS with a dissociation constant (Kd) below $10^{-7}$M; preferably below $10^{-8}$M; more preferably below $10^{-9}$M, or more preferably below $10^{-10}$M. In one embodiment, said recombinant binding protein with binding specificity for HER2 comprising SEQ ID NO: 32 binds human serum albumin in PBS with a dissociation constant (Kd) below $10^{-8}$M; preferably below $10^{-9}$M, or more preferably below $10^{-10}$M. In one embodiment, said recombinant binding protein with binding specificity for HER2 comprising SEQ ID NO: 21 binds HER2 of human origin in PBS with a dissociation constant (Kd) below $10^{-7}$M; preferably below $10^{-8}$M; more preferably below $10^{-9}$M, or more preferably below $10^{-10}$M. In one embodiment, said recombinant binding protein with binding specificity for HER2 consisting of SEQ ID NO: 21 binds HER2 of human origin in PBS with a dissociation constant (Kd) below $10^{-7}$M; preferably below $10^{-8}$M; more preferably below $10^{-9}$M, or more preferably below $10^{-10}$M. In one embodiment, said recombinant binding protein binds human serum albumin with a dissociation constant (Kd) below $10^{-5}$M, preferably below $10^{-6}$M, or more preferably below $10^{-7}$M. In one embodiment, said recombinant binding protein with binding specificity for HER2 comprising SEQ ID NO: 21 binds human serum albumin in PBS with a dissociation constant (Kd) below $10^{-5}$M; preferably below $10^{-6}$M, or more preferably below $10^{-7}$M. In one embodiment, said recombinant binding protein with binding specificity for HER2 consisting of SEQ ID NO: 21 binds human serum albumin in PBS with a dissociation constant (Kd) below $10^{-5}$M; preferably below $10^{-6}$M, or more preferably below $10^{-7}$M.

In one embodiment, said recombinant binding protein inhibits cell proliferation of HER2-expressing cells with an inhibition constant (IC$_{50}$) below $10^{-6}$M; preferably below $10^{-7}$M, or more preferably below $10^{-8}$M. Examples of such cells include BT474, SKBR-3, SKOV-3, NCI-N87, ZR-75-30, HCC1419, or MDA-MB175 cells. In one embodiment, said recombinant binding protein inhibits BT474 cell proliferation with an inhibition constant (IC$_{50}$) below $10^{-6}$M; preferably below $10^{-7}$M, or more preferably below $10^{-8}$M. In one embodiment, the recombinant binding protein comprising SEQ ID NO: 32 inhibits BT474 cell proliferation with an inhibition constant (IC$_{50}$) below $10^{-6}$M; preferably below $10^{-7}$M, or more preferably below $10^{-8}$M. In one embodiment, the recombinant binding protein comprising SEQ ID NO: 21 inhibits BT474 cell proliferation with an inhibition constant (IC$_{50}$) below $10^{-6}$M; preferably below $10^{-7}$M, or more preferably below $10^{-8}$M. In one embodiment, the recombinant binding protein consisting of SEQ ID NO: 21 inhibits BT474 cell proliferation with an inhibition constant (IC$_{50}$) below $10^{-6}$M; preferably below $10^{-7}$M, or more preferably below $10^{-8}$M. Cell inhibition assays are well known in the field. In one embodiment, said recombinant binding protein consisting of SEQ ID NO: 21 inhibits BT474 cell proliferation more potently than the recombinant binding protein having only one designed ankyrin repeat domain with binding specificity for HER2. In one embodiment, said recombinant binding protein consisting of SEQ ID NO: 21 inhibits BT474 cell proliferation without the aid of antibody-dependent cell-mediated cytotoxicity (ADCC; well known to the practitioner in the art). In one embodiment, said recombinant binding protein consisting of SEQ ID NO: 21 inhibits BT474 cell proliferation without the aid if an IgG1-Fc fragment.

In one embodiment, said recombinant binding protein comprising, preferably consisting of, SEQ ID NO: 21 induces apoptosis in BT474 cells. In one embodiment, said recombinant binding protein comprising, preferably consisting of, SEQ ID NO: 21 induces apoptosis in BT474 cells with an half maximal effective concentration (EC$_{50}$) value of smaller than 100 nM. Preferably, said recombinant binding protein induces apoptosis in BT474 cells with an EC50 value of smaller than 90, 80, 70, 60, 50, 40, 30, 20 or 10 nM. Preferably, said recombinant binding protein at 100 nM induces apoptosis in BT474 to a greater extent than 100 nM Trastuzumab, 100 nM Pertuzumab, or a mixture of 100 nM Trastuzumab and 100 nM Pertuzumab. In one embodiment, said recombinant binding protein comprising, preferably consisting of, SEQ ID NO: 21 induces apoptosis in HER2 expressing cells.

In one embodiment, said recombinant binding protein comprising SEQ ID NO: 21 inhibits the RAS pathway. In one embodiment, HER2 in BT474 is less phosphorylated when treated with said recombinant binding protein comprising SEQ ID NO: 21 than when treated with Trastuzumab.

In one embodiment, said recombinant binding protein is able to bind HER2 and human serum albumin simultaneously. In one embodiment, said recombinant binding protein is able to bind two molecules of human serum albumin simultaneously. Such simultaneous binding can be shown using surface plasmon resonance experiments (Example 5) or size-exclusion chromatography coupled to static light scattering (Example 14), techniques well-known to the person skilled in the art.

In one embodiment, said recombinant binding protein is binding HER2 in a bi-paratopic mode. In one embodiment, said recombinant binding protein binds HER2 at two different epitopes.

In one embodiment, the present invention relates to a recombinant binding protein comprising a first, a second, a third, and a fourth designed ankyrin repeat domain, wherein said first and second designed ankyrin repeat domains each have binding specificity for HER2, and wherein said third and fourth designed ankyrin repeat domains each have binding specificity for serum albumin. Preferably, said recombinant binding protein consists of a single polypeptide chain. More preferably, said first, second, third and fourth designed ankyrin repeat domain are linked by polypeptide linkers. SEQ ID NO: 21 is an example of such a recombinant binding protein.

In one embodiment, said first designed ankyrin repeat domain with binding specificity for HER2 is binding domain II of HER2. In one embodiment, said second designed ankyrin repeat domain with binding specificity for HER2 is binding domain IV of HER2. In one embodiment, said first designed ankyrin repeat domain with binding specificity for HER2 is binding domain II of HER2, and said second designed ankyrin repeat domain with binding specificity for HER2 is binding domain IV of HER2. In one embodiment, said first designed ankyrin repeat domain with binding specificity for HER2 comprises SEQ ID NO: 16. In one embodiment, said second designed ankyrin repeat domain with binding specificity for HER2 comprises SEQ ID NO: 17. In one embodiment, said first designed ankyrin repeat domain with binding specificity for HER2 comprises SEQ ID NO: 16 and said second designed ankyrin repeat domain with binding specificity for HER2 comprises SEQ ID NO: 17.

In one embodiment, said first designed ankyrin repeat domain with binding specificity for HER2 comprising SEQ ID NO: 16 binds human HER2 in PBS with a dissociation constant (Kd) below $10^{-6}$M; preferably below $10^{-7}$M; more preferably below $10^{-8}$M, more preferably below $10^{-9}$M, more preferably below $10^{-10}$M, or more preferably below $10^{-11}$M. In one embodiment, said second designed ankyrin repeat domain with binding specificity for HER2 comprising SEQ ID NO: 17 binds human HER2 in PBS with a dissociation constant (Kd) below $10^{-6}$M; preferably below $10^{-7}$M; more preferably below $10^{-8}$M, or more preferably below $10^{-9}$M.

In one embodiment, each of said third and fourth designed ankyrin repeat domains with binding specificity for serum albumin binds human serum albumin in PBS with a dissociation constant (Kd) below $10^{-5}$M, preferably below $10^{-6}$M, or more preferably below $10^{-7}$M. In one embodiment, said third and fourth designed ankyrin repeat domains with binding specificity for serum albumin, each comprising SEQ ID NO: 14, each bind human serum albumin in PBS with a dissociation constant (Kd) below $10^{-5}$M; preferably below $10^{-6}$M; or more preferably below $10^{-7}$M.

The terms "first, "second", "third", and optionally "fourth", used in "first designed ankyrin repeat domain", "second designed ankyrin repeat domain", "third designed ankyrin repeat domain", and "fourth designed ankyrin repeat domain", do not indicate or imply any positional arrangement of said designed ankyrin repeat domains within the recombinant binding protein. In one embodiment, said four designed ankyrin repeat domains are positioned from N to C terminus: Third—first—second—fourth.

In one embodiment, the recombinant binding protein inhibits BT474 cell proliferation in a tumor xenograft model in mice. In one embodiment, the recombinant binding protein inhibits tumor growth in a HER2-expressing patient-derived xenograft cancer model in mice. In one embodiment, the recombinant binding protein inhibits tumor growth in a HER2-expressing patient-derived xenograft gastric cancer model in mice. The term "HER2-expressing patient-derived xenograft" has the meaning of a patient-derived cancer tissue xenograft, wherein in said tissue at least one cell expresses HER2 above background.

In any embodiment of the present invention relating to a designed ankyrin repeat domain or a recombinant binding protein comprising an amino acid sequence that has at least 88%, 89%, 90%, 91%, 92%, 93%, 94%, 95%, 96%, 97%, 98%, 99%, or 100% amino acid sequence identity to a given amino acid sequence, the non-identical amino acids may be located at any position of the designed ankyrin repeat domain or the recombinant binding protein.

Likewise, in any embodiment of the present invention relating to a designed ankyrin repeat domain or a recombinant binding protein in which up to 72, 71, 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1, or 0 amino acids are exchanged by any amino acid, the exchanged amino acids amino acids may be located at any position of the designed ankyrin repeat domain. The techniques to modify, e.g. by point mutation, a recombinant binding protein of the present invention are well known to the person skilled in the art. Starting from SEQ ID NO: 21, a person skilled in the art knows how and where to exchange amino acids (e.g. using the knowledge of WO2002/020565) to create sequence variants of SEQ ID NO: 21 with high likelihood of unaltered functional activity.

In one embodiment, said recombinant binding protein exhibits an increase in terminal half-life, preferably an increase in terminal half-life of at least 5%, 10%, 15%, 20%, 25%, 30%, 35%, 40%, or 45%, compared to a corresponding recombinant binding protein lacking said fourth designed ankyrin repeat domain with binding specificity for serum albumin. In one embodiment, said recombinant binding protein exhibits an increase in terminal half-life, preferably an increase in terminal half-life of at least 5%, 10%, 15%, 20%, 25%, 30%, 35%, 40%, or 45%, compared to a corresponding recombinant binding protein comprising only one designed ankyrin repeat domain with binding specificity for serum albumin. Examples of such an increase in terminal half-life are given in Example 11.

In one embodiment, said recombinant binding protein comprising, preferably consisting of, SEQ ID NO: 21 exhibits a terminal half-life of about 47 hours at 1 mg/kg in cynomolgus monkey. In one embodiment, said recombinant binding protein comprising, preferably consisting of, SEQ ID NO: 21 exhibits a terminal half-life of about 100 hours at 5 mg/kg in cynomolgus monkey. In one embodiment, said recombinant binding protein comprising, preferably consisting of, SEQ ID NO: 21 exhibits a terminal half-life of more than 100 hours at 10 mg/kg in cynomolgus monkey. In one embodiment, the recombinant binding protein comprising, preferably consisting of, SEQ ID NO: 21 exhibits a terminal half-life of more than 100 hours at 100 mg/kg in cynomolgus monkey.

In one embodiment, the invention relates to a nucleic acid encoding the amino acid sequence of a designed ankyrin repeat domain or a recombinant binding protein of the present invention, preferably a recombinant binding protein of the present invention. In one embodiment, the invention relates to a nucleic acid encoding the amino acid sequence of a recombinant binding protein of the present invention. In one embodiment, the invention relates to a nucleic acid encoding the amino acid sequence consisting of SEQ ID NO: 21. In one embodiment, the invention relates to a nucleic acid encoding said recombinant binding protein. In one embodiment, the invention relates to a nucleic acid encoding the recombinant binding protein consisting of SEQ ID NO: 21. Furthermore, the invention relates to vectors comprising any nucleic acid of the invention. Nucleic acids are well known to the skilled person. In the examples, nucleic acids were used to produce designed ankyrin repeat domains or recombinant binding proteins of the invention in E. coli.

In one embodiment, the invention relates to a pharmaceutical composition comprising a recombinant binding protein and/or a designed ankyrin repeat domain of the present invention, and/or a nucleic acid encoding a recombinant binding protein and/or a designed ankyrin repeat domain of the present invention, and optionally a pharmaceutically acceptable carrier and/or diluent.

In one embodiment, the invention relates to a pharmaceutical composition comprising a recombinant binding protein or a nucleic acid encoding a recombinant binding protein, and optionally a pharmaceutically acceptable carrier and/or diluent.

Pharmaceutical acceptable carriers and/or diluents are known to the person skilled in the art and are explained in more detail below. Even further, a diagnostic composition is considered comprising one or more of the above mentioned recombinant binding proteins and/or designed ankyrin repeat domains, and/or nucleic acids, in particular recombinant binding proteins and/or nucleic acids.

A pharmaceutical composition comprises a recombinant binding protein, and/or a designed ankyrin repeat domain, and/or a nucleic acid, preferably a recombinant binding protein and/or a nucleic acid, as described herein and a pharmaceutically acceptable carrier, excipient or stabilizer, for example as described in Remington's Pharmaceutical Sciences 16$^{th}$ edition, Osol, A. Ed., 1980. Suitable carriers, excipients or stabilizers known to the skilled man are saline, Ringer's solution, dextrose solution, Hank's solution, fixed oils, ethyl oleate, 5% dextrose in saline, substances that enhance isotonicity and chemical stability, buffers and preservatives. Other suitable carriers include any carrier that does not itself induce the production of antibodies harmful to the individual receiving the composition such as proteins, polysaccharides, polylactic acids, polyglycolic acids, polymeric amino acids and amino acid copolymers. A pharmaceutical composition may also be a combination formulation, comprising an additional active agent, such as an anti-cancer agent or an anti-angiogenic agent, or an additional bioactive compound.

One embodiment of the present invention relates to the use of a recombinant binding protein of the present invention comprising two designed ankyrin repeat domains with binding specificity for serum albumin for manufacturing a pharmaceutical composition, wherein said recombinant binding protein exhibits an increased terminal half-life, preferably an increased terminal half-life of at least 5%, preferably 10%, 15%, 20%, 25%, 30%, 35%, 40%, 45%, 50%, 60%, 70%, 80%, 90%, 100%, 150%, 200%, or 250%, compared to a corresponding recombinant binding protein comprising only one designed ankyrin repeat domain with binding specificity for serum albumin.

In one embodiment, a pharmaceutical composition comprises at least one recombinant binding protein as described herein and a detergent such as nonionic detergent, a buffer such as phosphate, and a sugar such as sucrose. In one embodiment, such a composition comprises recombinant binding proteins as described above and PBS.

In one embodiment, the invention relates to the use of a pharmaceutical composition, or a recombinant binding protein according to the present invention for the treatment of a disease. For that purpose, the pharmaceutical composition, or the recombinant binding protein according to the present invention is administered, to a patient in need thereof, in a therapeutically effective amount. Administration may include topical administration, oral administration, and parenteral administration. The typical route of administration is parenteral administration. In parental administration, the pharmaceutical composition of this invention will be formulated in a unit dosage injectable form such as a solution, suspension or emulsion, in association with the pharmaceutically acceptable excipients as defined above. The dosage and mode of administration will depend on the individual to be treated and the particular disease.

Further, any of the above mentioned pharmaceutical composition or recombinant binding protein is considered for the treatment of a disorder.

In one embodiment, said recombinant binding protein or such other pharmaceutical composition described herein is applied intravenously. For parenteral application, the recombinant binding protein or said pharmaceutical composition can be injected as bolus injection or by slow infusion at a therapeutically effective amount.

In one embodiment, the invention relates to a method of treatment of a medical condition, the method comprising the step of administering, to a patient in need of such a treatment, a therapeutically effective amount of a recombinant binding protein of the invention. In one embodiment, the invention relates to a method of treatment of a medical condition, the method comprising the step of administering, to a patient in need of such a treatment, a therapeutically effective amount of a pharmaceutical composition of the invention. Example 7 (FIGS. 4A to 4E) illustrates the utility of the use of a recombinant binding protein comprising SEQ ID NO: 21 for the treatment of cancer. In one embodiment, the invention relates to the use of a pharmaceutical composition of the present invention for the treatment of a disease. In one embodiment, the invention relates to a pharmaceutical composition for use in the treatment of a disease. In one embodiment, the invention relates to a pharmaceutical composition for use in the treatment of a medical condition.

In one embodiment, the invention relates to the recombinant binding protein consisting of SEQ ID NO: 21 for use as a medicament. In one embodiment, the invention relates to the recombinant binding protein consisting of SEQ ID NO: 21 for use in the treatment of a disease. In one embodiment, said pharmaceutical composition, recombinant binding protein, or nucleic acid molecule is considered for use in the treatment of a disease. In one embodiment, the invention relates to a medicament comprising said pharmaceutical composition, recombinant binding protein, or nucleic acid molecule. In one embodiment, the invention relates to the use of the recombinant binding protein consisting of SEQ ID NO: 21 in a pharmaceutical composition for the treatment of a disease. In one embodiment, the invention relates to said pharmaceutical composition for use in the treatment of a disease. In one embodiment, the invention relates to said recombinant binding protein for use in the treatment of a disease. In one embodiment, the invention relates to said nucleic acid for use in the treatment of a disease. In one embodiment, the invention relates to the use of said pharmaceutical composition, recombinant binding protein, or nucleic acid molecule, as medicament for the treatment of a disease. In one embodiment, the invention relates to the use of said pharmaceutical composition, recombinant binding protein, or nucleic acid molecule, for the treatment of a disease. In one embodiment, the invention relates to the use of said pharmaceutical composition, recombinant binding protein, or nucleic acid molecule, for manufacturing of a medicament. In one embodiment, the invention relates to the use of said pharmaceutical composition, recombinant binding protein, or nucleic acid molecule, for manufacturing of a medicament for the treatment of a disease. In one embodiment, the invention relates to a process for the manufacturing of a medicament for the treatment of a disease, wherein said pharmaceutical composition, recombinant binding protein, or nucleic acid molecule is active ingredient of the medicament. In one embodiment, the invention relates to a process of treatment of a disease using said pharmaceutical composition, recombinant binding protein, or nucleic acid molecule.

The term "medical condition" (or disorder or disease) includes autoimmune disorders, inflammatory disorders, retinopathies (particularly proliferative retinopathies), neurodegenerative disorders, infections, metabolic diseases, and neoplastic diseases. Any of the recombinant binding proteins described herein may be used for the preparation of a medicament for the treatment of such a disorder, particularly a disorder selected from the group comprising: an autoimmune disorder, an inflammatory disorder, a retinopathy, and a neoplastic disease. A "medical condition" may be one that is characterized by inappropriate cell proliferation. A medical condition may be a hyperproliferative condition. The invention particularly relates to a method of treating a medical condition, the method comprising the step of administering, to a patient in need of such treatment, a therapeutically effective amount of a recombinant binding protein or said pharmaceutical composition of the invention. In a preferred embodiment said medical condition is a neoplastic disease. The term "neoplastic disease", as used herein, refers to an abnormal state or condition of cells or tissue characterized by rapidly proliferating cell growth or neoplasm. In one embodiment said medical condition is a malignant neoplastic disease. In one embodiment said medical condition relates to cancer. In one embodiment said medical condition relates to HER2 expressing cancer, HER2 addicted cancer, partially HER2 addicted cancer, HER2 overexpressing cancer, HER2 amplified cancer, Trastuzumab-resistant cancer, and/or Trastuzumab-sensitive cancer. In one embodiment said medical condition relates to breast cancer and/or gastro-intestinal cancer and/or brain cancer. In one embodiment said medical condition relates to breast cancer, ovarian cancer, gastric cancer, stomach cancer, uterine cancer, colorectal cancer, bladder cancer, and/or HER2 overexpressing cancer. The term "brain cancer" may relate to brain metastasis of HER2 overexpressing cancer, brain metastasis of HER2 amplified cancer, HER2 overexpressing brain cancer, or HER2 amplified brain cancer. The term "gastro-intestinal" cancer may relate to gastric cancer, esophageal cancer, colorectal cancer, biliary gland cancer, gallbladder cancer, or pancreatic adenocarcinoma. The term "therapeutically effective amount" means an amount that is sufficient to produce a desired effect on a patient. In one embodiment, the said medical condition relates to cancer, wherein cells of said cancer exhibit HER2 expression levels above background as determined by IHC. In one embodiment, the said medical condition relates to cancer, wherein cells of said cancer exhibit HER2 expression levels above that of healthy cells in their vicinity as determined by IHC. Such HER2 expression levels above background are well-known to the practitioner in the art, e.g. from assays such as the HercepTest® (Dako). Preferably, HER2 expression levels above background relate to a HercepTest® score of 1+, 2+, or 3+, more preferably 2+, or 3+. Her2-overexpression is well-known to the practitioner in the art (Rüschoff et al., 2012. Modern Pathology 25, 637-650; Wolff et al., 2013. J. Clin. Oncol. 31 (31), 3997-4014).

In particular, the invention relates to the treatment of a medical condition using a pharmaceutical composition of the present invention, wherein said medical condition is cancer.

The use of a recombinant binding protein of the present invention or said pharmaceutical compositions for the treatment of cancer diseases can also be in combination with one or more other therapy known in the art. The term "use in combination with", as used herein, shall refer to a co-administration, which is carried out under a given regimen. This includes synchronous administration of the different compounds as well as time-shifted administration of the different compounds (e.g. compound A is given once and compound B is given several times thereafter, or vice versa, or both compounds are given synchronously and one of the two is also given at later stages). Examples of compounds that can for example be co-administered comprise taxanes, anthracyclines, platinum-based chemotherapeutics, 5-FU, PI3K inhibitors (such as for example Apitolisib, Taselisib, or Alpelisib), MEK inhibitors (such as for example Trametinib, or Cobimetinib), RAS inhibitors (such as for example Salirasib), RAF inhibitors, mTOR inhibitors (including for example Apitolisib and Everolimus), Pan-EGFR inhibitors, microtubule inhibitors (including eribulin), targeted therapies including cell cycle kinase inhibitors (such as for example Palbociclib), HER2 inhibitors, Trastuzumab, Trastuzumab-DM1, Pertuzumab, Cetuximab, Panitumumab, Nimotuzumab, Bevacizumab, Ranibizumab, MP0250, Ipilimumab, Pembrolizumab, Nivolumab, Urelumab, Utolimumab, or Atezolizumab. Preferably these compounds are used at recommended doses. In one embodiment said recombinant binding protein comprising SEQ ID NO: 21 potentiates the effect of PI3K inhibitors, mTOR inhibitors, Eribulin, Trastuzumab, or Lapatinib. In one embodiment said recombinant binding protein comprising SEQ ID NO: 21 enables the use of lower doses of PI3K inhibitors, mTOR inhibitors, Eribulin, Trastuzumab, or Lapatinib for the treatment of disease. Examples of such combinations are given in Example 17.

In a further embodiment, the invention relates to the use of a recombinant binding protein of the invention for the manufacture of a medicament that is used for the treatment of a medical condition, preferably a neoplastic disease, more preferably cancer.

In one embodiment, the invention relates to the use of a pharmaceutical composition of the invention for the manufacture of a medicament that is used for the treatment of a medical condition, which may be a neoplastic disease, in particular cancer.

The formulations to be used for in vivo administration must be aseptic or sterile. This is readily accomplished by filtration through sterile filtration membranes.

In one embodiment the invention relates to a recombinant binding protein comprising any of the above mentioned repeat domains.

In one embodiment, the invention relates to a kit comprising said recombinant binding protein. In one embodiment, the invention relates to a kit comprising a nucleic acid encoding said recombinant binding protein. In one embodiment, the invention relates to a kit comprising said pharmaceutical composition. In one embodiment, the invention relates to a kit comprising said recombinant binding protein, and/or a nucleic acid encoding said recombinant binding protein, and/or said pharmaceutical composition. In one embodiment, the invention relates to a kit comprising the recombinant binding protein comprising, preferably consisting of, SEQ ID NO: 21, and/or a nucleic acid encoding the recombinant binding protein comprising, preferably consisting of, SEQ ID NO: 21, and/or a pharmaceutical composition comprising the recombinant binding protein comprising, preferably consisting of, SEQ ID NO: 21 and/or a nucleic acid encoding the recombinant binding protein comprising, preferably consisting of, SEQ ID NO: 21.

In one embodiment, the invention relates to a method for producing a recombinant binding protein of the present invention. In one embodiment, the invention relates to a method for producing the recombinant binding protein comprising, preferably consisting of, SEQ ID NO: 21, the method comprising the steps of (i) expressing said recombinant binding protein in bacteria, and (ii) purifying said recombinant binding protein using chromatography. Said method may comprise additional steps. Such a method of producing a recombinant binding protein of the present invention is given in Example 1.

The invention is not restricted to the particular embodiments described in the Examples. Other sources may be used and processed following the general outline described below.

A number of documents are cited throughout this specification. The disclosure content of these documents is herewith incorporated by reference.

This specification refers to a number of amino acid sequences of the amino acid sequence listing of this specification named "P015_Sequence_Listing.txt" and the amino acid sequences of the sequence protocol are herewith incorporated by reference.

Definitions

In the context of the present invention the term "protein" refers to a polypeptide, wherein at least part of the polypeptide has, or is able to acquire a defined three-dimensional arrangement by forming secondary, tertiary, or quaternary structures within a single polypeptide chain and/or between multiple polypeptide chains. If a protein comprises two or more polypeptide chains, the individual polypeptide chains may be linked non-covalently or covalently, e.g. by a disulfide bond between two polypeptides. A part of a protein, which individually has, or is able to acquire, a defined three-dimensional arrangement by forming secondary or tertiary structure, is termed "protein domain". Such protein domains are well known to the practitioner skilled in the art.

The term "recombinant" as used in recombinant protein, recombinant protein domain, recombinant binding protein and the like, means that said polypeptides are produced by the use of recombinant DNA technologies well known by the practitioner skilled in the relevant art. For example, a recombinant DNA molecule (e.g. produced by gene synthesis) encoding a polypeptide can be cloned into a bacterial expression plasmid (e.g. pQE30, QIAgen), yeast expression plasmid, mammalian expression plasmid, or plant expression plasmid, or a DNA enabling in vitro expression. If, for example, such a recombinant bacterial expression plasmid is inserted into an appropriate bacteria (e.g. Escherichia coli), this bacteria can produce the polypeptide encoded by this recombinant DNA. The correspondingly produced polypeptide is called a recombinant polypeptide or recombinant protein.

In the context of the present invention, the term "binding protein" refers to a protein comprising two or more, preferably three or more, more preferably four or more binding domains. Preferably, said binding protein is a recombinant binding protein. Preferably, said binding protein comprises four repeat domains. More preferably, said binding protein comprises four designed ankyrin repeat domains. Preferably, two of said binding domains of said binding protein each have a target specificity for serum albumin. Also preferably, two of said binding domains of said binding protein each have a target specificity for HER2.

Furthermore, any such binding protein may comprise additional polypeptides (such as e.g. polypeptide tags, polypeptide linkers, fusion to other binding proteinaceous domains, cytokines, hormones, or antagonists), or chemical modifications (such as coupling to polyethylene-glycol, toxins (e.g. DM1 from Immunogen), small molecules, antibiotics and alike) well known to the person skilled in the art.

The term "binding domain" means a protein domain exhibiting the same "fold" (i.e. secondary, tertiary, and/or quaternary structure) as a protein scaffold and having a predetermined property, as defined below. Such a binding domain may be obtained by rational, or most commonly, combinatorial protein engineering techniques, skills which are known in the art (Binz, H. K., Amstutz, P., Plückthun, A., 2005. Nat. Biotech. 23, 1257-1268). For example, a binding domain having a predetermined property can be obtained by a method comprising the steps of (a) providing a diverse collection of protein domains exhibiting the same fold as a protein scaffold as defined further below; and (b) screening said diverse collection and/or selecting from said diverse collection to obtain at least one protein domain having said predetermined property. The diverse collection of protein domains may be provided by several methods in accordance with the screening and/or selection system being used, and may comprise the use of methods well known to the person skilled in the art, such as phage display or ribosome display. Preferably, said binding domain is a recombinant binding domain.

The term "protein scaffold" means a protein with exposed surface areas in which amino acid insertions, substitutions or deletions are highly tolerable. Examples of protein scaffolds that can be used to generate binding domains of the present invention are antibodies or fragments thereof such as single-chain Fv or Fab fragments, protein A from Staphylococcus aureus, the bilin binding protein from Pieris brassicae or other lipocalins, ankyrin repeat proteins or other repeat proteins, and human fibronectin. Protein scaffolds are known to the person skilled in the art (Binz et al., 2005, loc. cit.; Binz et al., 2004, loc. cit.).

The term "target" refers to an individual molecule such as a nucleic acid molecule, a polypeptide or protein, a carbohydrate, or any other naturally occurring molecule, including any part of such individual molecule, or complexes of two or more of such molecules. A target may be a whole cell or a tissue sample, or it may be any non-natural compound. Preferably, a target is a naturally occurring or non-natural polypeptide or a polypeptide containing chemical modifications, for example modified by natural or non-natural phosphorylation, acetylation, or methylation. In the particular application of the present invention, the targets are serum albumin and HER2.

The term "predetermined property" refers to a property such as binding to a target, blocking of a target, activation of a target-mediated reaction, enzymatic activity, and related further properties. Depending on the type of desired property, one of ordinary skill will be able to identify format and necessary steps for performing screening and/or selection of a binding domain with the desired property. Preferably, said predetermined property is specifically binding to a target.

In the context of the present invention, the term "polypeptide" relates to a molecule consisting of a chain of multiple, i.e. two or more, amino acids linked via peptide bonds. Preferably, a polypeptide consists of more than eight amino acids linked via peptide bonds. The term "polypeptide" also includes multiple chains of amino acids, linked together by S—S bridges of cysteines. Polypeptides are well-known to the person skilled in the art.

The term "polypeptide tag" refers to an amino acid sequence attached to a polypeptide/protein, wherein said amino acid sequence is useful for the purification, detection, or "targeting" (i.e. localization to the site of a target) of said polypeptide/protein, or wherein said amino acid sequence improves the physicochemical behavior of the polypeptide/protein, or wherein said amino acid sequence possesses an effector function. The individual polypeptide tags of a binding protein may be connected to other parts of the binding protein directly or via polypeptide linkers. These polypeptide tags are all well known in the art and are fully available to the person skilled in the art. Examples of polypeptide tags are small polypeptide sequences, for example, His (e.g. the His-tag of SEQ ID NO: 1), myc, FLAG, or Strep-tags, or polypeptides such as enzymes (for example alkaline phosphatase), which allow the detection of said polypeptide/protein, or polypeptides which can be used for targeting (such as immunoglobulins or fragments thereof) and/or as effector molecules.

The term "polypeptide linker" refers to an amino acid sequence, which is able to link, for example, two protein domains, a polypeptide tag and a protein domain, a protein domain and a non-proteinaceous compound or polymer such as polyethylene glycol, or two sequence tags. Such additional domains, tags, non-proteinaceous compounds or polymers and linkers are known to the person skilled in the relevant art. A list of examples is provided in the description of patent application WO2002/020565. Particular examples of such linkers are glycine-serine-linkers and proline-threonine-linkers of variable lengths. Examples of glycine-serine-linkers are GS and amino acid sequences provided in SEQ ID NOs: 2 to 6, and examples of proline-threonine-linkers are provided in amino acid sequences SEQ ID NOs: 7 to 9.

Patent application WO2002/020565 and Forrer et al., 2003 (Forrer, P., Stumpp, M. T., Binz, H. K., Plückthun, A., 2003. FEBS Letters 539, 2-6), contain a general description of repeat protein features and repeat domain features, techniques and applications. The term "repeat protein" refers to a protein comprising one or more repeat domains. Preferably, a repeat protein comprises up to six repeat domains. More preferably, a repeat protein comprises up to five repeat domains. More preferably, a repeat protein comprises up to four repeat domains. Furthermore, said repeat protein may comprise additional non-repeat protein domains, polypeptide tags and/or polypeptide linkers. The repeat domains can be binding domains as described hereinbefore.

The term "repeat domain" refers to a protein domain comprising two or more consecutive repeat modules as structural units, wherein said structural units have the same fold, and stack tightly to create a superhelical structure having a joint hydrophobic core. Next to a structural homology, such repeat modules further have a sequence homology. Preferably, a repeat domain further comprises an N-terminal and/or a C-terminal capping repeat. For clarity, a capping repeat can be a repeat module. Such repeat domains, repeat modules, and capping repeats, sequence motives, as well as structural homology and sequence homology are well known to the practitioner in the art from examples of ankyrin repeat domains (WO2002/020565), leucine-rich repeat domains (WO2002/020565), tetratricopeptide repeat domains (Main, E. R., Xiong, Y., Cocco, M. J., D'Andrea, L., Regan, L., Structure 11(5), 497-508, 2003), and armadillo repeat domains (WO2009/040338). It is further well known to the practitioner in the art, that such repeat domains are different from proteins comprising repeated amino acid sequences, where every repeated amino acid sequence is able to form an individual domain (for example FN3 domains of Fibronectin), or where the repeated amino acid sequences are no structural units, i.e. said repeated amino acid sequences do not stack tightly to create a superhelical structure having a joint hydrophobic core. Methods for identifying and determining repeat modules or repeat sequence motifs or for identifying families of related proteins comprising such repeat units or motifs, such as homology searches (BLAST® etc.), are well established in the field of bioinformatics, and are well known to the practitioner in the art.

The term "designed repeat protein" and "designed repeat domain" refer to a repeat protein or repeat domain, respectively, obtained as the result of an inventive procedure, e.g. as explained in patent application WO2002/020565. The term "designed" refers to the property that such repeat proteins and repeat domains, respectively, are man-made, synthetic and not from nature. The designed repeat proteins or designed repeat domains of WO2002/020565 include designed ankyrin repeat proteins or designed ankyrin repeat domains, respectively. Accordingly, a designed ankyrin repeat protein herein corresponds to protein of the invention comprising at least one designed ankyrin repeat domain. Further, the term "not from nature" means that the sequence of said binding protein or said binding domain is not present as a non-artificial sequence entry in a sequence database, for example in GenBank, EMBL-Bank or Swiss-Prot. These databases and other similar sequence databases are well known to the person skilled in the art. The recombinant binding proteins or designed ankyrin repeat domains of the invention are non-naturally occurring.

The terms "repeat module", "repeat unit", "capping repeat", "capping module", and further terms relating to repeat proteins and repeat domains, are defined in WO2002/020565, and the definitions are incorporated by reference.

The term "has binding specificity for a target", "specifically binding to a target", "binding to a target with high specificity", "specific for a target" or "target specificity" and the like means that a binding protein or binding domain binds in PBS to a target with a lower dissociation constant (i.e. it binds with higher affinity) than it binds to an unrelated protein such as the *E. coli* maltose binding protein (MBP). Preferably, the dissociation constant ("Kd") in PBS for the target is at least $10^2$; more preferably, at least $10^3$; more preferably, at least $10^4$; or more preferably, at least $10^5$ times lower than the corresponding dissociation constant for MBP. Methods to determine dissociation constants of protein-protein interactions, such as surface plasmon resonance (SPR) based technologies (e.g. SPR equilibrium analysis) or isothermal titration calorimetry (ITC) are well known to the person skilled in the art. The measured Kd values of a particular protein-protein interaction can vary if measured under different conditions (e.g., salt concentration, pH). Thus, measurements of Kd values are preferably made with standardized solutions of protein and a standardized buffer, such as PBS.

The term "PBS" means a phosphate buffered water solution containing 137 mM NaCl, 10 mM phosphate and 2.7 mM KCl and having a pH of 7.4.

The term "inhibit cell proliferation" and alike in the context of the present invention refers to the ability of said recombinant binding protein to inhibit cell proliferation. The strength of inhibition is typically measured by assessing the concentration of half-maximal inhibition ($IC_{50}$). The term inhibition and the assessment of $IC_{50}$ values are well established in the field.

The term "mouse serum albumin" refers to UniProt accession number P07724, the term "cynomolgus monkey serum albumin" (i.e. *Macaca fascicularis*) refers to UniProt accession number A2V9Z4, and the term "human serum albumin" refers to UniProt accession number P02768.

HER2, as used herein, relates to Human Epidermal Growth Factor Receptor 2, also known as Neu, ErbB-2, CD340 (cluster of differentiation 340) or p185. HER2 is a member of the epidermal growth factor receptor (EGFR/ErbB) family. HER2 is, in humans, encoded by ERBB2, a known proto-oncogene located at the long arm of human chromosome 17 (17q12). HER2 has the UniProtKB/Swiss-Prot number P04626. Human HER2 consists of 1255 amino acids with a 21 amino acid signal sequence, a 631 amino acid extracellular region (e.g. the ectodomain comprising domains I to IV), a 23 amino acid transmembrane region, and a 580 amino acid cytoplasmic domain.

"Improved storage stability" in the context of the present invention means the reduction of the amounts of a degradation band, preferably the reduction of the amount of degradation products, as detected by a Coomassie-stained SDS-PAGE occurring after storage at 40° C. for 1 month at 10 mg/ml in PBS, by at least 5%, 10%, 15%, 20%, 25%, 30%, 35%, 40%, 45%, 50%, or 50%. Methods to assess storage stability by SDS-PAGE are well known to the person skilled in the art. Examples of designed ankyrin repeat domains and recombinant binding proteins with improved storage stability properties are given in Examples 2 and 3.

The expression "the recombinant binding protein comprising only one designed ankyrin repeat domain with binding specificity for serum albumin", means a recombinant binding that has the composition of a recombinant binding protein of the present invention in which the number of designed ankyrin repeat domains with binding specificity for serum albumin is reduced to one, by removing all designed ankyrin repeat domains with binding specificity for serum albumin but one, and the corresponding polypeptide linkers.

The term "bi-paratopic binding protein" means a binding protein directed against two different epitopes located on the same target protein. For example, a bi-paratopic binding protein targeting HER2 comprises at least a first binding domain targeting a first epitope on HER2 and a second binding domain targeting a different second epitope on HER2.

The protein consisting of SEQ ID NO: 32 is a bi-paratopic binding protein comprising two designed ankyrin repeat domains with binding specificity for HER2 targeting different epitopes on HER2. The recombinant binding protein consisting of SEQ ID NO: 21 comprises SEQ ID NO: 32.

The expression "exhibits improved pharmacokinetic properties", "improved pharmacokinetic properties", or "pharmacokinetic property improvement" in this invention has the meaning that a pharmacokinetic parameter of a recombinant binding protein is improved compared to the corresponding pharmacokinetic parameter of a protein it is compared with. Corresponding examples are shown in Examples 8, 9, 10, and 11 (see FIGS. 5A to 5C and FIGS. 6A and 6B). Preferably, an improved pharmacokinetic property is a reduced clearance, and/or an increased exposure, and/or an increased terminal half-life. More preferably, an improved pharmacokinetic property is an increased terminal half-life. In one embodiment, a recombinant binding protein of the present invention, comprising at least two, more preferably comprising two, designed ankyrin repeat domains with binding specificity for serum albumin exhibits an increased terminal half-life, and/or a reduced clearance, and/or an increased exposure of at least 5%, 10%, 15%, 20%, 25%, 30%, 35%, 40%, 45%, 50%, 60%, 70%, 80%, 90%, 100%, 150%, 200%, 250%, or 250% compared to a corresponding recombinant binding protein comprising only one designed ankyrin repeat domain with binding specificity for serum albumin. In one embodiment, a recombinant binding protein of the present invention, comprising at least two, more preferably comprising two, designed ankyrin repeat domains with binding specificity for serum albumin exhibits an increased terminal half-life, preferably an increased terminal half-life of at least 5%, 10%, 15%, 20%, 25%, 30%, 35%, 40%, 45%, 50%, 60%, 70%, 80%, 90%, 100%, 150%, 200%, 250%, or 250% compared to a corresponding recombinant binding protein comprising only one designed ankyrin repeat domain with binding specificity for serum albumin.

Preferably, clearance, and/or exposure, and/or terminal half-life are assessed in a mammal, more preferably mouse and/or cynomolgus monkey, more preferably cynomolgus monkey. Preferably, when measuring the clearance, and/or exposure, and/or terminal half-life in mouse, the evaluation is done considering the data up to 48 h post-injection. More preferably, the evaluation of terminal half-life in mouse is calculated from 24 h to 48 h. Preferably, when measuring the clearance, and/or exposure, and/or terminal half-life in cynomolgus monkey, the evaluation is done considering the data up to day 7 post-injection. More preferably, the evaluation of terminal half-life in cynomolgus monkey is calculated from day 1 to day 5. The person skilled further is able to identify effects such as target-mediated clearance and consider them when calculating the terminal half-life.

The term "terminal half-life" of a drug such as a recombinant binding protein of the invention refers to the time required to reach half the plasma concentration of the drug applied to a mammal after reaching pseudo-equilibrium (for example calculated from 24 hours to 48 hours in mouse or calculated from day 1 to day 5 in cynomolgus monkey). Terminal half-life is not defined as the time required to eliminate half the dose of the drug administered to the mammal. The term terminal half-life is well known to the person skilled in the art. Preferably, pharmacokinetic comparison is done at any dose, more preferably at equivalent dose (i.e. same mg/kg dose) or equimolar dose (i.e. same mol/kg dose), more preferably at equimolar dose (i.e. same mol/kg dose). It is understood by the person skilled in the art that equivalent and/or equimolar dosing in animals is subject to experimental dose variations of at least 20%, more preferably 30%, 40%, 50%, 60%, 70%, 80%, 90%, or 100%. Preferably, a dose used for pharmacokinetic measurement is selected from 0.001 to 1000 mg/kg, more preferably 0.01 to 100 mg/kg, more preferably 0.1 to 50 mg/kg, more preferably 0.5 to 10 mg/kg.

EXAMPLES

General materials and methods: All of the standard materials and reagents disclosed here are known to those skilled in the art, and are available commercially or can be prepared using well-known techniques. Cell lines were purchased from LGC/ATCC (France/USA). Cell culture media were from Invitrogen/Lubio (Switzerland). Unless stated otherwise, methods are performed according to described established protocols (e.g. Sambrook J., Fritsch E. F. and Maniatis T., Molecular Cloning: A Laboratory Manual, Cold Spring Harbor Laboratory 1989, New York), well-known to the practitioner in the art. Some methods used have previously been described in WO2012/069654 and WO2014/083208.

Designed ankyrin repeat domains: Methods to generate designed ankyrin repeat domains with binding specificity for serum albumin have been described in WO2012/069654. Methods to generate designed ankyrin repeat domains with binding specificity for HER2, and examples of such designed ankyrin repeat domains and methods to generate bi-paratopic binding proteins have been described WO2014/083208. Designed ankyrin repeat domains in general are described in detail in WO2002/020565.

Example 1: Recombinant DNA, Protein Expression and Protein Purification

DNA encoding designed ankyrin repeat domains or recombinant binding proteins was generated by genetic means well known to the person skilled in the art. Recombinant binding proteins selected from the group of amino acid sequences SEQ ID NOs: 21 to 33, optionally additionally having SEQ ID NO: 1 at the N terminus, or designed ankyrin repeat domains selected from the group of amino acid sequences SEQ ID NOs: 10 to 20, optionally additionally having SEQ ID NO: 1 at the N terminus, were expressed in the cytoplasm of *Escherichia coli* using standard techniques using for example the pQE expression system from Qiagen (Germany). In case the amino acids GS were at the N terminus, the Met residue additionally encoded by the expression vector was efficiently cleaved off in the cytoplasm of *E. coli* from the expressed polypeptide since the start Met is followed by a small Gly residue (i.e. the amino acid at position 1 of for example SEQ ID NO: 21). The cells were lysed by using a French press, and the proteins were purified to near homogeneity from the crude cell extract by using standard chromatographic techniques well known to the person in the art.

The following list defines the proteins as used in the present invention:
Protein #10-His: SEQ ID NO: 10 with a His-tag (SEQ ID NO: 1) fused to its N terminus
Protein #11-His: SEQ ID NO: 11 with a His-tag (SEQ ID NO: 1) fused to its N terminus
Protein #12-His: SEQ ID NO: 12 with a His-tag (SEQ ID NO: 1) fused to its N terminus
Protein #13-His: SEQ ID NO: 13 with a His-tag (SEQ ID NO: 1) fused to its N terminus
Protein #14-His: SEQ ID NO: 14 with a His-tag (SEQ ID NO: 1) fused to its N terminus
Protein #15-His: SEQ ID NO: 15 with a His-tag (SEQ ID NO: 1) fused to its N terminus
Protein #16-His: SEQ ID NO: 16 with a His-tag (SEQ ID NO: 1) fused to its N terminus
Protein #17-His: SEQ ID NO: 17 with a His-tag (SEQ ID NO: 1) fused to its N terminus
Protein #18-His: SEQ ID NO: 18 with a His-tag (SEQ ID NO: 1) fused to its N terminus
Protein #19-His: SEQ ID NO: 19 with a His-tag (SEQ ID NO: 1) fused to its N terminus
Protein #20-His: SEQ ID NO: 20 with a His-tag (SEQ ID NO: 1) fused to its N terminus
Protein #21: SEQ ID NO: 21
Protein #21-His: SEQ ID NO: 21 with a His-tag (SEQ ID NO: 1) fused to its N terminus
Protein #22: SEQ ID NO: 22
Protein #22-His: SEQ ID NO: 22 with a His-tag (SEQ ID NO: 1) fused to its N terminus
Protein #23: SEQ ID NO: 23
Protein #23-His: SEQ ID NO: 23 with a His-tag (SEQ ID NO: 1) fused to its N terminus
Protein #24: SEQ ID NO: 24
Protein #24-His: SEQ ID NO: 24 with a His-tag (SEQ ID NO: 1) fused to its N terminus
Protein #25: SEQ ID NO: 25
Protein #25-His: SEQ ID NO: 25 with a His-tag (SEQ ID NO: 1) fused to its N terminus
Protein #26: SEQ ID NO: 26
Protein #26-His: SEQ ID NO: 26 with a His-tag (SEQ ID NO: 1) fused to its N terminus Protein #27: SEQ ID NO: 27
Protein #27-His: SEQ ID NO: 27 with a His-tag (SEQ ID NO: 1) fused to its N terminus
Protein #28: SEQ ID NO: 28
Protein #28-His: SEQ ID NO: 28 with a His-tag (SEQ ID NO: 1) fused to its N terminus
Protein #29: SEQ ID NO: 29
Protein #29-His: SEQ ID NO: 29 with a His-tag (SEQ ID NO: 1) fused to its N terminus
Protein #30: SEQ ID NO: 30
Protein #30-His: SEQ ID NO: 30 with a His-tag (SEQ ID NO: 1) fused to its N terminus
Protein #31-His: SEQ ID NO: 31 (includes a His-tag at its N terminus)
Protein #32: SEQ ID NO: 32
Protein #32-His: SEQ ID NO: 32 with a His-tag (SEQ ID NO: 1) fused to its N terminus
Protein #33: SEQ ID NO: 33
Protein #33-His: SEQ ID NO: 33 with a His-tag (SEQ ID NO: 1) fused to its N terminus

Example 2. Generation of a Stability-Improved Designed Ankyrin Repeat Domain with Binding Specificity for Serum Albumin (SEQ ID NO: 14)

In contrast to general designed ankyrin repeat knowledge we found that Protein #12-His, Protein #13-His, and Protein #15-His (WO2012/069654; see Example 1) degrade upon prolonged incubation in PBS at 10 mg/kg at 40° C., and are thus not ideal for use as components in drug candidates. Analysis of the amino acid sequence of SEQ ID NO: 13 reveals a high number of potential degradation sites. Degradation may for example occur in the vicinity of any one of the 5 asparagines (including asparagine-glycine dipeptides), 13 aspartates, or 10 glycines of SEQ ID NO: 13, amongst additional potential degradation sites. SEQ ID NO: 13 further comprises a number of potential oxidation sites. A high number of mutants and combination mutants has thus to be analyzed to isolate a variant that exhibits improved storage stability properties. Surprisingly, we could generate a functional variant that exhibits a major effect on storage stability by mutating position 80 only of SEQ ID NO: 13. When mutating aspartate at position 80 of SEQ ID NO: 13 to glutamate, a functional designed ankyrin repeat domain with binding specificity for serum albumin was generated, corresponding to SEQ ID NO: 14, which does show a marked improvement in storage stability (Example 3; FIGS. 2A and 2B). Protein #14-His, like Protein #13-His, showed low nanomolar affinity (dissociation constant (Kd) below 100 nM) to human, mouse and cynomolgus monkey serum albumin at pH 7.4 in PBS (ProteOn surface plasmon resonance measurement according to manufacturer (BioRad)). Surprisingly, Protein #14-His, additionally exhibited an improved midpoint of thermal denaturation compared to Protein #13-His, as determined by thermal unfolding using well-known techniques (Niesen, F. H., Berglund, H., Vedadi, M., Nature Protocols 2, 2212-2221, 2007; Protein #13-His: Tm=86° C.; Protein #14-His, Tm=89.5° C.; pH 6.0).

Example 3. Improvement of Protein Storage Stability when Using SEQ ID NO: 14

Protein #13-His, Protein #14-His and Protein #15-His were prepared as described in Example 1, and samples were concentrated to 10 mg/ml in PBS. Protein #14-His and Protein #15-His where then stored for 1 month at −80° C. or at 40° C. in glass vials, followed by analysis on SDS 15% PAGE. While Protein #14-His and Protein #15-His showed equivalent stability upon storage at −80° C., Protein #14-His showed significantly reduced amounts of degradation products by >50% reduction compared to Protein #15-His on SDS 15% PAGE after 1 month storage at 40° C. Similarly, when stored at 4° C., 25° C., 40° C. and 60° C. for one week at 10 mg/ml in PBS, Protein #14-His showed significantly reduced amounts of degradation products compared to Protein #13-His. In particular, Protein #14-His showed >50% reduction of degradation products compared to Protein #13-His on SDS 15% PAGE both when stored at 40° C. or 60° C., respectively (FIGS. 2A and 2B). These findings illustrate that Protein #14-His has improved storage stability compared to Proteins #13-His and Protein #15-His. Similarly, when comparing the storage stability of Protein #12-His, Protein #13-His, Protein #14-His, and Protein #15-His (see Example 1), by incubating the proteins at 10 mg/ml in PBS in glass vials for 1 month at 40° C., Protein #12-His, Protein #13-His, and Protein #14-His exhibit >30% reduction of degradation products compared to Protein #15-His.

A storage stability improvement is also observed, when testing the storage stability of Protein #21 and Protein #22 (recombinant binding proteins consisting of the amino acid sequences corresponding to SEQ ID NOs: 21 and 22, respectively). Protein #21 and Protein #22 are prepared as described in Example 1, samples are concentrated to 10 mg/ml in PBS and stored for 1 month at −80° C. in or at 40° C. in glass vials, followed by analysis on standard size-exclusion chromatography. While Protein #21 and Protein #22 show equivalent elution profiles upon storage at −80° C., Protein #21 shows significantly more monomeric species compared to Protein #22 upon storage at 40° C. This indicates that having SEQ ID NO: 21 present in the recombinant binding protein is more favorable regarding storage stability than having SEQ ID NO: 22 present. Similarly, Protein #21 exhibits lower amounts of degradation products than Protein #22 when analyzed by SDS-PAGE after 1 month storage at 40° C. in glass vials in PBS at 10 mg/ml, confirming the higher storage stability of a recombinant binding protein comprising SEQ ID NO: 21 in comparison to the recombinant binding protein comprising SEQ ID NO: 22. In turn, this indicates that having designed ankyrin repeat domains with binding specificity for serum albumin consisting of SEQ ID NO: 14 present in the recombinant binding protein is more favorable regarding storage stability than having designed ankyrin repeat domains with binding specificity for serum albumin consisting of SEQ ID NO: 13 present.

Example 4: Generation of a Drug Candidate

Examples of designed ankyrin repeat domains with binding specificity for HER2 have been disclosed earlier (WO2014/083208; WO2014/060365; Steiner, D., Forrer, P. and Plückthun, A., J. Mol. Biol. 382, 1211-1227, 2008; Zahnd, C., Pecorari, F., Straumann, N., Wyler, E. and Plückthun, A., J. Biol. Chem. 281(46), 35167-35175, 2006). In WO2014/083208 and WO2014/060365, designed ankyrin repeat domains with binding specificity for HER2 binding to different domains were combined, resulting in bi-paratopic binding proteins that show enhanced inhibition of tumor cell growth.

The recombinant binding protein consisting of SEQ ID NO: 21 is a drug candidate comprising two designed ankyrin repeat domains with binding specificity for HER2 (SEQ ID NOs: 16 and 17, respectively) as well as two flanking designed ankyrin repeat domains with binding specificity for serum albumin (each SEQ ID NO: 14), linked by polypeptide linkers (each SEQ ID NO: 9) (see FIGS. 1A to 1E). This recombinant binding protein has been identified by a complex procedure including protein engineering and optimization steps amongst others. In a first step, hundreds of combinations of designed ankyrin repeat domains with binding specificity for HER2 were generated as bi-paratopic binding proteins by cloning, expression and purification (see Example 1). The bi-paratopic binding proteins were then screened for affinity for HER2 as well as cellular potency and cell proliferation inhibition as described in WO2014/083208 and as described below. Representative results of bi-paratopic binding proteins resulting from this effort are given in Examples 5 and 6. Importantly, the molecule needs to be bi-paratopic, as having only one designed ankyrin repeat domain with binding specificity for HER2 leads molecules with no cellular inhibition potency. Recombinant binding proteins where further engineered. This step included (amongst others) the pharmacokinetic engineering by adding designed ankyrin repeat domains with binding specificity for serum albumin in various formats (i.e. adding different numbers of designed ankyrin repeat domains with binding specificity for serum albumin at different positions in the molecule) to the bi-paratopic binding proteins, and by testing various polypeptide linkers. These proteins were tested for in vivo efficacy (representative Example 7), pharmacokinetics in mouse (representative Example 8), and pharmacokinetics in cynomolgus monkey (representative Example 9) as well as for cellular potency. The optimization of the polypeptide linker included a step of testing the effect of the linker on the pharmacokinetic profile (representative Example 10). The optimization of the pharmacokinetic engineering effort was assessed by pharmacokinetic measurements (representative Example 11) and potency measurements (representative Example 12). Furthermore, the various drug candidates were tested for their recombinant expression levels in *E. coli* (Example 13). The recombinant binding protein consisting of SEQ ID NO: 21 is a protein resulting from this effort. It is a drug candidate for use in man.

Protein #31, the recombinant binding protein consisting of SEQ ID NO: 31, corresponds to the protein consisting of Protein #21 and the amino acids of SEQ ID NO: 1 at the N terminus.

Example 5: High-Affinity Binding of HER2 by the Recombinant Binding Protein Comprising SEQ ID NO: 21

Protein #21-His was expressed and purified as described in Example 1. Its affinity to HER2 was assessed by surface plasmon resonance as described in WO2014/083208. A dissociation constant of 27 pM was determined by global fitting of the resonance unit values obtained for different concentrations, a method well known to the practitioner in the art. In comparison, Protein #23-His (see Example 1), comprising another combination of designed ankyrin repeat domains with binding specificity for HER2 exhibited a dissociation constant of 64 pM. Likewise, the combination of the designed ankyrin repeat domains corresponding to SEQ ID NO: 16 and 17 exhibited better dissociation constant than the majority of the combinations generated based on the designed ankyrin repeat domains with binding specificity for HER2 known from WO2014/083208.

Surface plasmon resonance measurements further showed that the recombinant binding protein consisting of SEQ ID NO: 21 does not interact with extracellular domains of HER3 or EGFR.

Surface plasmon resonance measurements further showed that the designed ankyrin repeat domains consisting of SEQ ID NOs: 16 or 17 (each additionally comprising SEQ ID NO: 1 at the N terminus) exhibit a dissociation constant of 9 pM and 152 pM, respectively, for HER2 binding.

Surface plasmon resonance experiments further showed that Protein #21 can bind human HER2 and human serum albumin simultaneously.

Surface plasmon resonance experiments further showed that Protein #21 at 100 nM binds human serum albumin with a dissociation constant (Kd) of 21 nM.

Example 6: High Cellular Potency and Induction of Apoptosis of the Recombinant Binding Protein Comprising SEQ ID NO: 21

Protein #21-His and Protein #23-His, were expressed and purified as described in Example 1. Effects of the recombinant binding proteins on BT474 cell proliferation were determined by measuring DNA synthesis using BrdU-labeling (BrdU, Cell Proliferation ELISA, Roche). Briefly, 10000 BT474 cells were seeded per well in a 96 well plate in 100 ul complete medium and incubated for 24 hours. Recombinant binding proteins or controls were added for an additional 72 hours. BrdU for cell labeling was added for the last 24 hours. Labeled (proliferating) cells were detected according to the manufactures protocol. The data were analyzed using the GraphPad prism software, plotting log [c] on the x-axis against OD450-602 nm on the y-axis. Data were fitted using a non-linear regression fit (log(antagonist) vs. response—Variable slope (four parameters)) deriving $IC_{50}$ values. Results are shown in FIG. 3. Protein #21-His inhibits the proliferation of BT474 cells with an apparent $IC_{50}$ value of 1.5 nM. A 60% higher (i.e. worse) $IC_{50}$ of 2.4 nM is observed for Protein #23-His, indicating that having SEQ ID NOs: 16 and 17 in a recombinant binding protein is more favorable than having SEQ ID NOs: 18 and 17. Likewise, the combination of the designed ankyrin repeat domains corresponding to SEQ ID NO: 16 and 17 inhibited BT474 cells with a lower apparent $IC_{50}$ value than the ones observed for the majority of the combinations generated based on the designed ankyrin repeat domains with binding specificity for HER2 known from WO2014/083208.

The recombinant binding protein consisting of SEQ ID NO: 21 (Protein #21) further exhibited strong proliferation inhibition on a variety of cancer cell-lines including the cell-lines SKBR-3, SKOV-3, NCI-N87, ZR-75-30, HCC1419, or MDA-MB175.

Induction of apoptosis by Protein #21 was determined by measuring Caspase3/7 activation using the Caspase 3/7-Glo systems (Promega, Switzerland). Briefly, 10000 BT474 cells were seeded per well in a 96 well plate in 100 µl complete medium and incubated for 24 hours. Protein #21 and benchmarks were added for an additional 24 hours. Caspase Glo reagent was added according to the manufactures protocol for 1 hour. Caspase 3/7 activation was monitored by measuring luciferase activity. Alternatively induction of apoptosis was determined using the Cell Death Detection ELISAPLUS system (Roche, Switzerland). The assay was performed according to the manufactures protocol. Cell number and incubations times were similar to the Caspase Glo readout. Data were analyzed using the GraphPad prism software, plotting concentration on the x-axis against OD405/490 nm or relative light units (RLU; measured on a Tecan M-1000 reader) on the y-axis. Data were fitted using a non-linear regression fit (log(agonist) vs. response—Variable slope (four parameters)). Results are shown in FIG. 7. For Protein #21, an EC50 of 2.4 nM was observed. Apoptosis exhibits likewise high potency in inducing apoptosis for the cell lines SKBR-3, SKOV-3, NCI-N87, ZR-75-30, HCC1419, or MDA-MB175. In contrast, the antibodies Trastuzumab, Pertuzumab, or the mixture of Trastuzumab and Pertuzumab did not induce apoptosis in BT474 cells (FIG. 7).

Importantly, these assays show, that Protein #21, wherein SEQ ID NO: 32 is flanked by SEQ ID NO: 14, exhibits high cellular potency, similar to when using SEQ ID NO: 32 alone.

Example 7: High Efficacy of the Recombinant Binding Protein Comprising SEQ ID NO: 21 in Mouse Tumor Xenograft Models Protein #21-His, Protein #23-His, Protein #24-His, Protein #25-His were expressed and purified as described in Example 1. In one study, Protein #21-His was compared to Trastuzumab and PBS. The results are shown in FIG. 4A. BT474 breast cancer tumor xenograft mouse models were essentially performed as follows using procedures well known to the person skilled in the art: BT474 human breast carcinoma cells were cultured, resuspended, and $2*10^7$ cells in 200 µl RPMI 1640 medium containing 50:50 matrigel (BD Biosciences) per mouse were injected into the right flank of female Balb/c nude mice. At tumor volumes of about 200-300 mm$^3$, mice were randomized into groups of 8 animals, and tumor treatment was started by i.v. administration of PBS, Trastuzumab (10 mg/kg), Trastuzumab (10 mg/kg) and Pertuzumab (10 mg/kg), or Protein #21-His (35 mg/kg) for 7 doses with a 3 day interval (Q3Dx7). Tumor volumes were measured for 32 days. Protein #21-His is more efficacious in inhibiting tumor growth than Trastuzumab.

In a similar study using BT474 cells (identical setup and procedure; all 35 mg/kg doses), Protein #21-His was compared to Protein #23-His, Protein #24-His, and Protein #25-His. The results at day 18 after treatment are shown in FIG. 4B. Importantly, Protein #21-His is more efficacious in suppressing tumors than Protein #23-His, Protein #24-His, or Protein #25-His.

Further, Protein #21 was expressed and purified as described in Example 1. PBS, Protein #21 (60 mg/kg), Trastuzumab (10 mg/kg), Pertuzumab (10 mg/kg) as well as the combination of Trastuzumab and Pertuzumab (10 mg/kg each) were used in a patient derived gastric cancer tumor xenograft mouse model, well known to the person skilled in the art. All groups were dosed every three days for 6 times. Briefly, tumor fragments were obtained from xenografts in serial passage in nude mice. After removal from donor mice, tumors were cut into fragments (4-5 mm diameter) for subcutaneous implantation. Mice were randomized into groups when tumors reached a volume of approximately 100-120 mm$^3$. The day of randomization and treatment initiation is designated as day 0 in each experiment. Tumor growth was monitored by two-dimensional measurement with a caliper on the day of randomization and then twice weekly. Relative volumes of individual tumors (individual RTVs) for Day x were calculated by dividing the individual tumor volume on Day x (Tx) by the individual volume of the same tumor on Day 0 (T0) multiplied by 100%. Tumor inhibition for a particular day (T/C in %) was calculated from the ratio of the median RTV values of test versus control groups multiplied by 100%. FIG. 4C shows the efficacy of Protein #21 in the gastric cancer PDX model GXA3039 compared to Trastuzumab and a combination of Trastuzumab and Pertuzumab. Protein #21 exhibits strong inhibition of tumor growth, similar to the combination of Trastuzumab and Pertuzumab, whereas Trastuzumab alone is less efficacious. FIG. 4D shows a second experiment in the same model comparing Protein #21 with Trastuzumab, Pertuzumab, and a combination of Trastuzumab and Pertuzumab. Protein #21 exhibits strong inhibition of tumor growth, similar to the combination of Trastuzumab and Pertuzumab. Trastuzumab alone and Pertuzumab alone are significantly less efficacious. This indicates that the tumor model might have acquired Trastuzumab resistance over time. This in turn suggests that Protein #21 is efficacious even in Trastuzumab-resistant cancer.

In a similar experiment, Protein #21 was further tested in the gastric cancer PDX mouse model GXA281, well known to the person skilled in the art, in comparison to the standard of care Lapatinib (FIG. 4E). Briefly, tumor implantation and tumor growth monitoring was done as described above. Lapatinib was dosed at 100 mg/kg/day for 21 days daily i.v. and Protein #21 at 40 mg/kg every three days for 6 times i.v.

These experiments of this example illustrate the utility of proteins comprising SEQ ID NO: 21 for use as a medicament in the treatment of disease.

Example 8: Favorable Pharmacokinetic Properties of the Recombinant Binding Protein Comprising SEQ ID NO: 21 in Mouse The measurements shown in this example are the result of a half-life engineering effort as described in Example 11. Protein #21-His and Protein #23-His were expressed and purified as described in Example 1. The pharmacokinetic properties of the His-tagged proteins were assessed in mouse as described elsewhere (Zahnd, C., Kawe, M., Stumpp, M. T., de Pasquale, C., Tamaskovic, R., Nagy-Davidescu, G., Dreier, B., Schibli, R., Binz, H. K., Waibel, R., Plückthun, A., Cancer Res. 70, 1595-1605, 2010). The results are shown in FIGS. 5A to 5C. Protein #21-His exhibits a terminal half-life of 30.4 hours with 19.5% ID remaining after 48 hours. In comparison Protein #23-His exhibits a terminal half-life of 24.7 hours with 6.5% ID remaining after 48 hours. Having SEQ ID NO: 16 present in the recombinant binding protein thus appears to be more favorable than having SEQ ID NO: 18 present.

Example 9: Favorable Pharmacokinetic Properties of the Recombinant Binding Protein Comprising SEQ ID NO: 21 in Cynomolgus Monkey The measurements shown in this example are the result of a half-life engineering effort as described in Example 11. Protein #21-His, Protein #23-His, and Protein #24-His were expressed and purified as described in Example 1. The pharmacokinetic properties of the proteins were assessed in cynomolgus monkey. Proteins were administered via intravenous infusion for 30 min at a target dose level of between 1 mg/kg to cynomolgus monkeys. Blood samples were collected pre-dose and again at selected time points, for example 5 min, 10 min, 0.5 hours, 1 hour, 2 hours, 4 hours, 8 hours, 12 hours, 24 hours, 48 hours, 72 hours, 96 hours, 120 hours, 144 hours, 168 hours, 192 hours, 216 hours, and 240 hours post-end of infusion (i.e. post-injection). The blood samples were allowed to stand at room temperature and were centrifuged to generate serum, followed by storage at −80° C. pending analyses. Pharmacokinetic parameters were determined using procedures well known to the person skilled in the art. Serum concentrations of proteins were determined by sandwich ELISA using a rabbit monoclonal anti-designed ankyrin repeat domain antibody as capture reagent and murine monoclonal anti-designed ankyrin repeat domain antibody as detection reagent, and using a standard curve. Pharmacokinetic parameters were determined using standard software such as Phoenix WinNonLin (Certara, Princeton, USA) or GraphPadPrism (GraphPad Software, La Jolla, USA) and standard analyses such as non-compartmental analyses. The results for Protein #21-His and Protein #23-His are shown in FIGS. 6A and 6B. Protein #21-His exhibits a terminal half-life of 47 hours, while Protein #23-His exhibited a terminal half-life of 35 hours, and Protein #24-His exhibited a terminal half-life of 45 hours. The proteins also exhibit significant target-mediated clearance once the concentration falls below 100 nM. Target mediated clearance is well-known to the person skilled in the art and is known from e.g. antibodies targeting HER2.

Similarly, Protein #21-His was expressed and purified as described in Example 1. The pharmacokinetic properties of the proteins were assessed in cynomolgus monkey as described above at 1 mg/kg, 5 mg/kg and 10 mg/kg. Pharmacokinetic parameters were evaluated as described above and the results are shown in FIGS. 6A and 6B. A dose dependent increase of the terminal half-life from 47 hours at 1 mg/kg to 100 hours at 5 mg/kg to more than 100 hours at 10 mg/kg. was observed. Target mediated clearance is observed once the concentration falls below 100 nM.

Similar results are observed when testing Protein #21 (expressed and purified as described in Example 1). The pharmacokinetic properties of the proteins are assessed in cynomolgus monkey as described above at 1 mg/kg, 10 mg/kg and 100 mg/kg. Pharmacokinetic parameters are evaluated as described above. A dose dependent increase of the terminal half-life is observed. For Protein #21, a terminal half-life of 109.5 hours or 130.6 hours was observed at a dose of 100 mg/kg in cynomolgus monkey.

Example 10: Improving Drug Properties by the Choice of Polypeptide Linkers

Polypeptide linkers that link protein domains are well-known to the person skilled in the art. Gly-Ser-rich linkers are well-known from single-chain Fv antibody fragments, where they have proven to be most appropriate to link the two Fv polypeptide chains. Surprisingly, we find that Pro-Thr-rich linkers have a positive impact on the pharmacokinetic properties of a recombinant binding protein comprising two designed ankyrin repeat domains with binding specificity for HER2 and two designed ankyrin repeat domains with binding specificity for serum albumin in comparison to a Gly-Ser-rich linker. Protein #26-His and Protein #27-His, were expressed and purified as described in Example 1. Pharmacokinetic analyses in mouse were performed as described in Example 8. Protein #27-His had 7% of the injected dose remaining 48 hours after intravenous injection, whereas Protein #26-His only had 5.3% injected dose remaining. Similarly, Protein #27-His exhibited a longer terminal half-life than Protein #26-His.

Example 11: Engineering Pharmacokinetic Properties

Many options are known in the art for pharmacokinetic engineering including PEGylation, polypeptide extension, Fc-fusion, serum albumin-fusion, and binding to serum albumin, amongst others (Kontermann, R (Ed.) "Therapeutic proteins: strategies to modulate their plasma half-lives", Wiley-VCH Verlag GmbH, 2012, ISBN 978-3-527-32849-9). Starting from e.g. the combination of designed ankyrin repeat domains with binding specificity for HER2 comprising SEQ ID NOs: 16 and 17, there are hundreds of potential drug candidate variants (choice of pharmacokinetic modification engineering, choice of polypeptide linker (e.g. SEQ ID NOs: 2 to 9 amongst many others), amongst other aspects). We found that using two designed ankyrin repeat domains with binding specificity for serum albumin consisting of SEQ ID NO: 14 (see Examples 2 and 3), and by using Pro-Thr-rich polypeptide linkers (SEQ ID NO: 9), resulting in SEQ ID NO: 21, beneficial pharmacokinetic properties are achieved, and it has clear advantages over the other formats tested. Results of the effect of the choice of the polypeptide linker are shown e.g. in Example 10. The comparison of the mouse pharmacokinetic profiles of Protein #29-His and Protein #30-His, surprisingly reveals a benefit of having two designed ankyrin repeat domains with binding specificity for serum albumin as compared to having only one designed ankyrin repeat protein with binding specificity for serum albumin (See FIGS. 5A to 5C), as literature on the albumin binding domain indicates that having two albumin binding domains present in a molecule does not result in any benefit on pharmacokinetic properties as compared to having only one albumin binding domain present (Hopp et al., loc. cit.). Similarly, when comparing Protein #21 (recombinant binding proteins consisting of SEQ ID NOs: 21) with a Protein #21 variant, wherein the C-terminal designed ankyrin repeat domain with binding specificity for serum albumin is missing (amino acids 1 to 422 of SEQ ID NO: 21, resulting in Protein #33), Protein #21 exhibits markedly improved pharmacokinetic properties, in particular a longer terminal half-life. Comparing the cynomolgus monkey pharmacokinetic profile of Protein #21 with PEGylated Protein #28 (which comprises the same designed ankyrin repeat domains with binding specificity for HER2 (SEQ ID NOs: 16 and 17), but Protein #28 comprises a 40 kDa PEG moiety instead of two designed ankyrin repeat domains with binding specificity for serum albumin) at 5 mg/kg doses, indicates that the protein comprising two designed ankyrin repeat domains with binding specificity for serum albumin exhibits markedly improved pharmacokinetic properties. As described in Example 9, the comparison of the pharmacokinetic profiles of Protein #21-His and Protein #24-His, reveals that it is more favorable having the two designed ankyrin repeat domains with binding specificity for serum albumin flanking SEQ ID NOs: 16 and 17 rather than having them both N-terminally (See FIGS. 6A and 6B).

For the studies in this example Protein #21-His, Protein #24-His, Protein #28-His, Protein #29-His, and Protein #30-His were prepared according to Example 1. Protein #28-His was additionally PEGylated using a 40 kDa PEG moiety (NOF Sunbright GL2-400MA) by maleimid coupling of the PEG-moiety onto the free C-terminal cysteine of Protein #28-His, followed by purification to homogeneity using standard purification methods, procedures well known to the person skilled in the art. Pharmacokinetic analyses in mouse or cynomolgus monkey were performed as described in Examples 8 and 9.

Example 12: A Recombinant Binding Protein Comprising SEQ ID NO: 21 Exhibits Better in Vivo Potency as Compared to a Recombinant Binding Protein Comprising SEQ ID NO: 24

Protein #21-His and Protein #24-His, were expressed and purified as described in Example 1. Mouse xenograft experiments were performed as described in Example 7. Results are shown in FIG. 4B. After 32 days of treatment, Protein #21-His exhibits significantly better tumor suppression than Protein #24-His. This indicates that having the designed ankyrin repeat domains with binding specificity for serum albumin flanking the designed ankyrin repeat domains with binding specificity for HER2 (as found in SEQ ID NO: #21) is more favorable than having the designed ankyrin repeat domains with binding specificity for serum albumin both N-terminal of the designed ankyrin repeat domains with binding specificity for HER2 (as found in SEQ ID NO: 24).

Example 13: High Recombinant Expression Yield in E. coli

The sequences encoding Protein #21, Protein #23, and Protein #25 were cloned in a standard T7 promotor vector and the proteins were expressed in E. coli HMS 174 (DE3). For Protein #21, titers of 4.4 g/l were achieved, whereas Protein #23 showed a titer of 1.9 g/l, and Protein #25 showed a titer of 2.1 g/l, indicating best expression of Protein #21. Surprisingly, the arrangement of designed ankyrin repeat domains used in Protein #21 leads thus to higher recombinant expression than for example observed for another arrangement used in Protein #25, despite the same components (designed ankyrin repeat domains and polypeptide linkers) being used. Interestingly, the combination of the designed ankyrin repeat domains corresponding to SEQ ID NO: 16 and 17 exhibited better recombinant protein expression than the majority of the combinations generated based on the designed ankyrin repeat domains with binding specificity for HER2 known from WO2014/083208.

Example 14: Simultaneous Binding of Two Serum Albumin Molecules by Protein #21

Protein #21 was expressed and purified as described in Example 1. Size exclusion chromatography coupled to static light scattering (Superdex 200 10/300GL (GE Healthcare), Agilent 1200 (Life Technologies), Wyatt Optilab Trex (RI) and MiniDawnTreos (MALS)) was performed using 30 µM Protein #21, 60 µM human serum albumin (CSL Behring 20% solution was used to purify the monomeric fraction of human serum albumin by size exclusion chromatography on a Superdex 200 26/60 column (GE Healthcare)), or a 1:2 mixture of the two, in PBS.

Protein #21 eluted as a monomeric peak and a molecular weight of 65.2 kDa was determined by MALS, which is within 1.2 kDa of its theoretical molecular weight (66437 Da). Serum albumin eluted as monomeric peak of 55.1 kDa (theoretical molecular weight 58917 Da). The 1:2 mixture (molar ratio) of the two molecules lead to a main peak with an average molecular weight of 169.8 kDa (range: 186.2 kDa to 136.6 kDa), comprising molecular weight species corresponding to a 1:2 complex (theoretical molecular weight: 191.8 kDa) as well as a 1:1 complex (132.8 kDa). Additionally, a small peak of free serum albumin was detected corresponding to 6.5% of the serum albumin used in the experiment. No peak comprising a molecular mass corresponding to the free Protein #21 was detected. These results indicate that Protein #21 can bind two serum albumin molecules simultaneously.

Example 15: High Thermal Stability of Protein #21

Protein #21 was expressed and purified as described in Example 1. Thermal stability was evaluated using circular dichroism using a Jasco J-815 CD spectrometer in a nitrogen atmosphere (3 L/min). Protein #21 at 0.4 µM in PBS in 117.100F-QS cuvettes (Hellma, d=1 cm) with in-solution temperature control sensors were measured, heating from 20° C. to 95° C. (below 45° C.: +3° C./min; above 45° C.: +1° C./min recording the signal at 222 nm, a 1 min delay at 95° C. and a subsequent cooling phase (inverted program compared to heating phase). The CD signal was normalized to mean residual ellipticity (MRE) with the unit deg cm2 dmol-1. Additionally, the far-UV CD spectrum was recorded.

Protein #21 exhibits a CD spectrum typical for alpha-helical proteins with characteristic minima at 208 nm and 222 nm. Protein #21 exhibits high thermal stability after a stable baseline (no change in slope), loss of signal at 222 nm is detected above 78° C.

Example 16: Impact of Protein #21 on the Phospho-Proteome

Protein #21 was expressed and purified as described in Example 1. BT474 or NCI-N87 cells were treated for 18 hours with either Protein #21 (100 nM), Trastuzumab (100 nM), Pertuzumab (100 nM), the mixture of Trastuzumab (100 nM) and Pertuzumab (100 nM), or PBS. Cells were then subjected to a phospho-proteome mass-spectrometry analysis as described by Britton, D., et al. (Britton, D., Zen, Y., Quaglia, A., Selzer, S., Mitra, V I., Lössner, C., Jung, S., Böhm, G., Schmid, P., Prefot, P., Hoehle, C., Koncarevic, S., Gee, J., Nicholson, R., Ward, M., Castellano, L., Stebbing, J., Zucht, H. D., Sarker, D., Heaton, N., and Pike, I., 2014. PLOS One 9 (3), e90948). The analysis reveals that cell treatment with Protein #21 differentially regulates multiple phosphorylated peptides compared to Trastuzumab, Pertuzumab and the combination of both. The results are shown in Table 1. Importantly, Protein #21 exhibits some marked differences to Trastuzumab, Pertuzumab, and the mixture of Trastuzumab and Pertuzumab, in that it inhibits stronger the phosphorylation HER2 at the sites 1073/1078/1083, 1139/1151, 1172/1174, 1174, and 1240. At other phosphorylation sites, phosphorylation is increased (772). Downstream of HER2, specific members of the mTOR signaling cascade were found to be differentially regulated upon treatment with Protein #21; e.g. a phosphopeptide for S6Kinase (S441/T444/5447) was downregulated 0.63 fold to PBS compared to other groups where downregulation was in the range of only 0.88 fold. Moreover phosphorylated peptides that map to MAPK1 and MAPK3 were considerably downregulated.

Analysis of the same samples by an phospho-site specific ELISA for AKT-S473 (BioConcept: PathScan® Phospho-Akt1 (Ser473) Sandwich ELISA Kit #7160) showed down-regulation by Protein #21 to 0.16 fold to PBS compared to other groups where downregulation was in the range of only 0.3 to 0.7 fold. The results of the ELISA are shown in Table 2.

These results indicate that Protein #21 is differentially regulating HER2 downstream signaling, compared to Trastuzumab, Pertuzumab and the combination of both. Largest differences were seen in the AKT-mTOR pathway, the critical pathway for cell survival, which in turn explains why Protein #21 is inducing apoptosis. The phosphoinositide 3-kinase (PI3K/Akt) pathway is considered to be one of the critical pathways that is maintaining cell survival by blocking apoptosis. Pathologic activation thereof, e.g., by HER2/HER3-heterodimerization, may thus lead to malignant proliferation.

In this experiment, it was further observed that exposure of BT474 and NCI-N87 cells to Protein #21 increased the cellular levels of Foxo3a protein by 1.88 and 2.8-fold, respectively, when compared to an exposure to PBS only. The corresponding increase of Foxo3a protein levels in BT474 and NCI-N87 cells by exposure to Trastuzumab was 1.14 and 1.32-fold, respectively; and by exposure to Pertuzumab 1.21 and 1.25-fold, respectively; and by exposure to Trastuzumab and Pertuzumab 1.28 and 1.19-fold, respectively. Thus, Protein #21 leads to a much higher increase of cellular Foxo3a protein levels compared to Trastuzumab or Pertuzumab or the combination of both. It is known to the practitioner in the art, that Akt1 phosphorylates Foxo3a, resulting in the degradation of Foxo3a and promotion of cell survival. Inhibition of Akt phosphorylation leads to stabilization of Foxo3a and thus increase in Foxo3a levels. At increased levels Foxo3a can translocate to the nucleus and induce apoptosis.

TABLE 1

Effect of different proteins on the phospho-proteome of BT474 cell proteins (HER2, AKT, mTOR, RPS6KB1/S6 Kinase, RAF) evaluated by mass spectrometry (fold change to PBS).

| Phosphorylation site | Protein #21 | Trastuzumab | Pertuzumab | Trastuzumab/Pertuzumab |
| --- | --- | --- | --- | --- |
| HER2 Y1139/S1151 | 0.88 | 1.3 | 0.92 | 1.71 |
| HER2 T1172/S1174 | 0.44 | 0.87 | 1.06 | 0.73 |
| HER2 S1174 | 0.59 | 0.88 | 1.1 | 0.94 |
| HER2 S1073/S1078/S1083 | 0.35 | 0.68 | 0.81 | 0.71 |
| HER2 T772 | 10.27 | 5.08 | 3.63 | 4.12 |
| HER2 T1240 | 0.09 | 1.08 | 0.92 | 1.49 |
| AKT S129 | 0.93 | 1.04 | 1.16 | 1.09 |
| AKT S124 | 0.99 | 0.9 | 1.04 | 1.14 |
| mTOR S2448/S2454 | 0.79 | 0.85 | 1.09 | 1.39 |
| RPS6KB1/S6Kinase T444/S447 | 0.92 | 0.97 | 1.04 | 0.94 |
| RPS6KB1/S6Kinase S441/T444/S447 | 0.63 | 0.88 | 1.02 | 0.85 |
| RAF S642 | 0.81 | 1.07 | 1.2 | 1.1 |
| RAF T631/T638/T640/T641/S642 | 0.48 | 0.77 | 1.01 | 0.62 |

TABLE 2

Effect of different proteins on the phosphorylation state of different of BT474 cell proteins (AKT, HER2, HER3, HER1/EGFR) evaluated by ELISA (fold change to PBS).

| Phosphorylation site | Protein #21 | Trastuzumab | Pertuzumab | Trastuzumab/ Pertuzumab |
|---|---|---|---|---|
| AKT S473 | 0.16 | 0.31 | 0.73 | 0.27 |
| HER2 Pan-Phospho-Tyrosine | 0.04 | 0.02 | 1.12 | 0.03 |
| HER3 Pan-Phospho-Tyrosine | 0.45 | 0.52 | 0.78 | 0.31 |
| HER1/EGFR Pan-Phospho-Tyrosine | 0.40 | 0.53 | 0.68 | 0.53 |

Example 17: Co-Medication Using Recombinant Binding Proteins Comprising SEQ ID NO: 21 for Therapy Improvement Protein #21 and Protein #21-His were expressed and purified as described in Example 1. Standard BrdU cell proliferation assays were performed, well-known to the person skilled in the art. Briefly, effects on cell proliferation of Protein #21-His, other compounds, or Protein #21-His in combination with other compounds, were determined by measuring DNA synthesis using BrdU-labeling (BrdU, Cell Proliferation ELISA, Roche). Briefly, 10000 cells were seeded per well in a 96 well plate in 100 μl complete medium and incubated for 24 hours. Protein #21-His and/or compounds were added for an additional 72 hours. BrdU for cell labeling was added for the last 24 hours. Labeled (proliferating) cells were detected according to the manufactures protocol. The data were analyzed using the GraphPad prism software (log [c] vs. OD450-602 nm plot). Data were fitted using a non-linear regression fit (log(antagonist) vs. response-variable slope (four parameters)). Combination of Protein #21-His with Eribulin, a microtubule inhibitor: Protein #21-His, Eribulin, or a combination of Protein #21-His and Eribulin was tested for its ability to inhibit proliferation of BT474 and MDA-MB175 cells. Eribulin was titrated starting at 1,000 nM on top of a suboptimal concentration of Protein #21-His (2 nM in BT474 and 4 nM in MDA-MB175). A combination of both molecules was superior to Eribulin by itself in both cell lines. Eribulin was not active on BT474 cells as a single agent but showed potent inhibition in combination with Protein #21-His. Eribulin showed very low potency on its own on MDA-MB175 cells but this was improved in combination with Protein #21-His. $IC_{50}$ values are given in Table 3. These data show that Protein #21-His can be combined with Eribulin and potentiates its activity.

Combination of Protein #21-His and GDC-0941, a p13K inhibitor: Protein #21-His, GDC-0941, or a combination of Protein #21-His and GDC-0941 were tested for their ability to inhibit proliferation of BT474 and MDA-MB175 cells. GDC-0941 was titrated starting at 20,000 nM on top of a suboptimal concentration of Protein #21-His (2 nM in BT474 and 4 nM in MDA-MB175). A combination of both molecules was superior to GDC-0941 by itself in both cell lines. GDC-0941 showed activity by itself but potency was increased in combination with Protein #21-His. The potency of GDC-0941 in BT474 was strongly increased, suggesting a synergistic effect. Similarly, Protein #21-His increased the potency of GDC-0941 in MDA-MB175 cells, where the effect appeared to be additive. $IC_{50}$ values are given in Table 3. These data show that Protein #21-His can be combined with GDC-0941 and potentiates its activity.

Combination of Protein #21-His Everolimus, a mTOR inhibitor: Protein #21-His, Everolimus, or a combination of Protein #21-His and Everolimus were tested for their ability to inhibit proliferation of BT474 and MDA-MB175 cells. Everolimus was titrated starting at 1 mM on top of a suboptimal concentration of Protein #21-His (2 nM in BT474 and 4 nM in MDA-MB175). A combination of both molecules was superior to Everolimus by itself in both cell lines. Everolimus showed activity by itself but potency was increased in combination with Protein #21-His. The potency of Everolimus in BT474 cells was strongly increased, suggesting a synergistic effect. Similarly, Protein #21-His increased the potency of Everolimus in MDA-MB175 cells, where the effect appeared to be additive. $IC_{50}$ values are given in Table 3. These data show that Protein #21-His can be combined with Everolimus and potentiates its activity.

Combination of Protein #21-His Lapatinib, a pan-HER inhibitor: Protein #21-His, Lapatinib, or a combination of Protein #21-His and Lapatinib were tested for their ability to inhibit proliferation of BT474 and MDA-MB175 cells. Lapatinib was titrated starting at 10000 nM on top of a suboptimal concentration of Protein #21-His (2 nM in BT474 and 4 nM in MDA-MB175). A combination of both molecules was superior to Lapatinib by itself in both cell lines. Lapatinib showed activity by itself but potency was increased in combination with Protein #21-His. The potency of Lapatinib in BT474 cells was strongly increased, suggesting a synergistic effect. Similarly, Protein #21-His increased the potency of Lapatinib in MDA-MB175 cells, where the effect appeared to be additive. $IC_{50}$ values are given in Table 3. These data show that Protein #21-His can be combined with Lapatinib and potentiates its activity.

Combination of Protein #21 with Trastuzumab: Protein #21, Trastuzumab, or a combination of Protein #21 and Trastuzumab were tested for their ability to inhibit proliferation of BT474 and MDA-MB175 cells. Trastuzumab was titrated starting at 100 nM on top of a suboptimal concentration of Protein #21 (1 nM in BT474 and 10 nM in MDA-MB175). A combination of both molecules was superior to Trastuzumab by itself in both cell lines. Trastuzumab showed only limited activity by itself and induced only cell proliferation arrest but not apoptosis, whereas Protein #21 induces apoptosis. A combination of a suboptimal concentration of Protein #21 with Trastuzumab resulted in inhibition of proliferation. This shows that both molecules can be combined and that Protein #21 potentiates the activity of Trastuzumab. The effect of a combination could also be confirmed by titrating Protein #21 on top of a constant concentration of Trastuzumab (50 nM).

Similarly, the combination of Protein #21 with Apitolisib, Taselisib, Alpelisib, Palbociclib, Trametinib, Cobimetinib or Salirasib was more efficient in inhibiting the proliferation of BT474 cells than either Protein #21 alone or Apitolisib, Taselisib, Alpelisib, Palbociclib, Trametinib, Cobimetinib or Salirasib alone (see Table 3). For the experiments with Apitolisib, Taselisib, Alpelisib, or Palbociclib, Protein #21 was used at 2 nM and the concentrations of Apitolisib, Taselisib, Alpelisib, or Palbociclib were titrated to determine the $IC_{50}$ values. For the experiments with Trametinib ($10^{-5}$ M), Cobimetinib ($10^{-5}$ M) or Salirasib ($3*10^{-5}$ M), Protein #21 was titrated to determine the $IC_{50}$ values.

In summary, Protein #21 or Protein #21-His could be combined with several classes of breast cancer standard-of-care drugs to potentiate their growth inhibitory effects on HER2-overexpressing cells. This indicates clinical possibilities of enhanced efficacy and/or a reduction of standard-of-care dose to reduce toxicity.

TABLE 3

Examples of cell proliferation inhibition constants ($IC_{50}$ [nM]) of different compounds and combination of Protein #21-His or Protein #21 with the compounds on BT474 or MDA-MB175 cells

| Compound | BT474 | MDA-MB175 |
|---|---|---|
| Lapatinib | 765 | 2814 |
| Lapatinib + Protein #21-His | 132 | 784 |
| GDC-0941 | 176 | 203 |
| GDC-0941 + Protein #21-His | 38 | 83 |
| Everolimus | | 263490 |
| Everolimus + Protein #21-His | | 148441 |
| Eribulin | | 104 |
| Eribulin + Protein #21-His | | 27 |
| Apitolisib | 204 | |
| Apitolisib + Protein #21 | 105 | |
| Taselisib | 105 | |
| Taselisib + Protein #21 | 14 | |
| Alpelisib | 2544 | |
| Alpelisib + Protein #21 | 350 | |
| Palbociclib | 2599 | |
| Palbociclib + Protein #21 | 144 | |
| Trametinib | 1.04 | |
| Trametinib + Protein #21 | 0.45 | |
| Cobimetinib | 1.02 | |
| Cobimetinib + Protein #21 | 0.51 | |
| Salirasib | 0.94 | |
| Salirasib + Protein #21 | 0.43 | |

The invention claimed is:

1. A recombinant binding protein comprising an amino acid sequence that has at least 92% amino acid sequence identity with SEQ ID NO: 21, wherein said binding protein comprises two ankyrin repeat domains with binding specificity for Human Epidermal Growth Factor Receptor 2 (HER2) and two ankyrin repeat domains with binding specificity for serum albumin.

2. The recombinant binding protein of claim 1, wherein said binding protein comprises an amino acid sequence that has at least 95% amino acid sequence identity with SEQ ID NO: 21.

3. The recombinant binding protein of claim 1, wherein each of said two ankyrin repeat domains with binding specificity for serum albumin comprises the amino acid sequence of SEQ ID NO: 14.

4. The recombinant binding protein of claim 3, wherein each of said ankyrin repeat domains with binding specificity for serum albumin exhibits improved storage stability in PBS compared to an ankyrin repeat domain with binding specificity for serum albumin comprising the amino acid sequence of SEQ ID NO: 13.

5. The recombinant binding protein of claim 1, wherein said binding protein comprises the amino acid sequence of SEQ ID NO: 21.

6. The recombinant binding protein of claim 1, wherein said binding protein consists of the amino acid sequence of SEQ ID NO: 21.

7. The recombinant binding protein of claim 1, wherein said binding protein inhibits BT474 cell proliferation with an inhibition constant below 10-7M.

8. The recombinant binding protein of claim 1, wherein said binding protein at a concentration of 100 nM exhibits stronger downregulation of AKT-5473 phosphorylation in BT474 cells than trastuzumab at a concentration of 100 nM.

9. A recombinant binding protein comprising a binding domain with binding specificity for HER2 and an ankyrin repeat domain with binding specificity for serum albumin, wherein said binding domain with binding specificity for HER2 comprises the amino acid sequence of SEQ ID NO:16, and wherein said ankyrin repeat domain with binding specificity for serum albumin comprises the amino acid sequence of SEQ ID NO: 14.

10. The recombinant binding protein of claim 9, wherein said binding domain with binding specificity for HER2 and said ankyrin repeat domain with binding specificity for serum albumin are linked by a polypeptide linker.

11. The recombinant binding protein of claim 9, wherein said binding protein comprises an amino acid sequence that has at least 90% amino acid sequence identity with SEQ ID NO: 21.

12. A recombinant binding protein comprising the amino acid sequence of SEQ ID NO: 21.

13. A nucleic acid encoding the recombinant binding protein of claim 1.

14. A pharmaceutical composition comprising the recombinant binding protein of claim 1 and a pharmaceutically acceptable carrier and/or diluent.

15. The recombinant binding protein of claim 1, wherein said binding protein comprises an amino acid sequence that has at least 98% amino acid sequence identity with SEQ ID NO: 21.

16. The recombinant binding protein of claim 1, wherein said binding protein binds to human HER2 in PBS with a dissociation constant (Kd) below 10-7M, and wherein said binding protein binds to human serum albumin in PBS with a dissociation constant (Kd) below 10-7M.

17. A nucleic acid encoding the recombinant binding protein of claim 12.

18. A method of treating a disease in a subject in need of such treatment, the method comprising administering a therapeutically effective amount of the pharmaceutical composition of claim 14 to said subject, wherein the disease is a HER2 expressing cancer.

19. The method of claim 18, wherein the cancer is breast cancer, ovarian cancer, gastric cancer or stomach cancer.

20. The method of claim 18, wherein the HER2 expressing cancer is a HER2-overexpressing cancer, HER2 addicted cancer, partially HER2 addicted cancer, or HER2 amplified cancer.

* * * * *

UNITED STATES PATENT AND TRADEMARK OFFICE
CERTIFICATE OF CORRECTION

| | |
|---|---|
| PATENT NO. | : 10,717,772 B2 |
| APPLICATION NO. | : 15/710001 |
| DATED | : July 21, 2020 |
| INVENTOR(S) | : Clara Metz et al. |

It is certified that error appears in the above-identified patent and that said Letters Patent is hereby corrected as shown below:

In the Claims

Claim 8, Column 89, Line 56, "AKT-5473" should read --AKT-S473--.

Signed and Sealed this
Seventeenth Day of January, 2023

Katherine Kelly Vidal
*Director of the United States Patent and Trademark Office*